United States Patent
Miller et al.

(10) Patent No.: US 11,306,330 B2
(45) Date of Patent: Apr. 19, 2022

(54) GLUCOAMYLASE ENGINEERED YEAST AND FERMENTATION METHODS

(71) Applicant: CARGILL, INCORPORATED, Wayzata, MN (US)

(72) Inventors: Chris Miller, Andover, MN (US); Brian Rush, Minneapolis, MN (US); Brynne Stanton, Boston, MA (US); Joshua Dunn, Boston, MA (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 16/976,550

(22) PCT Filed: Feb. 27, 2019

(86) PCT No.: PCT/US2019/019805
§ 371 (c)(1),
(2) Date: Aug. 28, 2020

(87) PCT Pub. No.: WO2019/168962
PCT Pub. Date: Sep. 6, 2019

(65) Prior Publication Data
US 2021/0002675 A1 Jan. 7, 2021

Related U.S. Application Data

(60) Provisional application No. 62/636,716, filed on Feb. 28, 2018.

(51) Int. Cl.
*C12P 7/10* (2006.01)
*C12N 9/34* (2006.01)
*C12N 1/18* (2006.01)
*C12R 1/865* (2006.01)

(52) U.S. Cl.
CPC .............. *C12P 7/10* (2013.01); *C12N 9/2428* (2013.01); *C12N 1/185* (2021.05); *C12P 2203/00* (2013.01); *C12R 2001/865* (2021.05); *C12Y 302/01003* (2013.01)

(58) Field of Classification Search
CPC ......... C12N 9/2428; C12N 1/185; C12P 7/10; C12P 2203/00; Y02E 50/10; C12Y 302/01003; C12R 2001/865
See application file for complete search history.

(56) References Cited

U.S. PATENT DOCUMENTS

| | | | |
|---|---|---|---|
| 10,364,421 B2 * | 7/2019 | Miller | ................. C07K 14/395 |
| 2011/0269185 A1 | 11/2011 | David | |
| 2012/0045812 A1 | 2/2012 | Bergsma | |

FOREIGN PATENT DOCUMENTS

| | | | |
|---|---|---|---|
| JP | 0 186 066 B1 * | 2/1986 | ............. C12N 15/56 |
| WO | 2001042482 A1 | 6/2001 | |
| WO | 2012019159 A1 | 2/2012 | |
| WO | 2016127083 A1 | 8/2016 | |
| WO | 2016160584 A1 | 10/2016 | |
| WO | 2017106739 A1 | 6/2017 | |
| WO | 2018027131 A1 | 2/2018 | |
| WO | 2018053230 A1 | 3/2018 | |
| WO | 2018204798 A1 | 11/2018 | |
| WO | 2019191263 A1 | 10/2019 | |

OTHER PUBLICATIONS

Putative Glucoamylase (Fragment) {Rhizopus Microsporus] Genbank: CEG69155.1; Publication [online], Apr. 9, 2015. Retrieved from the Internet: <URL:https://www.ncbi.nlm.nih.gov/protein/CEG69155.1?report=genbank&log$=protalign&blast_rank=1&RID=CDXU8B3X015?; p. 1.
Ashikari T et al.: "Rhizopus Raw-Starch-Degrading Glucoamylase Its Cloning and Expression N Yeast", Agricultural and Biological Chemistry, Agricultural Chemical Society of Japan, JP, vol. 50, No. 4, Jan. 1, 1986 (Jan. 1, 1986), pp. 957-964, XP008120586, ISSN: 0002-1369.
Database Geneseq [Online] Mar. 29, 2012 (Mar. 29, 2012), "Rhizopus oryzae glucoamylase (RhGA), SEQ ID 8.", XP002805077, retrieved from EBI accession No. GSP:AZT47646 Database accession No. AZ 147646.
Database Geneseq [Online] Dec. 27, 2018 (Dec. 27, 2018), Rhizopus microsporus glucoamylase, SEQ ID 108 XP002805075, retrieved from EBI accession No. GSP:BFU53535 Database accession No. BFU53535.
Database UniParc [Online] Dec. 15, 2014 (Dec. 15, 2014), "Rhizopus microsporus Glucoamylase", XP002805076, accession No. UniParc—UPI00053810D6 Database accession No. UPI00053810D6.

* cited by examiner

*Primary Examiner* — Ganapathirama Raghu

(57) ABSTRACT

The invention is directed to an engineered yeast including an exogenous nucleic acid encoding a glucoamylase comprising SEQ ID NO:1 and SEQ ID NO:4, or a variant thereof. The engineered yeast are able to provide glucoamylase into a fermentation media and cause degradation of starch material generating glucose for fermentation to a desired bioproduct, such as ethanol. High titers of bioproduct (e.g., 70 g/kg of ethanol) can be achieved, along with low residual glucose levels. Further the yeast exhibit good growth and bioproduct product at temperatures of 32° C. or greater.

13 Claims, 1 Drawing Sheet
Specification includes a Sequence Listing.

SEQUENCE LISTING

```
<160> NUMBER OF SEQ ID NOS: 29

<210> SEQ ID NO 1
<211> LENGTH: 605
<212> TYPE: PRT
<213> ORGANISM: Rhizopus microsporus

<400> SEQUENCE: 1

Met Lys Leu Met Asn Pro Ser Met Lys Ala Tyr Val Phe Phe Ile Leu
1               5                   10                  15
```

```
Ser Tyr Phe Ser Leu Leu Val Ser Ser Ala Ala Val Pro Thr Ser Ala
             20                  25                  30

Ala Val Gln Val Glu Ser Tyr Asn Tyr Asp Gly Thr Thr Phe Ser Gly
             35                  40                  45

Arg Ile Phe Val Lys Asn Ile Ala Tyr Ser Lys Val Val Thr Val Ile
         50                  55                  60

Tyr Ser Asp Gly Ser Asp Asn Trp Asn Asn Asn Asn Lys Val Ser
65                  70                  75                  80

Ala Ala Tyr Ser Glu Ala Ile Ser Gly Ser Asn Tyr Glu Tyr Trp Thr
                 85                  90                  95

Phe Ser Ala Lys Leu Ser Gly Ile Lys Gln Phe Tyr Val Lys Tyr Glu
             100                 105                 110

Val Ser Gly Ser Thr Tyr Tyr Asp Asn Asn Gly Thr Lys Asn Tyr Gln
             115                 120                 125

Val Gln Ala Thr Ser Ala Thr Ser Thr Thr Ala Thr Ala Thr Thr Thr
130                 135                 140

Thr Ala Thr Gly Thr Thr Thr Thr Ser Thr Gly Pro Thr Ser Thr Ala
145                 150                 155                 160

Ser Val Ser Phe Pro Thr Gly Asn Ser Thr Ile Ser Ser Trp Ile Lys
                 165                 170                 175

Asn Gln Glu Glu Ile Ser Arg Phe Ala Met Leu Arg Asn Ile Asn Pro
             180                 185                 190

Pro Gly Ser Ala Thr Gly Phe Ile Ala Ala Ser Leu Ser Thr Ala Gly
             195                 200                 205

Pro Asp Tyr Tyr Tyr Ser Trp Thr Arg Asp Ser Ala Leu Thr Ala Asn
210                 215                 220

Val Ile Ala Tyr Glu Tyr Asn Thr Thr Phe Thr Gly Asn Thr Thr Leu
225                 230                 235                 240

Leu Lys Tyr Leu Lys Asp Tyr Val Thr Phe Ser Val Lys Ser Gln Ser
                 245                 250                 255

Val Ser Thr Val Cys Asn Cys Leu Gly Glu Pro Lys Phe Asn Ala Asp
             260                 265                 270

Gly Ser Ser Phe Thr Gly Pro Trp Gly Arg Pro Gln Asn Asp Gly Pro
             275                 280                 285

Ala Glu Arg Ala Val Thr Phe Met Leu Ile Ala Asp Ser Tyr Leu Thr
290                 295                 300

Gln Thr Lys Asp Ala Ser Tyr Val Thr Gly Thr Leu Lys Pro Ala Ile
305                 310                 315                 320

Phe Lys Asp Leu Asp Tyr Val Val Ser Val Trp Ser Asn Gly Cys Tyr
                 325                 330                 335

Asp Leu Trp Glu Glu Val Asn Gly Val His Phe Tyr Thr Leu Met Val
             340                 345                 350

Met Arg Lys Gly Leu Ile Leu Gly Ala Asp Phe Ala Ala Arg Asn Gly
             355                 360                 365

Asp Ser Ser Arg Ala Ser Thr Tyr Lys Gln Thr Ala Ser Thr Met Glu
370                 375                 380

Ser Lys Ile Ser Ser Phe Trp Ser Asp Ser Asn Asn Tyr Val Gln Val
385                 390                 395                 400

Ser Gln Ser Val Thr Ala Gly Val Ser Lys Lys Gly Leu Asp Val Ser
                 405                 410                 415

Thr Leu Leu Ala Ala Asn Ile Gly Ser Leu Pro Asp Gly Phe Phe Thr
             420                 425                 430

Pro Gly Ser Glu Lys Ile Leu Ala Thr Ala Val Ala Leu Glu Asn Ala
```

```
            435                 440                 445
Phe Ala Ser Leu Tyr Pro Ile Asn Ser Asn Leu Pro Ser Tyr Leu Gly
        450                 455                 460

Asn Ser Ile Gly Arg Tyr Pro Glu Asp Thr Tyr Asn Gly Asn Gly Asn
465                 470                 475                 480

Ser Gln Gly Asn Pro Trp Phe Leu Ala Val Asn Ala Tyr Ala Glu Leu
                485                 490                 495

Tyr Tyr Arg Ala Ile Lys Glu Trp Ile Ser Asn Gly Lys Val Thr Val
            500                 505                 510

Ser Asn Ile Ser Leu Pro Phe Phe Lys Lys Phe Asp Ser Ser Ala Thr
        515                 520                 525

Ser Gly Lys Thr Tyr Thr Ala Gly Thr Ser Asp Phe Asn Asn Leu Ala
        530                 535                 540

Gln Asn Ile Ala Leu Gly Ala Asp Arg Phe Leu Ser Thr Val Lys Phe
545                 550                 555                 560

His Ala Tyr Thr Asn Gly Ser Leu Ser Glu Glu Tyr Asp Arg Ser Thr
                565                 570                 575

Gly Met Ser Thr Gly Ala Arg Asp Leu Thr Trp Ser His Ala Ser Leu
            580                 585                 590

Ile Thr Val Ala Tyr Ala Lys Ala Gly Ser Pro Ala Ala
        595                 600                 605

<210> SEQ ID NO 2
<211> LENGTH: 1818
<212> TYPE: DNA
<213> ORGANISM: Rhizopus microsporus

<400> SEQUENCE: 2
atgaagctaa tgaacccatc tatgaaagct tatgtctttt tcatcttatc atacttctct      60
ctcctagttt catctgccgc agtgcctaca tctgctgccg tccaagtgga agttacaat     120 tacgatggca ctaccttctc cggccgtatc ttcgtgaaaa acattgctta ctcaaaagtt     180
gttacagtga tttactccga tggttctgat aattggaaca caataacaa caaagtttca     240 gcagcgtact ccgaagccat tagtggatct aactacgaat actggacttt ctccgcaaag     300
ttgtctggta ttaagcaatt ctacgtaaag tacgaagttt caggttcaac atactacgat     360
aacaatggta ctaaaaacta ccaggtacaa gccacaagcg ctacaagtac aactgccaca     420
gctacaacta caactgctac agggacaaca actacatcaa ccggtccaac atcaaccgca     480
tctgtctcct ttccaaccgg taacagtaca atatcatcat ggatcaaaaa ccaagaggaa     540
atctcaagat ttgcaatgtt gagaaacatc aatccaccag ggtcagcgac tggtttcatc     600
gccgcttcat tgtccaccgc tgggccagac tactattact cttggactag agactctgca     660
ttgacagcaa acgttatagc ttacgaatac aacacaacct tcactggtaa cactaccttg     720
ttgaagtatc ttaaagacta cgtcactttt agtgttaagt ctcaatctgt ttctaccgtc     780
tgtaactgtt taggtgaacc aaagtttaat gcagatggc catcatttac tggtccatgg     840
ggcagacctc aaaacgatgg accagcagaa agagcagtca cattcatgtt gatcgctgac     900
tcatacttga cacaaactaa ggatgcttca tacgtgactg aacactcaa gccagccata     960 ttcaaagacc tggattatgt tgtttctgtg tggtctaatg gttgctacga tttgtgggag    1020
gaagttaatg gcgtacattt ctacacacta atggttatga aaagggact aattcttggg    1080 gcagatttcg cagctagaaa tggtgattcc tcaagagcat ctacctacaa gcaaacagca    1140
tctacaatgg aatcaaagat cagctctttc tggtctgact ctaacaacta cgttcaagtt    1200
```

```
tcacaatctg tgactgctgg tgtaagtaaa aagggtttag atgtttctac tctgttagct    1260
gcaaacattg gttctttacc agatggcttc tttacaccag gatcagaaaa gattttggca    1320
actgccgttg ccttagagaa tgcattcgct tcccttttacc ctattaactc taacttacct   1380
tcatatttgg gtaattcaat tggtagatat ccagaggaca catacaacgg aaacgggaat    1440
tcacagggca acccttggtt cttagccgta acgcgtacg ccgagttata ctacagagcc     1500
attaaggaat ggatctcaaa tggtaaggta acagtctcta atatctctct tccttttcttt    1560 aaaaagttcg attctagcgc cactagcggc aagacctata cagccggaac aagtgatttc    1620 aataaccctcg ctcagaacat agctcttgga gcagacagat ttctgtcaac tgttaaattt    1680
cacgcgtaca caaatggcag cttgtctgaa gagtacgatc gttccaccgg gatgagtact    1740
ggtgctagag atctaacctg gtcccatgca tctcttatca cagttgcata cgcaaaagct    1800
ggatctcctg ctgcgtaa                                                  1818

<210> SEQ ID NO 3
<211> LENGTH: 1818
<212> TYPE: DNA
<213> ORGANISM: Rhizopus microsporus

<400> SEQUENCE: 3
atgaaactta tgaatccatc tatgaaggca tacgttttct ttatcttaag ctacttctct     60
ttactcgtta gctcagctgc ggtgccaacc tctgccgccg tacaagttga gtcatacaat    120
tatgacggta ccacttttc aggtagaata ttcgtcaaaa acattgccta ctcaaaggtc    180
gtaacagtta tctactccga tggatcagat aactggaaca ataacaacaa caaagtttct    240
gcagcttact cagaagcaat ttctgggtct aactacgaat actggacatt ctccgcaaag    300
ttatccggaa ttaaacagtt ttatgtcaaa tacgaagttt ctggttcaac atattacgac    360
aacaacggta ccaaaaacta ccaagtccaa gcaacctcag cgacatctac aacagctact    420
gcaaccacaa ctacagctac tggcacaaca actacttcta caggtccaac tagtactgca    480
tccgtatcat tccctaccgg taactcaaca atttcttcct ggataaaaaa tcaagaggaa    540
atcagccgtt ttgctatgtt gagaaatatc aatccacctg gtctgccac agggttcata    600 gccgcatctc tgtccacagc cggcccagat tactattact cttggactag agattcagca    660
ctaacagcta atgtgatcgc ttacgaatac aacacaacat tcactggaaa caccacccttt   720 cttaagtact tgaaagatta cgttacattt tctgtcaaaa gccaatctgt atctaccgtt    780
tgtaactgtc tgggagaacc aaagttcaac gctgatggta gttcttttac aggtccatgg    840
ggcagaccac aaaacgacgg accagcagag agagctgtta ctttatgtt gattgctgac     900 agctacttga ctcaaactaa ggacgcatcc tacgttaccg gtacattaaa gccagcaatc    960
ttcaaagatc ttgattacgt agtttctgtt tggtctaacg gttgctacga tttatgggaa    1020
gaggttaatg gtgttcattt ctatactctc atggtcatga aaagggttt gatcttaggt    1080 gccgacttcg ctgctagaaa tggtgactct agtagagctt caacctacaa gcaaactgca    1140
tcaacaatgg aatcaaagat cagttctttt tggtcagatt ctaacaacta cgtccaagtt    1200
tctcaatcag ttaccgccgg agtgtcaaaa aagggactag atgttagtac actattggcg    1260
gccaacattg gtagtctgcc tgatggcttt ttcactccag gctccgaaaa gatattggct    1320
acagcagtgg cgttagaaaa tgcattcgca tccttgtacc caattaactc taacctacct    1380
tcttacttgg gtaactcaat tggaagatat cctgaggata catacaacgg taatggcaac    1440
```

-continued

```
tctcagggga atccatggtt ccttgccgtc aacgcatacg cagaacttta ctacagagct    1500
attaaggaat ggattagtaa tggcaaggtg acagtatcca atatctcact acctttcttc    1560
aaaaagtttg attcttccgc cacttctgga aagacataca ctgctggtac atcagatttc    1620
aataacttgg ctcagaacat tgctttaggc gccgatagat tcctgtctac tgttaagttc    1680
cacgcataca ctaacgggag tctatcagaa gagtacgata gatctaccgg tatgagtact    1740
ggggctcgtg atttaacatg gtcccatgct tcattgatca cagtggcgta cgcaaaggcc    1800
ggtagtcctg cagcttag                                                   1818
```

<210> SEQ ID NO 4
<211> LENGTH: 604
<212> TYPE: PRT
<213> ORGANISM: Rhizopus delemar

<400> SEQUENCE: 4

```
Met Gln Leu Phe Asn Leu Pro Leu Lys Val Ser Phe Leu Val Leu
1               5                   10                  15

Ser Tyr Phe Ser Leu Leu Val Ser Ala Ala Ser Ile Pro Ser Ser Ala
                20                  25                  30

Ser Val Gln Leu Asp Ser Tyr Asn Tyr Asp Gly Ser Thr Phe Ser Gly
            35                  40                  45

Lys Ile Tyr Val Lys Asn Ile Ala Tyr Ser Lys Lys Val Thr Val Ile
50                  55                  60

Tyr Ala Asp Gly Ser Asp Asn Trp Asn Asn Asn Gly Asn Thr Ile Ala
65                  70                  75                  80

Ala Ser Tyr Ser Ala Pro Ile Ser Gly Ser Asn Tyr Glu Tyr Trp Thr
                85                  90                  95

Phe Ser Ala Ser Ile Asn Gly Ile Lys Glu Phe Tyr Ile Lys Tyr Glu
            100                 105                 110

Val Ser Gly Lys Thr Tyr Tyr Asp Asn Asn Asn Ser Ala Asn Tyr Gln
        115                 120                 125

Val Ser Thr Ser Lys Pro Thr Thr Thr Ala Thr Ala Thr Thr Thr
130                 135                 140

Thr Ala Pro Ser Thr Ser Thr Thr Thr Pro Pro Ser Ser Ser Glu Pro
145                 150                 155                 160

Ala Thr Phe Pro Thr Gly Asn Ser Thr Ile Ser Ser Trp Ile Lys Lys
                165                 170                 175

Gln Glu Gly Ile Ser Arg Phe Ala Met Leu Arg Asn Ile Asn Pro Pro
            180                 185                 190

Gly Ser Ala Thr Gly Phe Ile Ala Ala Ser Leu Ser Thr Ala Gly Pro
        195                 200                 205

Asp Tyr Tyr Tyr Ala Trp Thr Arg Asp Ala Ala Leu Thr Ser Asn Val
210                 215                 220

Ile Val Tyr Glu Tyr Asn Thr Thr Leu Ser Gly Asn Lys Thr Ile Leu
225                 230                 235                 240

Asn Val Leu Lys Asp Tyr Val Thr Phe Ser Val Lys Thr Gln Ser Thr
                245                 250                 255

Ser Thr Val Cys Asn Cys Leu Gly Glu Pro Lys Phe Asn Pro Asp Gly
            260                 265                 270

Ser Gly Tyr Thr Gly Ala Trp Gly Arg Pro Gln Asn Asp Gly Pro Ala
        275                 280                 285

Glu Arg Ala Thr Thr Phe Ile Leu Phe Ala Asp Ser Tyr Leu Thr Gln
    290                 295                 300
```

```
Thr Lys Asp Ala Ser Tyr Val Thr Gly Thr Leu Lys Pro Ala Ile Phe
305                 310                 315                 320

Lys Asp Leu Asp Tyr Val Val Asn Val Trp Ser Asn Gly Cys Phe Asp
            325                 330                 335

Leu Trp Glu Glu Val Asn Gly Val His Phe Tyr Thr Leu Met Val Met
                340                 345                 350

Arg Lys Gly Leu Leu Leu Gly Ala Asp Phe Ala Lys Arg Asn Gly Asp
            355                 360                 365

Ser Thr Arg Ala Ser Thr Tyr Ser Ser Thr Ala Ser Thr Ile Ala Asn
        370                 375                 380

Lys Ile Ser Ser Phe Trp Val Ser Ser Asn Asn Trp Ile Gln Val Ser
385                 390                 395                 400

Gln Ser Val Thr Gly Val Ser Lys Lys Gly Leu Asp Val Ser Thr
            405                 410                 415

Leu Leu Ala Ala Asn Leu Gly Ser Val Asp Asp Gly Phe Phe Thr Pro
                420                 425                 430

Gly Ser Glu Lys Ile Leu Ala Thr Ala Val Ala Val Glu Asp Ser Phe
            435                 440                 445

Ala Ser Leu Tyr Pro Ile Asn Lys Asn Leu Pro Ser Tyr Leu Gly Asn
450                 455                 460

Ser Ile Gly Arg Tyr Pro Glu Asp Thr Tyr Asn Gly Asn Gly Asn Ser
465                 470                 475                 480

Gln Gly Asn Pro Trp Phe Leu Ala Val Thr Gly Tyr Ala Glu Leu Tyr
            485                 490                 495

Tyr Arg Ala Ile Lys Glu Trp Ile Gly Asn Gly Val Thr Val Ser
            500                 505                 510

Ser Ile Ser Leu Pro Phe Phe Lys Lys Phe Asp Ser Ser Ala Thr Ser
            515                 520                 525

Gly Lys Lys Tyr Thr Val Gly Thr Ser Asp Phe Asn Asn Leu Ala Gln
            530                 535                 540

Asn Ile Ala Leu Ala Ala Asp Arg Phe Leu Ser Thr Val Gln Leu His
545                 550                 555                 560

Ala His Asn Asn Gly Ser Leu Ala Glu Glu Phe Asp Arg Thr Thr Gly
                565                 570                 575

Leu Ser Thr Gly Ala Arg Asp Leu Thr Trp Ser His Ala Ser Leu Ile
            580                 585                 590

Thr Ala Ser Tyr Ala Lys Ala Gly Ala Pro Ala Ala
        595                 600

<210> SEQ ID NO 5
<211> LENGTH: 1815
<212> TYPE: DNA
<213> ORGANISM: Rhizopus delemar

<400> SEQUENCE: 5
atgcagctgt tcaacttgcc attaaaggtt tcattctttt tggtcctatc atactttagt      60
ttgttggtgt cagccgcatc tattccatct tcagcatctg tacaattaga ctcctacaat     120
tacgacggct ctacattcag cggaaagatt tacgtgaaaa atattgcgta cagcaaaaaa     180
gtaactgtta tctatgccga cggatcagat aactggaaca caatggaaa cactatcgct     240 gccagttact ctgcaccaat ttcaggttct aactacgaat attggacatt tcagcctcc      300 atcaatggca ttaggaatt ctacataaag tacgaagttt ccgtaagac ttactacgat      360 aacaacaatt ctgcaaacta tcaagtatca acatcaaaac ctactaccac caccgccaca     420
```

```
gctacaacta caactgcacc ttcaacatct accacaaccc caccatcttc tagcgaacca    480
gctacattcc caactggcaa ttctactatt tctagttgga tcaaaaaaca agagggtatt    540
tccagattcg caatgttgag aaacataaat ccaccaggat cagcaactgg attcatcgca    600
gcttctttgt ccacagcggg gccagattac tactacgcat ggaccagaga tgctgctttg    660
acaagtaacg ttattgttta cgaatacaat accactttgt ccggtaacaa gactattctt    720
aacgtcctaa aggattacgt tacattctct gttaagactc agtctacatc cacagtctgc    780
aattgtttgg gtgaaccaaa gttcaaccca gatggctctg gatacacagg tgcctggggt    840
cgtccacaaa acgatgggcc tgccgagaga gccactacat ttatcctatt tgctgactca    900
taccttacac aaacaaaaga tgcatcctac gtgactggaa cattaaagcc tgcaatcttc    960
aaagacctgg attacgttgt caacgtgtgg tctaacggct gtttcgatct atgggaagag   1020
gttaacggcg tgcacttcta cactctaatg gtcatgagaa agggtctgtt gttaggtgca   1080
gattttgcta agaaaacgg tgattctaca cgtgcttcta cctactcctc aacagcatca   1140
actattgcga acaagatttc ttcattttgg gtttcaagta ataactggat acaagtatct   1200
caaagcgtta caggggtgt ctcaaaaaag ggtcttgatg tttctacatt actggctgct   1260
aatcttgggt ctgttgatga cggtttcttc acccctggtt ctgaaaagat cctcgctacc   1320
gccgtcgcgg ttgaggatag ttttgcttca ctctatccta taaacaaaaa ccttccttca   1380
tacttaggaa acagtatcgg tagatacccca gaggatacat acaatggtaa tgcaattca   1440 cagggaaatc catggttcct tgctgttaca gggtacgcag aactttacta tagagctatt   1500
aaggaatgga tcggcaacgg cggtgtgaca gtttcctcaa tctcattgcc attttcaaa   1560 aagtttgact ccagcgcgac atctggtaaa aagtatactg tggggacttc tgatttcaac   1620
aatttggctc aaaacattgc cttagctgcc gacagattct tatctaccgt acaactccat   1680
gcacataaca atggtagttt ggcagaggaa tttgatagaa ctacaggact ctctacaggt   1740
gcgagagatt taacttggtc acatgcaagt ttaattacag cctcttacgc aaaggctggt   1800
gctcctgctg cataa                                                   1815
```

<210> SEQ ID NO 6
<211> LENGTH: 1815
<212> TYPE: DNA
<213> ORGANISM: Rhizopus delemar

<400> SEQUENCE: 6

```
atgcagttat tcaacttacc acttaaggta tctttctttc tagtcttatc ttacttttca     60
ttgttagtat cagctgcctc tataccaagt tcagcatccg tacaactaga ttcatacaat    120
tacgacggtt caacattctc aggaaagata tacgtgaaaa atattgctta cagcaaaaag    180
gttactgtga tttacgcaga tgggtcagac aactggaata caatggaaa cacaattgct    240 gcttcctatt ctgcccctat ttctggatct aactacgaat actggacttt ttcagcgagt    300
ataaacggaa ttaaggaatt ctatatcaaa tatgaagtct ctggtaagac ctactacgat    360
aacaacaact ccgcaaacta ccaagttagc catcaaaagc caaccacaac aactgctact    420
gcgacaacta caaccgcacc aagcacttct actacaacac ctcctagttc atctgagcca    480
gcaactttcc caactggtaa ttccactatt tcttcttgga tcaaaaaaca agagggtatc    540
tcaagattcg ccatgcttag aaatatcaat cctccaggct ctgcaacagg attcattgca    600
gcatctttat caactgcggg gccagactac tactacgcct ggactagaga tgcagctttg    660
acatcaaatg tgattgttta tgaatacaac acaactttgt ccggtaacaa gacaatcttg    720
```

```
aacgtcttga aggattatgt gacattctct gtcaagactc aatctacatc aacagtttgt      780
aactgtctcg gcgaaccaaa gttcaaccct gatggtagtg gttacactgg tgcttggggt      840
agaccacaaa acgatggtcc agcagagaga gctacaactt tcatcttgtt tgctgactct      900
tacctaacac aaaccaagga tgcaagctac gttactggaa cactaaagcc tgcaatcttt      960
aaagacctgg actatgttgt aaacgtttgg tcaaatggct gcttcgatct atgggaggaa     1020
gtgaacggtg ttcacttcta cacattaatg gtcatgagaa agggactctt gcttggtgca     1080
gactttgcta agagaaacgg tgattctaca cgtgcctcca cttactcctc cacagcttca     1140
accattgcca caaaaatctc ttctttctgg gtcagctcaa ataactggat tcaagtttct     1200
caatcagtta ctggtggtgt ttctaaaaag ggcctggatg tgtcaacctt gcttgctgcc     1260
aatttgggca gtgttgatga cgggttcttc accccaggtt ctgaaaagat cctcgccacc     1320
gcagttgccg ttgaagattc atttgctagt ttatacccaa tcaacaaaaa tctaccatca     1380
taccttggaa attcaatcgg tagatatcca gaggatacat acaacggtaa tggaaactct     1440
cagggtaacc cttggtttct tgcagttaca gggtacgctg aactgtacta cagagcgatt     1500
aaggaatgga ttggtaatgg cggcgtaact gttagttcta tttctctacc tttcttcaaa     1560
aagttcgata gttctgcaac atctggtaaa aagtacacag tcggcacttc cgattttaac     1620
aatttagctc agaacatagc actggcagct gatcgtttct tgagtacagt ccaattgcat     1680
gcccataaca acggtagttt ggctgaagag tttgataaga ccaccggttt atcaaccggc     1740
gccagagatt taacatggtc ccatgcgtct ttgataactg cttcttacgc caaggctggg     1800
gcaccagctg cctga                                                       1815

<210> SEQ ID NO 7
<211> LENGTH: 1815
<212> TYPE: DNA
<213> ORGANISM: Rhizopus delemar

<400> SEQUENCE: 7
atgcagttat tcaacttacc acttaaggta tcttttcttt cagtcttatc ttacttttca       60
ttgttagtat cagctgcctc tataccaagt tcagcatccg tacaactaga ttcatacaat      120
tacgacggtt caacattctc aggaaagata tacgtgaaaa atattgctta cagcaaaaag      180
gttactgtga tttacgcaga tgggtcagac aactggaata caatggaaa cacaattgct      240 gcttcctatt ctgcccctat ttctggatct aactacgaat actggacttt tcagcgagt      300 ataaacggaa ttaaggaatt ctatatcaaa tatgaagtct ctggtaagac ctactacgat      360
aacaacaact ccgcaaacta ccaagttagc acatcaaagc caaccacaac aactgctact      420
gcgacaacta caaccgcacc aagcacttct actacaacac tcctagttc atctgagcca       480 gcaactttcc caactggtaa ttccactatt tcttcttgga tcaaaaaaca gagggtatc       540 tcaagattcg cctgcttag aaatatcaat cctccaggct ctgcaacagg attcattgca      600
gcatctttat caactgcggg gccagactac tactacgcct ggactagaga tgcagctttg      660
acatcaaatg tgattgttta tgaatacaac acaactttgt ccggtaacaa gacaatcttg      720
aacgtcttga aggattatgt gacattctct gtcaagactc aatctacatc aacagtttgt      780
aactgtctcg gcgaaccaaa gttcaaccct gatggtagtg gttacactgg tgcttggggt      840
agaccacaaa acgatggtcc agcagagaga gctacaactt tcatcttgtt tgctgactct      900
tacctaacac aaaccaagga tgcaagctac gttactggaa cactaaagcc tgcaatcttt      960
```

-continued

```
aaagacctgg actatgttgt aaacgtttgg tcaaatggct gcttcgatct atgggaggaa    1020
gtgaacggtg ttcacttcta cacattaatg gtcatgagaa agggactctt gcttggtgca    1080
gactttgcta agagaaacgg tgattctaca cgtgcctcca cttactcctc cacagcttca    1140
accattgcca acaaaatctc ttctttctgg gtcagctcaa ataactggat tcaagtttct    1200
caatcagtta ctggtggtgt ttctaaaaag ggcctggatg tgtcaacctt gcttgctgcc    1260
aatttgggca gtgttgatga cgggttcttc accccaggtt ctgaaaagat cctcgccacc    1320
gcagttgccg ttgaagattc atttgctagt ttatacccaa tcaacaaaaa tctaccatca    1380
taccttggaa attcaatcgg tagatatcca gaggatacat acaacggtaa tggaaactct    1440
cagggtaacc cttggtttct tgcagttaca gggtacgctg aactgtacta cagagcgatt    1500
aaggaatgga ttggtaatgg cggcgtaact gttagttcta tttctctacc tttcttcaaa    1560
aagttcgata gttctgcaac atctggtaaa aagtacacag tcggcacttc cgattttaac    1620
aatttagctc agaacatagc actggcagct gatcgtttct tgagtacagt ccaattgcat    1680
gcccataaca acggtagttt ggctgaagag tttgatagaa ccaccggttt atcaaccggc    1740
gccagagatt taacatggtc ccatgcgtct ttgataactg cttcttacgc caaggctggg    1800
gcaccagctg cctga                                                    1815

<210> SEQ ID NO 8
<211> LENGTH: 1818
<212> TYPE: DNA
<213> ORGANISM: Rhizopus microsporus

<400> SEQUENCE: 8
atgaagctga tgaatcctag catgaaagca tatgtgtttt tcatcctctc atacttcagc      60
ttgctagtta gttcggccgc agtacccacg tcggccgcgg tccaagtgga gtcgtataat     120
tatgacggaa ctaccttctc agggcgtata ttcgtcaaga atattgcgta ttccaaagtc     180
gtcacagtaa tctattcaga tggctccgat aattggaata ataataacaa caaggttagc     240
gccgcctatt ccgaggctat ttctggatca aactacgaat actggacctt ctcggcgaag     300
ctgtcaggga tcaaacagtt ttacgtcaag tacgaggtca gtggttcaac ttactacgat     360
aataacggaa ccaaaaatta tcaggtccag gcgacgagcg caacgtccac aactgcgaca     420
gccactacca ctactgctac cgggactacg acaacctcga caggaccgac gtccaccgcc     480
tctgtatcct ttcccaccgg aaacagcaca atttcgagct ggataaaaaa ccaagaggaa     540
atctctcgct tcgctatgtt acgtaacatc aatccccccg gttcggcaac tgggtttatt     600
gccgcatcat tatctacagc cgggcccgat tactattata gctggactcg cgacagtgca     660
ctcacggcta atgtcatcgc atatgaatac aacacgactt tcaccggcaa tacgaccctt     720
cttaagtatt tgaaagatta tgtaactttc tcagttaaaa gtcaatcggt tagtacggtc     780
tgtaattgtc tcggtgaacc gaagtttaac gctgacgggt cctcgttcac tggcccttgg     840
gggcgacctc agaacgacgg gcccgcggaa cgcgccgtta cgttcatgct cattgcagac     900
tcatatctca cccagactaa agacgcgtct tatgtcactg ggactttaaa accagctata     960
tttaaagatc tggattacgt tgtttctgtt ggtcaaatg gtgttatga cttatgggaa    1020 gaagtgaacg gcgttcattt ctacacttta atggtcatgc ggaagggcct cattttaggg    1080
gcggacttcg ccgcacgtaa tggagattca tcgcgcgcgt caacatataa acaaacggca    1140
tcaactatgg aaagtaaaat ttctagcttc tggtcggaca gtaacaacta cgttcaagtg    1200
tctcaatcgg taactgcggg ggtaagcaag aagggacttg acgtgagtac actgcttgcc    1260
```

```
gccaatattg ggagcctacc agacgggttt tttacacccg gctcggaaaa gattttagca      1320
acggctgttg ctcttgaaaa cgcttttgcc tcgctgtatc caatcaattc aaatttacca      1380
tcttatctgg gaaatagtat tggaaggtac cccgaggaca cctataatgg aacggtaat       1440 tcccaaggta acccttggtt cttggctgtg aatgcctatg ccgagttgta ctatcgcgca      1500
attaaggaat ggataagtaa tggcaaagtg acggtttcaa acatctccct acctttttc       1560 aaaaaattcg actccagtgc gacttctgga aaaacctata cagcgggcac ctccgacttc      1620
aataatctcg cgcagaatat tgcactcgga gcagaccgat ttctttctac agtgaaattc      1680
catgcgtaca cgaacggtag cttgtcagaa gagtacgacc ggtctaccgg catgtcaacg      1740
ggagcacgag atcttacttg gtcccatgca agtttaatta ctgtggcata cgctaaagca      1800
gggtcgccag cggcataa                                                    1818

<210> SEQ ID NO 9
<211> LENGTH: 1800
<212> TYPE: DNA
<213> ORGANISM: Artificial Sequence
<220> FEATURE:
<223> OTHER INFORMATION: Mfa2-Rhizopus oryzae

<400> SEQUENCE: 9
atgaaattca tttctacctt tctcactttt attttagcgg ccgtttctgt cactgctggt        60
gcctcgatcc ccagctcggc cagcgtccaa ctggactcgt ataattatga cggatctacc       120
ttctcaggga aaatatacgt caagaatatt gcgtattcca aaaaagtcac agtagtctat       180
gccgatggct ccgataattg gaataataat ggaaacacaa ttgcggcctc attttccggg       240
cctatttctg gatcaaacta cgaatactgg accttctcgg cgtcggtgaa agggatcaaa       300
gagttttaca ttaagtacga ggtcagtggt aaaacttact acgataataa caactcagct       360
aattatcagg tcagcacgag caagccgact acaactacgg cagccactac cactactact       420
gccccgtcta cgagtaccac aacacggccg agttcctcag aacctgcaac ttttcccacc       480
ggaaacagca caatttcgag ctggataaaa aagcaagagg atatctctcg cttcgctatg       540
ttacgtaaca tcaatccccc cggttcggca actgggttta ttgccgcatc attatctaca       600
gccgggcccg attactatta tgcgtggact cgcgacgcgg cactcacgtc taatgtcatc       660
gtatatgaat acaacacgac tctatcaggc aataagacca tccttaacgt tttgaaagat       720
tatgtaactt tctcagttaa aacgcaatcg acttcgaccg tctgtaattg cttgggcgag       780
ccaaaattca atccggacgg ttcgggatat accggtgctt ggggccgtcc gcagaacgac       840
ggcccggccg aacgagctac gacgttcgta ttattcgcgg attcatactt gacgcaaact       900
aaggacgctt cctatgttac gggtacttta agcctgcaa ttttaaaga ccttgactat        960 gttgttaatg tctggtcaaa cggttgtttc gatttgtggg aagaggtgaa tggtgttcac      1020
ttctatactc tgatggttat gcggaaagga ttattactag gggcagactt tgcaaaacga      1080
aacggtgatt cgaccagagc ctcgacttat tctagcacag cctccacgat cgcaaataaa      1140
attagcagtt tctgggtaag tagtaacaac tgggtccagg tttctcagtc ggttacgggc      1200
ggcgtaagta agaaggggct tgatgtctca accctactgg cggcaaacct gggttccgta      1260
gatgatggat ttttcactcc tggaagcgaa aaaattcttg ccacagctgt tgccgtagag      1320
gattcgtttg cttcattata tccaattaat aagaacttac cgtcttacct gggaaatgca      1380
ataggccgat atccggagga tacctataat ggtaacggta atagccaagg taacccttgg      1440
```

```
tttcttgcgg tcacaggtta tgcagaactg tattacagag cgatcaaaga atggatatct   1500
aatggaggag ttacagtttc atcgatttct ctccctttct tcaaaaagtt tgactcctca   1560
gctacaagtg gcaaaaaata cacggtcggt acaagcgact ttaataacct cgcacagaac   1620
atcgcccttg ctgccgatag gttcctgagc actgtgcaac ttcatgcacc gaacaacggt   1680
tcattggcag aagagttcga ccgaactacc ggtttctcca ctggagcgcg tgatttaacg   1740
tggagtcatg cttcgctgat cacagcgtcg tatgctaagg caggcgcccc ggctgcctaa   1800
```

<210> SEQ ID NO 10
<211> LENGTH: 1548
<212> TYPE: DNA
<213> ORGANISM: Saccharomycopsis fibuligera

<400> SEQUENCE: 10

```
atgataaggc tcactgtttt cctcaccgca gtcttcgctg cggtcgcatc atgcgtgccg     60
gtcgagttgg acaagcgaaa cacaggccac ttccaagcgt attctgggta cacagttgcc    120
cgttcgaact tacccagtg gatacatgag cagcccgcag tttcttggta ttatttactt     180
caaaacatcg attatcccga aggccaattt aaatctgcta aacctggagt agtagttgcg    240
tcaccctcaa ccagtgaacc cgattacttt taccagtgga cgagagatac agcaataaca    300
ttccttagtc ttattgcaga agtggaagac cacagttttt cgaacactac cttagcgaag    360
gttgttgagt actatatttc caatacatat acactacaga gggtaagcaa tccatctggg    420
aactttgatt cacctaatca tgatgggtta ggggagccca agttcaacgt ggacgatacc    480
gcctatacag cttcatgggg ccggccacag aacgatggac cggcactacg tgcgtatgcg    540
atttcgcgtt atctcaatgc cgttgctaag cataataatg gcaaactcct attagcgggc    600
caaaatggaa tcccttatag ttcagcgtca gatatatatt ggaagatcat taaaccggac    660
ctacagcacg tttctaccca ctggtccact tcggggttcg atctatggga agaaaaccaa    720
ggcacccact ttttactgc cttagtacaa ctaaaagctc ttagttatgg aatccctctc     780
tccaaaacgt acaatgaccc tgggttcact tcgtggttgg aaaaacaaaa ggatgctcta    840
aacagctaca ttaactcatc cggctttgtg aactcgggaa aaaagcacat cgtcgagtcc    900
ccgcaattaa gtagccgtgg tggcttagac tctgctactt acattgcagc tttgattacg    960
catgacattg tgatgatga tacctatacg ccttttaacg ttgataattc atacgtgctt    1020
aattctctat actatttact ggtcgataac aagaatcggt ataaaataaa cggaaactat   1080
aaggctggcg cagctgtcgg acgctacccc gaggatgtct ataacggagt cggtacgtca   1140
gagggcaatc cttggcagct agcaacagcg tacgcaggac aaaccttcta tactctcgca   1200
tataacagtc taaagaacaa gaagaatctc gtgatagaga agcttaatta tgatttgtac   1260
aacagtttca tagcggattt gtcgaaaatc gactcctcgt atgcttcgaa ggattcttta   1320
acccttacat atggttcaga caactataag aatgttatca aatctctatt acaattcgga   1380
gatagttttc tcaaggtatt gctagaccat atcgatgaca acggtcaatt gaccgaagag   1440
attaataggt atactgggtt tcaagctggc gcggtcagtt tgacgtggag tagtgggtca   1500
ttgttaagtg cgaatcgagc acggaataag ttaatcgagt tattataa                1548
```

<210> SEQ ID NO 11
<211> LENGTH: 1920
<212> TYPE: DNA
<213> ORGANISM: Aspergillus kawachii

<400> SEQUENCE: 11

```
atgagcttcc ggtccttgct ggcattgagt ggcctagttt gctcaggact tgcgagtgtg    60
attagtaaaa gagcaaccct cgactcctgg ctctccaacg aagctacggt agcacgtacc   120
gctatcctaa ataatatcgg cgcggatgga gcgtgggtat ctggtgcgga ttccggtatc   180
gtcgtagcat caccttcaac tgataatccc gattattttt atacttggac acgggatagc   240
ggccttgtca ttaagacttt ggttgacctt ttcagaaatg ggacaccga cctcctgtcg   300 acgatcgagc attatatatc aagccaagcg ataatacaag gagtatctaa tcctagcggg   360
gatttgtcga gtggcggttt gggcgagccc aagttcaacg tggacgagac tgcatatacg   420
ggatcatggg gccgtcctca acgagatgga ccagcgctac gcgccaccgc tatgattggc   480
tttggccagt ggctgctaga taacgggtac acatctgcgg ctacggaaat cgtttggcca   540
ttggtccgta atgacctttc atatgtcgct cagtactgga accaaactgg ctacgattta   600
tgggaggaag tgaatggtag ctcattttc accattgccg tgcagcaccg ggcgttagtt   660
gaaggatcgg cctttgcaac ggcggttgga tcatcctgta gctggtgtga tagccaagcc   720
cctcaaattc tatgttacct tcaatcattc tggacaggta gttacatcct tgctaatttc   780
gattccagtc ggtccgggaa agacacgaat acactcttgg gctccattca ccctttgac   840 ccggaggcgg gctgcgatga ttcaactttc cagccatgct ctccaagagc ccttgcaaat   900
cacaaagaag tggtggattc ctttcgtagc atttatactc tcaatgacgg tttgtccgac   960
tcagaggctg ttgctgttgg ccgatatccg gaagatagct attataatgg caacccgtgg  1020 ttttatgca cattagctgc ggccgaacag ctctatgacg cttttatacca gtgggacaaa  1080 cagggttcac tagaaatcac agatgtgtca ctcgattttt tcaaggcctt gtactcagga  1140
gccgctactg gacatactc gtcgagtagt tcgacatatt caagcattgt ttcggcagtt  1200
aagacgttcg cggacgggtt cgtcagcata gtagagacac atgccgccag taacgggtcg  1260
ctaagcgaac aattcgataa atcggatgga gatgaactca gcgctcgtga tcttacctgg  1320
tcttatgccg cactgttaac agccaataat cgtcgtaact ctgttgtgcc acctagttgg  1380
ggagagacat ccgcaagctc agtccccggg acgtgtgccg ccacctccgc atccggtacg  1440
tattccagtg ttaccgttac cagctggcca tctattgtag ctacggggtg aacaacgacc  1500
accgctacga cgactggcag tggaggtgta acttcaacat ctaaaacaac gaccacagcg  1560
tctaagactt ctaccactac aagttcaacc tcctgcacga cccctacagc ggtggccgtt  1620
acattcgacc tcacggccac caccacttac ggggaaaaca tttacctagt ggggtctata  1680
tcccaattag gagactggga gacttcagat ggaatcgcgc tatcggccga taaatatacg  1740
tcctctaacc cgttatggta tgtgacagta actttaccag cgggagagag cttcgaatat  1800
aagttcatcc gagtggaatc agatgatagc gtggagtggg agtcggaccc aaatcgggag  1860
tatactgtcc ctcaggcttg cggtgagtcc actgctaccg taacggatac atggcgctaa  1920
```

<210> SEQ ID NO 12
<211> LENGTH: 1911
<212> TYPE: DNA
<213> ORGANISM: Aspergillus terreus

<400> SEQUENCE: 12

```
atgacgagga tcttgactct ggcattgcac ggcctagctc tggtccagtc agtggtgggg    60
gccccgcaac tagcaccccg ggcaaccacg tcgttggacg cctggctggc atcggaaacc   120
actgtagcat tagatggaat cctggataac gtgggctcgt ctggtgcgta tgctaaatca   180
```

-continued

```
gccaagtcgg gcattgtcat tgcctccccc tccacttccg atcctgacta ctactatacg    240
tggacccgag atgcggcttt gactgtaaaa gcactaatcg acctatttcg aacggggag     300 acatcattgc agaccgtgat tatggagtac atctcgtcgc aagcctatct gcaaactgta    360
agtaatcctt ccggctcgct ttcgacgggc ggtctggcag aacctaaata ttatgttgat    420
gagactgcgt acaccggaag ttgggggcgg cctcaacgag atggaccagc gctacgcgca    480
acggcaatga ttgactttgg gaattggtta attgacaatg ctattctac atatgcctca     540 tccattgtat ggcctatagt ccgtaatgac ctttcttatg tagcccagta ttggaaccaa    600
actgggtatg atttgtggga ggaggtaaac ggttcttcat tcttcaccat tgcagtgcag    660
catagagcct tggtcgaggg ctcaaccttc gcttccaaag tcggtgcatc ttgctcatgg    720
tgtgactctc aggctccaca ggtccttttgt tttctccaac gcttctggac tgggtcttac   780
ataatggcaa actttggcgg tggtaggtca ggtaaggacg cgaacaccgt gcttggttca    840
attcacacgt tcgaccctaa cgcgggctgt gacgatacga cttttcagcc gtgttccccc    900
cgtgcgttag ctaatcacaa agtatatacc gatagctttc ggtccattta ttccattaat    960
tcagggattt ccagcggtaa agctgtcgcg gtgggccgct atccggagga ttcttactat    1020
aatggaaacc cctggttttt aacgacgctc gcggctgccg agcaactata tgacgctatc    1080
tatcagtggc aaaaaatagg cagtattact attacggacg tgtcgctcgc gttcttcaag    1140
gatctttact cttctgcggc ggtagggaca tatgcaagta gtagtagcgc ctttacctca    1200
attgtgagcg cggtaaagac gtatgctgac ggctatatgt ccatcgttca aacacacgct    1260
atgactaatg gctcgttatc cgaacagttc ggtaagtcag atggcttttc tctatctgct    1320
agggacttaa cgtggtcgta cgcagcccta ctgaccgcca atctgaggcg taattccgtc    1380
gttccacctt cctggggtga aacgactgcc acttcagtgc cctcggtttg ttcggctacg    1440
tctgcaacag ggacctattc tacggcgact aatacagcat ggccatctac cctcacttct    1500
ggaacgggcg caacgactac gacttctaaa gctacaagtt catcaactac gacgacctct    1560
tcggcgagct caactacagt agagtgcgtg gtccccaccg ctgtagcggt cacatttgac    1620
gaggtggcga ctacgactta tggtgagaac gtatacgttg tcggcagtat cagtcagctc    1680
ggctcttggg atacgtccaa agcagtggct ttatctgcgt cgaagtatac ttcgagcaac    1740
aacctgtggt atgttacggt aacccttccg gctggcacca cttttccagta caagttcatc    1800 cgggtatcat cgtcgggttc cgtcacttgg gaaagcgatc cgaatcgctc ttatacagtg    1860
ccctcggcct gtggtacgtc aacagctgtc gtcaatacca cttggcgcta a             1911
```

<210> SEQ ID NO 13
<211> LENGTH: 1854
<212> TYPE: DNA
<213> ORGANISM: Thermomyces lanuginosus

<400> SEQUENCE: 13

```
atgctgttcc agcctactct gtgcgccgca cttgggttag cggccctcat cgtgcagggc     60
ggcgaggcac gcccggagac tactgtgcca cacgctaccg gttcgctaga tgatttcctt    120
gcggctcaga gccccatcgc ttttcaggc attttaaata atataggacc ctccggcgct    180
tattccgaag gtgttaatcc cggtgtagta atcgctagcc cctcaaaaca agaccctgat    240
tatttctata catgggtcag ggacgccgca ctcacggtac agtatctagt cgaagagttg    300
gtggcgggaa atgcatcgtt acaatttctg attcaagact acatctcttc ccaagcacga    360
ctccagacgg tggagaaccc ttcgggtagc ctatcatccg gcggtttagg tgaaccgaaa    420
```

```
ttccacgtcg acgagacagc gttcactgat tcctggggac gccccaacg agatgggcca      480 ccattaaggg ctatagctat gatttccttc gctaattatt taatagataa tggccatcaa      540
tcgacagttg aggatattat ctggcccatt gttagaaatg acctttctta cgtcagccaa      600
cattggaaca gacaacatt cgatatttgg gaggaggtcc attcgagtag cttttcacc      660 accgccgtgc aatatcgagc tttggttcaa ggtagtgctc tagcctctaa actaggtcac      720
acttgcgaca attgtggttc tcaggctccc cagatcttgt gctttctaca gtcctactgg      780
actggctccc atatacttgc taacacgggt ggcggtagga gcggaaagga tgtaagtacc      840
atcctcggcg tgattggtag tttcgatcct aatgctgact gtgatgatgt aactttccaa      900
ccctgtagcg cccgggcttt agctaatcat aaacaagtgg ttgatagctt tcgctctatc      960
tacgcgatca atgctgggat cccttctggg tcagctgtag cagtcggacg ttatccggag     1020
gacgtgtatc agggtggcca cccttggtac ttgacgaccg cagctgccgc tgagcagctt     1080
tatgacgcca tatatcaatg gaaccacgtg gacacatag acatcaacgc tgtcaactta     1140
gatttcttca aaagcatata cccgagtgcg gcagaaggaa cgtacacaag cgattcatca     1200
acctttcagg acataatcag tgcggttcgc acatatgccg acggtttctt gtctgtaata     1260
gaaaaatata ccccaccgga taacctttta gccgaacaat tccatcgtga acaggtata      1320 cctctcagcg cagccagtct gacctggtca tacgcggctt tgaataccgc tgcacaacgc     1380
agggcttcca tagttccctc ccctggaat agtaatagca ctgacctacc ggataaatgt     1440
agtgcgactt cagcaacagg tccatatgcc acacctacta acacggcctg ccgactacg      1500 actcagcctc ccgaacggcc ggcctgtact ccgccgtcag aagtaacgct gacctttaac     1560
gcactcgtag acaccgcctt tggtcagaac atctacttgg tgggaagcat acctgagttg     1620
ggctcttggg acccagcaaa tgccttgcta atgagtgcaa agtcatggac ctctgggaat     1680
cctgtatgga cttatctat atcgctacct gctggaacgt cgttcgagta caaatttata     1740
cgcaaagacg atggctcatc tgacgtggta tgggagtcgg acccaaatcg gtcgtataat     1800
gtccctaagg attgcggtgc gaatactgct accgtaaact cctggtggcg ctaa           1854
```

<210> SEQ ID NO 14
<211> LENGTH: 2045
<212> TYPE: DNA
<213> ORGANISM: Artificial Sequence
<220> FEATURE:
<223> OTHER INFORMATION: Mfa2-Neurospora crassa

<400> SEQUENCE: 14

```
atgaaattca tttctacctt tctcactttt attttagcgg ccgtttctgt cactgctgac       60
gcgatctata atctgaagca agtacttcta tctaaccatg actttacgac gagcttggtg      120
tccaacgcaa ccgacttctc cacgtcgccc ctgaccatt tcgcaatgca tttggtttcg      180 agttacttg tagtcgggc tgcattccaa gcagttttag ggttgcctga tcccttcac       240 gagaaacgcc attctgatat tatcaaacgt tccgtcgatt cgtacatcca aacggaaacc      300
cccattgcgc aaaagaacct actttgcaac atcggagcaa gcggatgccg agcctccgga      360
gccgcgtccg gggtggtagt cgcatcgcct tcaaaaagca gtcctgatta ctggtatact      420
tggacccggg atgcagcgct agtgacaaag ttgatcgttg acgagtttac taatgattat      480
aataccacgt tacagaacac catccaggca tacgcggctg cccaagctaa gttgcaaggc      540
gtcagtaacc catccggaag cctcagtaat ggggctgggt taggagaacc caagtttatg      600
```

```
gttgatctac aacaatttac cggtgcatgg ggtaggcccc aacgagatgg gcccctctg    660 cgtgcgatcg ctttgatagg gtacggaaag tggttagtct cgaacggcta tgcagacacg    720
gctaagtcaa ttatttggcc catcgtcaag aatgatttag cctatacagc tcagtattgg    780
aataacactg gatttgacct atgggaagaa gttaactcct ccagtttctt tacgattgcg    840
gcgtcccacc gggctttggt tgaagggtca gctttcgcga agtccgtggg ctcctcatgt    900
agcgcgtgcg acgctatagc gccccaaatc ttgtgctttc aacagagctt ttggtcaaat    960
agcggttata ttatctccaa ctttgtcaat taccgatcgg gtaaagatat taattcagtc   1020
ctaacttcca tacataattt tgatccggcg gccggttgtg acgtaaatac tttccaacct   1080
tgctcggatc gggctttagc gaaccacaag gtcgtagttg atagtatgcg attctggggt   1140
gtgaactcag gtaggaccgc aggcaaagct gcggcagtgg gacggtacgc ggaggacgtt   1200
tattacaatg gtaacccatg gtacctagca acgctagcgg cagccgagca gctatacgac   1260
gccgtctatg tctggaagaa gcagggaagt ataactgtta catccacctc gttggcattt   1320
tttaaggact tagttccttc agtctcgact ggtacctaca gctctagttc ttctacatat   1380
actgcgatca ttaacgctgt aacgacatat gcagacggct ttgtcgacat agttgcccaa   1440
tatactccat ccgatgggtc cttggcgaaa caatttgata aggattcggg tgccccattg   1500
agcgctacac acctaacctg gtcttacgcg tcttttctat cggctgctgc aaggcgcgca   1560
gggattgtgc ctccatcctg gggtgcagcg tcagccaata gtctgcccgg ttcgtgcagc   1620
gcctctacag tagcaggaag ttatgccacc gctacagcga cctcgtttcc ggcaaacctg   1680
actccggctt caactacagt gacaccacct acccaaacag gctgcgcagc agatcatgaa   1740
gttctggtta ctttcaacga aaaagttacg acaagttatg gtcagacggt aaaggtggta   1800
ggttctatag cagcccttgg gaattgggcc cctgcgagcg gagtgacgct ctcggcaaaa   1860
cagtactcct cctcaaatcc attatggtct acgaccattg ctttgcctca agggacctcg   1920
tttaaatata aatatgttgt cgttaatagt gatggatctg taaaatggga gaatgatccc   1980
gatcgcagct atgccgtagg aacagattgt gcttccacag ccactcttga tgatacttgg   2040
aggta                                                              2045
```

<210> SEQ ID NO 15
<211> LENGTH: 4863
<212> TYPE: DNA
<213> ORGANISM: Artificial Sequence
<220> FEATURE:
<223> OTHER INFORMATION: Mfa2-Rhizopus oryzae GA integration construct

<400> SEQUENCE: 15

```
ctaaattcgg ccttgctcag agactcctgg attttggcta acaacgcagt cccttcgatg     60
catatagcta ggccacaaat tatgccaata acggtccatg ggttgatgtt ttcttgaatt    120
ctttcgtttt tcatgctatt tgcgtcttcc caagtcccag cgttccagta ttcatactgc    180
gcgttagagt ggtagccata agagccggca tattggtaat tttcagtatt aacgttagaa    240
cgtggtgaat acgatgtggt ccagccttgc ctcgttgtgt catatacgat cttttttcttt    300 gggtcacaaa gaatatcata tgcttgagag atgacttttaa atctatgtag ttttttcgctt    360 gatgttagca gcagcggtga tttactatca ctgttggtaa cctttctga gctaaatatt    420 tgaatgttat cggaatggtc agggtggtac aattttacat aacgatgata tttttttttt    480
aacgacttct tgtccagttt aggatttcca gatccggcct ttggaatgcc aaaaatatca    540
tagggagttg gatctgccaa ctcaggccat tgttcatccc ttatcgtaag ttttctattg    600
```

```
ccattttat  cgttcgctgt  agcatactta  gctataaaag  tgatttgtgg  gggacacttt    660
tctacacatg  ataagtgcca  cttgaataaa  aatgggtata  cgaacttatg  gtgtagcata    720
acaaatatat  tgcaagtagt  gacctatggt  gtgtagatat  acgtacagtt  agttacgagc    780
ctaaagacac  aacgtgtttg  ttaattatac  tgtcgctgta  atatcttctc  ttccattatc    840
accggtcatt  ccttgcaggg  gcggtagtac  ccggagaccc  tgaactttc   ttttttttt     900 tgcgaaatta  aaaagttcat  tttcaattcg  acaatgagat  ctacaagcca  ttgttttatg    960
ttgatgagag  ccagcttaaa  gagttctcga  gatctcccga  gtttatcatt  atcaatactg   1020
ccatttcaaa  gaatacgtaa  ataattaata  gtagtgattt  tcctaacttt  atttagtcaa   1080
aaaattggcc  ttttaattct  gctgtaaccc  gtacatgccc  aaaatagggg  gcgggttaca   1140
cagaatatat  aacatcatag  gtgtctgggt  gaacagttta  ttcctggcat  ccactaaata   1200
taatggagcc  cgcttttttt  aagctggcat  ccagaaaaaa  aaagaatccc  agcaccaaaa   1260
tattgttttc  ttcaccaacc  atcagttcat  aggtccattc  tcttagcgca  actacacaga   1320 acagggcac   aaacaggcaa  aaacgggca   caacctcaat  ggagtgatgc  aacctgcttg   1380
gagtaaatga  tgacacaagg  caattgacct  acgcatgtat  ctatctcatt  tcttacacc    1440 ttctattacc  ttctgctctc  tctgatttgg  aaaaagctga  aaaaaaggt   tgaaaccagt   1500 tccctgaaat  tattccccta  tttgactaat  aagtatataa  agacggtagg  tattgattgt   1560
aattctgtaa  atctatttct  taaacttctt  aaattctact  tttatagtta  gtctttttt    1620 tagtttaaaa  caccaagaac  ttagtttcga  ataaacacac  ataaacaaac  aaatctagaa   1680
tgaagttcat  ttccactttc  ttgaccttca  ttttggctgc  tgtctctgtc  accgctgcat   1740
ctattccatc  tagtgcatct  gtacaattgg  actcctacaa  ttacgatggt  tccacatttt   1800
ccggcaagat  ttatgtcaaa  acatcgctt   actctaaaaa  ggttactgtt  gtgtacgcag   1860
acggttctga  caactggaac  aataacggca  acactattgc  tgcatcattt  tcaggcccaa   1920
tctctggatc  aaattacgaa  tactggacat  tctcagcatc  agtgaagggc  ataaaggagt   1980
tctacatcaa  atacgaagtt  tcaggtaaga  catattacga  caataacaac  tctgcaaact   2040
accaagtctc  aacttctaaa  cctactacaa  ctactgcagc  tacaaccaca  actacagctc   2100
catcaacttc  tacaacaacc  cgtccatcta  gttcagagcc  tgccaccttc  cctactggta   2160
attctaccat  cagctcttgg  atcaaaaagc  aggaagatat  ttccagattc  gctatgctta   2220
gaaacatcaa  cccacctggt  tctgccacag  ggtttatcgc  cgcatcactc  tctaccgctg   2280
gtccagatta  ctactacgcg  tggacaagag  atgccgcttt  gacatctaac  gttatcgttt   2340
acgaatacaa  caccacattg  tctgggaata  agacaattct  aaacgtactt  aaggattacg   2400
tcacattcag  tgttaagaca  cagtctactt  caacagtttg  taattgcctt  ggtgaaccaa   2460
agttcaatcc  agacggcagt  ggttacacag  gtgcttgggg  tagacctcaa  aatgatggtc   2520
ctgcagaaag  agcgactaca  tttgttctgt  ttgccgacag  ctacttgact  caaactaagg   2580
atgcctcata  cgtcactggt  acattaaagc  cagcaatttt  caaagatctc  gattacgttg   2640
ttaacgtctg  gagtaacgga  tgtttcgatt  tatgggagga  ggtgaacgga  gttcatttct   2700 acaccttat   ggttatgaga  aaagggctat  tgttggggc   tgatttcgcg  aagagaaacg   2760
gtgactcaac  tagagcctca  acttactctt  ctactgcttc  cacaattgct  aacaagatat   2820
caagtttctg  ggttagctca  aacaactggg  tgcaagtatc  ccaatctgtc  acaggaggtg   2880
taagtaaaaa  gggggttagac gttagcaccc  tgttagctgc  gaatctagga  tcagtcgatg   2940
```

```
atggattttt cactccaggt tctgaaaaga tattagctac agctgtggca gtcgaagatt    3000
cctttgccag tctataccca atcaacaaaa accttccatc atacttgggg aacgctattg    3060
gaagataccc tgaagataca tacaacggta atggtaactc acaaggcaat ccttggtttc    3120
tggcggttac cggctacgca gagttgtact atagagcaat taaggaatgg atttctaatg    3180
gaggcgttac agtgtcctct atctcattgc catttttcaa aaagttcgat agctctgcaa    3240
catccggtaa aaagtacacc gtaggtactt ctgacttcaa caatttagca caaaacattg    3300
ctcttgctgc agatcgtttc ctatctactg tacaactcca tgcaccaaac aatggttcat    3360
tagcagagga atttgataga caacaggtt tttctaccgg cgctagagat ttaacatggt    3420
cccacgcctc attgataaca gcatcctatg ccaaagccgg tgctccagct gcataattaa    3480
ttaaacaggc ccctttttcct tgtcgatat catgtaatta gttatgtcac gcttacattc    3540
acgccctcct cccacatccg ctctaaccga aaaggaagga gttagacaac ctgaagtcta    3600
ggtccctatt tatttttta tagttatgtt agtattaaga acgttattta tatttcaaat    3660
tttttctttt tttctgtaca aacgcgtgta cgcatgtaac gggcagacgg ccggccataa    3720
cttcgtataa tgtatgctat acgaagttat ggcaacggtt catcatctca tggatctgca    3780
catgaacaaa caccagagtc aaacgacgtt gaaattgagg ctactgcgcc aattgatgac    3840
aatacagacg atgataacaa accgaagtta tctgatgtag aaaaggatta gagatgctaa    3900
gagatagtga tgatatttca taaataatgt aattctatat atgttaatta ccttttttgc    3960
gaggcatatt tatggtgaag ataagttttt gaccatcaaa gaaggttaat gtggctgtgg    4020
tttcagggtc cataaagctt ttcaattcat cttttttttt tttgttcttt tttttgattc    4080
cggtttcttt gaaatttttt tgattcggta atctccgagc agaaggaaga acgaaggaag    4140
gagcacagac ttagattggt atatatacgc atatgtggtg ttgaagaaac atgaaattgc    4200
ccagtattct taacccaact gcacagaaca aaaacctgca ggaaacgaag ataaatcatg    4260
tcgaaagcta catataagga acgtgctgct actcatccta gtcctgttgc tgccaagcta    4320
tttaatatca tgcacgaaaa gcaaacaaac ttgtgtgctt cattggatgt tcgtaccacc    4380
aaggaattac tggagttagt tgaagcatta ggtcccaaaa tttgtttact aaaaacacat    4440
gtggatatct tgactgattt ttccatggag ggcacagtta agccgctaaa ggcattatcc    4500
gccaagtaca attttttact cttcgaagac agaaaatttg ctgacattgg taatacagtc    4560
aaattgcagt actctgcggg tgtatacaga atagcagaat gggcagacat tacgaatgca    4620
cacggtgtgg tgggcccagg tattgttagc ggtttgaagc aggcggcgga agaagtaaca    4680
aaggaaccta gaggcctttt gatgttagca gaattgtcat gcaagggctc cctagctact    4740
ggagaatata ctaagggtac tgttgacatt gcgaagagcg acaaagattt tgttatcggc    4800
tttattgctc aaagagacat gggtggaaga gatgaaggtt acgattggtt gattatgaca    4860
cgc                                                                  4863
```

<210> SEQ ID NO 16
<211> LENGTH: 4748
<212> TYPE: DNA
<213> ORGANISM: Artificial Sequence
<220> FEATURE:
<223> OTHER INFORMATION: Mfa2-Rhizopus oryzae GA integration construct

<400> SEQUENCE: 16

```
ggccgctcca tggagggcac agttaagccg ctaaaggcat tatccgccaa gtacaatttt      60
ttactcttcg aagacagaaa atttgctgac attggtaata cagtcaaatt gcagtactct     120
```

```
gcgggtgtat acagaatagc agaatgggca gacattacga atgcacacgg tgtggtgggc    180
ccaggtattg ttagcggttt gaagcaggcg gcggaagaag taacaaagga acctagaggc    240
cttttgatgt tagcagaatt gtcatgcaag ggctccctag ctactggaga atatactaag    300
ggtactgttg acattgcgaa gagcgacaaa gattttgtta tcggctttat tgctcaaaga    360
gacatgggtg aagagatga aggttacgat tggttgatta tgacacccgg tgtgggttta    420
gatgacaagg gagacgcatt gggtcaacag tatagaaccg tggatgatgt ggtctctaca    480
ggatctgaca ttattattgt tggaagagga ctatttgcaa agggaaggga tgctaaggta    540
gagggtgaac gttacagaaa agcaggctgg gaagcatatt tgagaagatg cggccagcaa    600
aactaaaaaa ctgtattata agtaaatgca tgtatactaa actcacaaat tagagcttca    660
atttaattat atcagttatt acccgggaat ctcggtcgta atgattttta taatgacgaa    720
aaaaaaaaaa ttggaaagaa aaagcttcat ggcctttata aaaaggaacc atccaatacc    780
tcgccagaac caagtaacag tattttacgg ggcacaaatc aagaacaata agacaggact    840
gtaaagatgg acgcattgaa ctccaaagaa caacaagagt tccaaaaagt agtggaacaa    900
aagcaaatga aggatttcat gcgtttgata acttcgtata atgtatgcta tacgaagtta    960
tctcgagggc cagaaaaagg aagtgtttcc ctccttcttg aattgatgtt accctcataa   1020
agcacgtggc ctcttatcga gaaagaaatt accgtcgctc gtgatttgtt tgcaaaaaga   1080
acaaaactga aaaaacccag acacgctcga cttcctgtct tcctgttgat tgcagcttcc   1140
aatttcgtca cacaacaagg tcctagcgac ggctcacagg ttttgtaaca agcaatcgaa   1200
ggttctggaa tggcgggaaa gggtttagta ccacatgcta tgatgcccac tgtgatctcc   1260
agagcaaagt tcgttcgatc gtactgttac tctctctctt tcaaacagaa ttgtccgaat   1320
cgtgtgacaa caacagcctg ttctcacaca ctcttttctt ctaaccaagg gggtggttta   1380
gtttagtaga acctcgtgaa acttacattt acatatatat aaacttgcat aaattggtca   1440
atgcaagaaa tacatatttg gtcttttcta attcgtagtt tttcaagttc ttagatgctt   1500 tcttttctc tttttttacag atcatcaagg aagtaattat ctacttttta caagtctaga   1560
atgaagttta tctccacgtt tttaaccttt atcctagcag ctgtcagcgt caccgccgca   1620
tcaattccga gttcagcatc tgtacaactt gactcttaca attacgatgg cagcactttc   1680
tcagggaaaa tttatgtgaa aaacatagca tatagtaaga aggttaccgt ggtatatgca   1740
gacggttctg ataattggaa taataatgga aacactattg ccgccagttt ttccggccca   1800
atttctggtt ccaattacga gtattggacc ttttctgcat cagtaaaagg catcaaggaa   1860
ttctatatta agtacgaagt ttcaggtaag acatattcg ataacaataa ctcagcaaat   1920
tatcaagtct ctacatctaa gcccacaaca acaactgctg ctaccaccac tacaaccgct   1980
ccttctacca gcaccactac cagaccaagc tctagtgaac cggctacctt tcctaccgga   2040
aacagtacca tctcaagctg gatcaaaaag caagaggaca taagtcgttt tgctatgttg   2100
aggaacatta atcctccagg atccgcgacc ggtttcattg cagcatcact aagtactgcc   2160
gggcctgatt attattatgc ttggactaga gacgctgcat taacatcaaa cgtgattgtt   2220
tatgaatata atacgaccct ttccggtaat aaaacgatct tgaacgtatt aaaagactat   2280
gtgaccttta gtgtgaagac ccaatctaca tctacagtgt gtaattgttt gggagaacct   2340
aaattcaatc cagacggttc tgggtacact ggtgcctggg gtagacctca aaacgacggt   2400
ccagcagaaa gagcaacaac ctttgttcta tttgctgact cttatttaac gcaaacaaag   2460
```

```
gacgcctcat atgttacagg gaccctaaaa ccagcaattt tcaaagactt ggattatgtt    2520
gttaatgttt ggagcaacgg atgttttgac ttgtgggagg aggttaacgg tgtacacttt    2580
tatacattga tggtgatgag aaaagggttg ctattgggag cagatttcgc taaaagaaat    2640
ggtgattcta caagagcgag cacatatagt agcaccgctt caacaatcgc caataaaatc    2700
tcatctttct gggtatctag caacaactgg gtacaagttt cccaaagtgt taccggcggt    2760
gtgtccaaaa agggtttaga cgttagcaca cttctagctg ctaatttggg tagcgttgat    2820
gacgggtttt ttactccagg tagtgagaag atactggcaa ccgcggtggc ggttaagac    2880 agctttgctt cattgtatcc tataaataaa aatctgccct cttatctggg taatgcaatt    2940
ggcagatacc cagaagatac ctacaatggt aatggtaatt cccaggggaa cccatggttt    3000
ttggctgtta caggctacgc agaactttat taccgtgcaa tcaaggaatg gatttcaaat    3060
ggcggcgtca ctgtcagtag tataagtttg ccctttttta agaaatttga ttcctcagca    3120
acgtctggta aaaatacac cgtaggtact agtgatttca ataatttggc ccaaaatatt    3180
gcgcttgctg ctgacaggtt tcttagtacc gttcagttgc acgctccaaa taatggctca    3240
ttggctgaag aatttgatcg tacgacaggt ttctccactg gtgctaggga tttgacttgg    3300
agtcatgcct cctaatcac agcaagctat gctaaagctg gtgcacctgc tgcttagtta    3360
attaatttac cagcttacta tccttcttga aaatatgcac tctatatctt ttagttctta    3420
attgcaacac atagatttgc tgtataacga attttatgct attttttaa tttggagttc    3480 ggtgatgaaa gtgtcacagc gaatttcctc acatgtaggg accgaattgt ttacaagttc    3540
tctgtaccac catggagaca tcaaagattg aaaatctatg gaaagatatg acggtagca    3600 acaagaatat agcacgagcc gcggagttca tttcgttact tttgatatcg ctcacaacta    3660
ttgcgaagcg cttcagtgaa aaaatcataa ggaaaagttg taaatattat tggtagtatt    3720
cgtttggtaa agtagagggg gtaattttc ccctttattt tgttcataca ttcttaaatt    3780
gctttgcctc tcctttttgga aagctatact tcggagcact gttgagcgaa ggctcaggcc    3840
ggcagcacgc agcacgctgt atttacgtat ttaattttat atatttgtgc atacactact    3900
agggaagact tgaaaaaaac ctaggaaatg aaaaaacgac acaggaagtc ccgtatttac    3960 tatttttttcc ttcctttga tgggcaggg cggaaataga ggataggata agcctactgc    4020
ttagctgttt ccgtctctac ttcggtagtt gtctcaattg tcgtttcagt attaccttta    4080
gagccgctag acgatggttg agctatttgt tgagggaaaa ctaagttcat gtaacacacg    4140
cataacccga ttaaactcat gaatagcttg attgcaggag gctggtccat tggagatggt    4200
gccttatttt ccttataggc aacgatgatg tcttcgtcgg tgttcaggta gtagtgtaca    4260
ctctgaatca gggagaacca ggcaatgaac ttgttcctca agaaaatagc ggccataggc    4320
atggattggt taaccacacc agatatgctt ggtgtggcag aatatagtcc ttttggtggc    4380
gcaattttct tgtacctgtg gtagaaaggg agcggttgaa ctgttagtat atattggcaa    4440
tatcagcaaa tttgaaagaa aattgtcggt gaaaaacata cgaaacacaa aggtcgggcc    4500
ttgcaacgtt attcaaagtc attgtttagt tgaggaggta gcagcggagt atatgtattc    4560 ctttttttg cctatggatg ttgtaccatg cccattctgc tcaagctttt gttaaaatta    4620
tttttcagta ttttttcttc catgttgcgc gttacgagaa cagaagcgac agataaccgc    4680
aatcatacaa ctagcgctac tgcggggtgt aaaaagcaca agaactaagc caagatcaca    4740
acagttat                                                              4748
```

<210> SEQ ID NO 17
<211> LENGTH: 1674
<212> TYPE: DNA
<213> ORGANISM: Artificial Sequence
<220> FEATURE:
<223> OTHER INFORMATION: Integration construct

<400> SEQUENCE: 17

```
ctaaattcgg ccttgctcag agactcctgg attttggcta acaacgcagt cccttcgatg      60
catatagcta ggccacaaat tatgccaata acggtccatg ggttgatgtt ttcttgaatt     120
ctttcgtttt tcatgctatt tgcgtcttcc caagtcccag cgttccagta ttcatactgc     180
gcgttagagt ggtagccata agagccggca tattggtaat tttcagtatt aacgttagaa     240
cgtggtgaat acgatgtggt ccagccttgc ctcgttgtgt catatacgat cttttctttt     300
gggtcacaaa gaatatcata tgcttgagag atgactttaa atctatgtag tttttcgctt     360
gatgttagca gcagcggtga tttactatca ctgttggtaa ccttttctga gctaaatatt     420
tgaatgttat cggaatggtc agggtggtac aattttacat aacgatgata tttttttttt     480
aacgacttct tgtccagttt aggatttcca gatccggcct ttggaatgcc aaaaatatca     540
tagggagttg gatctgccaa ctcaggccat tgttcatccc ttatcgtaag ttttctattg     600
ccatttttat cgttcgctgt agcatactta gctataaaag tgatttgtgg gggacacttt     660
tctacacatg ataagtgcca cttgaataaa aatgggtata cgaacttatg gtgtagcata     720
acaaatatat tgcaagtagt gacctatggt gtgtagatat acgtacagtt agttacgagc     780
ctaaagacac aacgtgtttg ttaattatac tgtcgctgta atatcttctc ttccattatc     840
accggtcatt ccttgcaggg gcggtagtac ccggagaccc tgaactttc tttttttttt      900
tgcgaaatta aaaagttcat tttcaattcg acaatgagat ctacaagcca ttgttttatg     960
ttgatgagag ccagcttaaa gagttctcga gatctcccga gtttatcatt atcaatactg    1020
ccatttcaaa gaatacgtaa ataattaata gtagtgattt tcctaacttt atttagtcaa    1080
aaaattggcc ttttaattct gctgtaaccc gtacatgccc aaaatagggg gcgggttaca    1140
cagaatatat aacatcatag gtgtctgggt gaacagttta ttcctggcat ccactaaata    1200
taatggagcc cgcttttttt aagctggcat ccagaaaaaa aagaatccc agcaccaaaa     1260
tattgttttc ttcaccaacc atcagttcat aggtccattc tcttagcgca actacacaga    1320
acagggggcac aaacaggcaa aaaacgggca caacctcaat ggagtgatgc aacctgcttg    1380
gagtaaatga tgacacaagg caattgacct acgcatgtat ctatctcatt ttcttcacacc   1440
ttctattacc ttctgctctc tctgatttgg aaaaagctga aaaaaaaggt tgaaaccagt    1500
tccctgaaat tattccccta tttgactaat aagtatataa agacggtagg tattgattgt    1560
aattctgtaa atctatttct taaacttctt aaattctact tttatagtta gtcttttttt    1620
tagtttaaaa caccaagaac ttagtttcga ataaacacac ataaacaaac aaat          1674
```

<210> SEQ ID NO 18
<211> LENGTH: 4260
<212> TYPE: DNA
<213> ORGANISM: Artificial Sequence
<220> FEATURE:
<223> OTHER INFORMATION: Mfa2-Rhizopus oryzae integration construct

<400> SEQUENCE: 18

```
tcgagatctc ccgagtttat cattatcaat actgccattt caagaatac gtaaataatt       60
aatagtagtg attttcctaa ctttatttag tcaaaaaatt ggccttttaa ttctgctgta     120
```

```
acccgtacat gcccaaaata gggggcgggt tacacagaat atataacatc ataggtgtct    180
gggtgaacag tttattcctg gcatccacta aatataatgg agcccgcttt ttttaagctg    240
gcatccagaa aaaaaagaa tcccagcacc aaaatattgt tttcttcacc aaccatcagt    300
tcataggtcc attctcttag cgcaactaca cagaacaggg gcacaaacag caaaaaacg    360 ggcacaacct caatggagtg atgcaacctg cttggagtaa atgatgacac aaggcaattg    420
acctacgcat gtatctatct cattttctta caccttctat taccttctgc tctctctgat    480
ttggaaaaag ctgaaaaaaa aggttgaaac cagttccctg aaattattcc cctatttgac    540
taataagtat ataagacgg taggtattga ttgtaattct gtaaatctat ttcttaaact    600
tcttaaattc tacttttata gttagtcttt tttttagttt aaaacaccaa gaacttagtt    660
tcgaataaac acacataaac aaacaaatct agaatgaagt tcatttccac tttcttgacc    720
ttcattttgg ctgctgtctc tgtcaccgct gcatctattc catctagtgc atctgtacaa    780
ttggactcct acaattacga tggttccaca ttttccggca agatttatgt caaaaacatc    840
gcttactcta aaaaggttac tgttgtgtac gcagacggtt ctgacaactg gaacaataac    900
ggcaacacta ttgctgcatc attttcaggc ccaatctctg gatcaaatta cgaatactgg    960
acattctcag catcagtgaa gggcataaag gagttctaca tcaaatacga agtttcaggt   1020
aagacatatt cgacaataa caactctgca aactaccaag tctcaacttc taaacctact   1080
acaactactg cagctacaac cacaactaca gctccatcaa cttctacaac aacccgtcca   1140
tctagttcag agcctgccac cttccctact ggtaattcta ccatcagctc ttggatcaaa   1200
aagcaggaag atatttccag attcgctatg cttagaaaca tcaacccacc tggttctgcc   1260
acagggttta tcgccgcatc actctctacc gctggtccag attactacta cgcgtggaca   1320
agagatgccg ctttgacatc taacgttatc gtttacgaat acaacaccac attgtctggg   1380
aataagacaa ttctaaacgt acttaaggat tacgtcacat tcagtgttaa gacacagtct   1440
acttcaacag tttgtaattg ccttggtgaa ccaaagttca atccagacgg cagtggttac   1500
acaggtgctt ggggtagacc tcaaaatgat ggtcctgcag aaagagcgac tacatttgtt   1560
ctgtttgccg acagctactt gactcaaact aaggatgcct catacgtcac tggtacatta   1620
aagccagcaa ttttcaaaga tctcgattac gttgttaacg tctggagtaa cggatgtttc   1680
gatttatggg aggaggtgaa cggagttcat ttctacaccc ttatggttat gagaaagggg   1740
ctattgttgg gggctgattt cgcgaagaga aacggtgact caactagagc ctcaacttac   1800
tcttctactg cttccacaat tgctaacaag atatcaagtt tctgggttag ctcaaacaac   1860
tgggtgcaag tatcccaatc tgtcacagga ggtgtaagta aaaaggggtt agacgttagc   1920
accctgttag ctgcgaatct aggatcagtc gatgatggat ttttcactcc aggttctgaa   1980
aagatattag ctacagctgt ggcagtcgaa gattcctttg ccagtctata cccaatcaac   2040
aaaaaccttc catcatactt ggggaacgct attggaagat accctgaaga tacatacaac   2100
ggtaatggta actcacaagg caatccttgg tttctggcgg ttaccggcta cgcagagttg   2160
tactatagag caattaagga atggatttct aatggaggcg ttacagtgtc ctctatctca   2220
ttgccatttt tcaaaagtt cgatagctct gcaacatccg gtaaaagta caccgtaggt   2280 acttctgact tcaacaattt agcacaaaac attgctcttg ctgcagatcg tttcctatct   2340
actgtacaac tccatgcacc aaacaatggt tcattagcag aggaatttga tagaacaaca   2400
ggtttttcta ccggcgctag agatttaaca tggtcccacg cctcattgat aacagcatcc   2460
tatgccaaag ccggtgctcc agctgcataa ttaattaaac aggcccctttt tcctttgtcg   2520
```

```
atatcatgta attagttatg tcacgcttac attcacgccc tcctcccaca tccgctctaa    2580
ccgaaaagga aggagttaga caacctgaag tctaggtccc tatttatttt tttatagtta    2640
tgttagtatt aagaacgtta tttatatttc aaattttttct ttttttttctg tacaaacgcg   2700
```

Actual:
```
atatcatgta attagttatg tcacgcttac attcacgccc tcctcccaca tccgctctaa    2580
ccgaaaagga aggagttaga caacctgaag tctaggtccc tatttatttt tttatagtta    2640
tgttagtatt aagaacgtta tttatatttc aaattttttct tttttttctg tacaaacgcg    2700
tgtacgcatg taacgggcag acggccggcc ataacttcgt ataatgtatg ctatacgaag    2760
ttatccttac atcacaccca atccccaca agtgatcccc cacacaccat agcttcaaaa    2820
tgtttctact cctttttttac tcttccagat tttctcggac tccgcgcatc gccgtaccac    2880
ttcaaaacac ccaagcacag catactaaat ttcccctctt tcttcctcta gggtggcgtt    2940
aattacccgt actaaaggtt tggaaaagaa aaaagagacc gcctcgtttc ttttttcttcg    3000 tcgaaaaagg caataaaaat tttatcacg tttcttttc ttgaaaaatt ttttttttga    3060
tttttttctc tttcgatgac ctcccattga tatttaagtt aataaatggt cttcaatttc    3120
tcaagtttca gtttcgtttt tcttgttcta ttacaacttt ttttacttct tgctcattag    3180
aaagaaagca tagcaatcta atctaagttt taattacaaa atgccacaat cctgggaaga    3240
attggccgcc gacaaacgtg cccgtttggc taaaaccatt cctgacgaat ggaaggttca    3300
aactttgcct gccgaagatt ccgttattga tttcccaaag aagtccggta ttttgtctga    3360
ggctgaattg aagattaccg aagcctctgc tgctgatttg gtctccaagt tggccgctgg    3420
tgagttgact tctgttgaag tcactttggc tttttgtaag agagctgcta ttgctcaaca    3480
attaaccaac tgtgctcacg aattcttccc agatgctgct ttagctcaag ctagagaatt    3540
agatgaatac tacgctaagc ataagagacc agttggtcca ttacacggtt taccaatctc    3600
tttaaaggac caattgcgtg ttaagggtta cgaaacctcc atgggttaca tttcctggtt    3660
aaacaaatac gatgaaggtg attccgtctt aaccaccatg ttgagaaaag ctggtgctgt    3720
tttctacgtt aagacctctg tcccacaaac cttgatggtc tgtgaaaccg tcaacaacat    3780
cattggtaga actgtcaatc caagaaacaa aaattggtcc tgtggtggtt cttctggtgg    3840
tgaaggtgct attgttggta ttagaggtgg tgttattggt gtcggtactg acattggtgg    3900
ttccattaga gtcccagctg ctttcaactt tttatacggt ttgagaccat ctcacgtag    3960 attgccatat gctaaaatgg ctaactctat ggaaggtcaa gaaaccgttc actccgtcgt    4020
tggtcctatc actcactccg tcgaagactt gagattgttc accaaatctg tctctgggtca    4080 agaaccttgg aagtacgact ctaaggtcat ccccatgcca tggagacaat ctgaatctga    4140
catcattgcc tctaagatta agaatggtgg tttgaacatt ggttattaca atttcgacgg    4200
taacgtcttg ccacacccac caattttacg tggtgtcgaa actaccgttg ccgctttggc    4260
```

<210> SEQ ID NO 19
<211> LENGTH: 5008
<212> TYPE: DNA
<213> ORGANISM: Artificial Sequence
<220> FEATURE:
<223> OTHER INFORMATION: Mfa2-Rhizopus oryzae GA integration construct

<400> SEQUENCE: 19

```
ggccgcgaag gtgctattgt tggtattaga ggtggtgtta ttggtgtcgg tactgacatt      60
ggtggttcca ttagagtccc agctgctttc aacttttttat acggtttgag accatctcac    120
ggtagattgc catatgctaa aatggctaac tctatggaag gtcaagaaac cgttcactcc    180
gtcgttggtc ctatcactca ctccgtcgaa gacttgagat gttcaccaa atctgtcttg    240 ggtcaagaac cttggaagta cgactctaag gtcatcccca tgccatggag acaatctgaa    300
```

```
tctgacatca ttgcctctaa gattaagaat ggtggtttga acattggtta ttacaatttc    360
gacggtaacg tcttgccaca cccaccaatt ttacgtggtg tcgaaactac cgttgccgct    420
ttggccaagg ctggtcacac cgttactcca tggactccat acaagcatga tttcggtcat    480
gacttgattt cccacatcta tgctgctgat ggttctgccg acgtcatgag agacatttct    540
gcctctggtg agccagccat ccctaacatt aaggacttgt tgaacccaaa tattaaggct    600
gttaacatga acgaattgtg ggacactcat ttacaaaagt ggaactatca aatggaatac    660
ttggaaaagt ggcgtgaagc tgaagaaaaa gctggtaagg aattggacgc tattatcgct    720
ccaattactc ctaccgccgc tgtcagacac gatcaattca gatactacgg ttacgcctcc    780
gttattaact tattggattt cacctctgtt gtcgtcccag tcactttcgc tgataagaat    840
attgataaga gaacgaatcc ttttaaagct gtttccgaat ggatgctttt ggttcaagaa    900
gaatacgacc cagaggctta tcacggtgct cctgttgctg ttcaagttat tggtagaaga    960
ttgtccgaag agaactttt ggctatcgcc gaagaagtcg gtaaattgtt gggtaacgtc   1020
gtcactccat aagcgaattt cttatgattt atgattttta ttattaaata agttataaaa   1080
aaaataagtg tatacaaatt ttaaagtgac tcttaggttt taaaacgaaa attcttattc   1140
ttgagtaact ctttcctgta ggtcaggttg ctttctcagg tatagcatga ggtcgctctt   1200
attgaccaca cctctaccgg catgccgagc aaatgcctgc aaatcgctcc ccatttcacc   1260
caattgtaga tatgctaact ccagcaatga gttgatgaat ctcggtgtgt attttatgtc   1320
ctcagaggac aacacataac ttcgtataat gtatgctata cgaagttatc tcgagggcca   1380 gaaaaggaa gtgtttccct ccttcttgaa ttgatgttac cctcataaag cacgtggcct   1440
cttatcgaga aagaaattac cgtcgctcgt gatttgtttg caaaagaac aaaactgaaa   1500 aaacccagac acgctcgact tcctgtcttc ctgttgattg cagcttccaa tttcgtcaca   1560
caacaaggtc ctagcgacgg ctcacaggtt ttgtaacaag caatcgaagg ttctggaatg   1620
gcgggaaagg gtttagtacc acatgctatg atgcccactg tgatctccag agcaaagttc   1680
gttcgatcgt actgttactc tctctctttc aaacagaatt gtccgaatcg tgtgacaaca   1740
acagcctgtt ctcacacact cttttcttct aaccaagggg gtggtttagt ttagtagaac   1800
ctcgtgaaac ttacatttac atatatataa acttgcataa attggtcaat gcaagaaata   1860
catatttggt cttttctaat tcgtagtttt tcaagttctt agatgctttc ttttttctctt   1920 ttttacagat catcaaggaa gtaattatct acttttttaca agtctagaat gaagtttatc   1980
tccacgtttt taacctttat cctagcagct gtcagcgtca ccgccgcatc aattccgagt   2040
tcagcatctg tacaacttga ctcttacaat tacgatggca gcactttctc agggaaaatt   2100
tatgtgaaaa acatagcata tagtaagaag gttaccgtgg tatatgcaga cggttctgat   2160
aattggaata ataatggaaa cactattgcc gccagttttt ccggcccaat ttctggttcc   2220
aattacgagt attggacctt ttctgcatca gtaaaaggca tcaaggaatt ctatattaag   2280
tacgaagttt caggtaagac atattacgat aacaataact cagcaaatta tcaagtctct   2340
acatctaagc ccacaacaac aactgctgct accaccacta caaccgctcc ttctaccagc   2400
accactacca gaccaagctc tagtgaaccg gctacctttc ctaccggaaa cagtaccatc   2460
tcaagctgga tcaaaaagca agaggacata agtcgttttg ctatgttgag gaacattaat   2520
cctccaggat ccgcgaccgg tttcattgca gcatcactaa gtactgccgg gcctgattat   2580
tattatgctt ggactagaga cgctgcatta acatcaaacg tgattgttta tgaatataat   2640
acgacccttt ccggtaataa aacgatcttg aacgtattaa aagactatgt gacctttagt   2700
```

```
gtgaagaccc aatctacatc tacagtgtgt aattgtttgg gagaacctaa attcaatcca   2760
gacggttctg ggtacactgg tgcctggggt agacctcaaa cgacggtcc agcagaaaga    2820 gcaacaacct ttgttctatt tgctgactct tatttaacgc aaacaaagga cgcctcatat   2880
gttacaggga ccctaaaacc agcaattttc aaagacttgg attatgttgt taatgtttgg   2940
agcaacggat gttttgactt gtgggaggag gttaacggtg tacactttta tacattgatg   3000
gtgatgagaa aagggttgct attgggagca gatttcgcta aaagaaatgg tgattctaca   3060
agagcgagca catatagtag caccgcttca acaatcgcca ataaaatctc atctttctgg   3120
gtatctagca caactgggt acaagtttcc caaagtgtta ccggcggtgt gtccaaaaag    3180
ggtttagacg ttagcacact tctagctgct aatttgggta gcgttgatga cgggtttttt   3240
actccaggta gtgagaagat actggcaacc gcggtggcgg ttgaagacag ctttgcttca   3300
ttgtatccta taaataaaaa tctgccctct tatctgggta atgcaattgg cagatacca    3360 gaagatacct acaatggtaa tggtaattcc caggggaacc catggttttt ggctgttaca   3420
ggctacgcag aactttatta ccgtgcaatc aaggaatgga tttcaaatgg cggcgtcact   3480
gtcagtagta taagtttgcc cttttttaag aaatttgatt cctcagcaac gtctggtaaa   3540
aaatacaccg taggtactag tgatttcaat aatttggccc aaaatattgc gcttgctgct   3600
gacaggtttc ttagtaccgt tcagttgcac gctccaaata atggctcatt ggctgaagaa   3660
tttgatcgta cgacaggttt ctccactggt gctagggatt tgacttggag tcatgcctcc   3720
ttaatcacag caagctatgc taaagctggt gcacctgctg cttagttaat taatttacca   3780
gcttactatc cttcttgaaa atatgcactc tatatctttt agttcttaat tgcaacacat   3840
agatttgctg tataacgaat tttatgctat tttttttaatt tggagttcgg tgatgaaagt   3900
gtcacagcga atttcctcac atgtagggac cgaattgttt acaagttctc tgtaccacca   3960
tggagacatc aaagattgaa aatctatgga aagatatgga cggtagcaac aagaatatag   4020
cacgagccgc ggagttcatt tcgttacttt tgatatcgct cacaactatt gcgaagcgct   4080
tcagtgaaaa aatcataagg aaagttgta aatattattg gtagtattcg tttggtaaag    4140 tagaggggt aattttccc ctttattttg ttcatacatt cttaaattgc tttgcctctc      4200
cttttggaaa gctatacttc ggagcactgt tgagcgaagg ctcaggccgg cagcacgcag   4260
cacgctgtat ttacgtattt aatttatat atttgtgcat acactactag ggaagacttg    4320
aaaaaaacct aggaaatgaa aaaacgacac aggaagtccc gtatttacta ttttttcctt   4380 cctttttgatg gggcagggcg gaaatagagg ataggataag cctactgctt agctgttttcc  4440 gtctctactt cggtagttgt ctcaattgtc gtttcagtat taccttttaga gccgctagac   4500 gatggttgag ctatttgttg agggaaaact aagttcatgt aacacacgca taccccgatt    4560
aaactcatga atagcttgat tgcaggaggc tggtccattg gagatggtgc cttatttttcc  4620 ttataggcaa cgatgatgtc ttcgtcggtc ttcaggtagt agtgtacact ctgaatcagg   4680
gagaaccagg caatgaactt gttcctcaag aaaatagcgg ccataggcat ggattggtta   4740
accacaccag atatgcttgg tgtggcagaa tatagtcctt ttggtggcgc aattttcttg   4800
tacctgtggt agaaagggag cggttgaact gttagtatat attggcaata tcagcaaatt   4860
tgaaagaaaa ttgtcggtga aaaacatacg aaacacaaag gtcgggcctt gcaacgttat   4920
tcaaagtcat tgtttagttg aggaggtagc agcggagtat atgtattcct ttttttttgcc  4980 tatggatgtt gtaccatgcc cattctga                                       5008
```

<210> SEQ ID NO 20
<211> LENGTH: 4884
<212> TYPE: DNA
<213> ORGANISM: Artificial Sequence
<220> FEATURE:
<223> OTHER INFORMATION: Rhizopus microsporus GA integration construct

<400> SEQUENCE: 20

```
ctaaattcgg ccttgctcag agactcctgg attttggcta acaacgcagt cccttcgatg      60
catatagcta ggccacaaat tatgccaata acggtccatg ggttgatgtt ttcttgaatt     120
ctttcgtttt tcatgctatt tgcgtcttcc caagtcccag cgttccagta ttcatactgc     180
gcgttagagt ggtagccata agagccggca tattggtaat tttcagtatt aacgttagaa     240
cgtggtgaat acgatgtggt ccagccttgc ctcgttgtgt catatacgat ctttttcttt     300
gggtcacaaa gaatatcata tgcttgagag atgactttaa atctatgtag ttttttcgctt    360
gatgttagca gcagcggtga tttactatca ctgttggtaa ccttttctga gctaaatatt     420
tgaatgttat cggaatggtc agggtggtac aattttacat aacgatgata ttttttttt     480
aacgacttct tgtccagttt aggatttcca gatccggcct ttggaatgcc aaaaatatca     540
tagggagttg gatctgccaa ctcaggccat tgttcatccc ttatcgtaag ttttctattg     600
ccattttat cgttcgctgt agcatactta gctataaaag tgatttgtgg gggacacttt     660
tctacacatg ataagtgcca cttgaataaa atgggtata cgaacttatg gtgtagcata     720
acaaatatat tgcaagtagt gacctatggt gtgtagatat acgtacagtt agttacgagc     780
ctaaagacac aacgtgtttg ttaattatac tgtcgctgta atatcttctc ttccattatc     840
accggtcatt ccttgcaggg gcggtagtac ccggagaccc tgaacttttc ttttttttt     900
tgcgaaatta aaaagttcat tttcaattcg acaatgagat ctacaagcca ttgttttatg    960
ttgatgagag ccagcttaaa gagttctcga gatctcccga gtttatcatt atcaatactg   1020
ccatttcaaa gaatacgtaa ataattaata gtagtgattt tcctaacttt atttagtcaa   1080
aaaattggcc ttttaattct gctgtaaccc gtacatgccc aaaatagggg gcgggttaca   1140
cagaatatat aacatcatag gtgtctgggt gaacagttta ttcctggcat ccactaaata   1200
taatggagcc cgctttttt aagctggcat ccagaaaaaa aagaatccc agcaccaaaa    1260
tattgttttc ttcaccaacc atcagttcat aggtccattc tcttagcgca actacacaga   1320
acagggcac aaacaggcaa aaacgggca caacctcaat ggagtgatgc aacctgcttg   1380
gagtaaatga tgacacaagg caattgacct acgcatgtat ctatctcatt ttcttacacc   1440
ttctattacc ttctgctctc tctgatttgg aaaaagctga aaaaaaggt tgaaaccagt   1500
tccctgaaat tattccccta tttgactaat aagtatataa agacggtagg tattgattgt   1560
aattctgtaa atctatttct taaacttctt aaattctact tttatagtta gtcttttttt   1620
tagtttaaaa caccaagaac ttagtttcga ataacacac ataaacaaac aaatctagaa   1680
tgaaacttat gaatccatct atgaaggcat acgttttctt tatcttaagc tacttctctt   1740
tactcgttag ctcagctgcg gtgccaacct ctgccgccgt acaagttgag tcatacaatt   1800
atgacggtac cacttttca ggtagaatat tcgtcaaaaa cattgcctac tcaaaggtcg   1860
taacagttat ctactccgat ggatcagata actggaacaa taacaacaac aaagtttctg   1920
cagcttactc agaagcaatt tctgggtcta actacgaata ctggacattc tccgcaaagt   1980
tatccggaat taaacagttt tatgtcaaat acgaagtttc tggttcaaca tattacgaca   2040
acaacggtac caaaaactac caagtccaag caacctcagc gacatctaca acagctactg   2100
```

```
caaccacaac tacagctact ggcacaacaa ctacttctac aggtccaact agtactgcat    2160
ccgtatcatt ccctaccggt aactcaacaa tttcttcctg gataaaaaat caagaggaaa    2220
tcagccgttt tgctatgttg agaaatatca atccacctgg gtctgccaca gggttcatag    2280
ccgcatctct gtccacagcc ggcccagatt actattactc ttggactaga gattcagcac    2340
taacagctaa tgtgatcgct tacgaataca acacaacatt cactggaaac accacccttc    2400
ttaagtactt gaaagattac gttacatttt ctgtcaaaag ccaatctgta tctaccgttt    2460
gtaactgtct gggagaacca aagttcaacg ctgatggtag ttcttttaca ggtccatggg    2520
gcagaccaca aaacgacgga ccagcagaga gagctgttac ttttatgttg attgctgaca    2580
gctacttgac tcaaactaag gacgcatcct acgttaccgg tacattaaag ccagcaatct    2640
tcaaagatct tgattacgta gtttctgttt ggtctaacgg ttgctacgat ttatgggaag    2700
aggttaatgg tgttcatttc tatactctca tggtcatgag aaagggtttg atcttaggtg    2760
ccgacttcgc tgctagaaat ggtgactcta gtagagcttc aacctacaag caaactgcat    2820
caacaatgga atcaaagatc agttcttttt ggtcagattc taacaactac gtccaagttt    2880
ctcaatcagt taccgccgga gtgtcaaaaa agggactaga tgttagtaca ctattggcgg    2940
ccaacattgg tagtctgcct gatggctttt tcactccagg ctccgaaaag atattggcta    3000
cagcagtggc gttagaaaat gcattcgcat ccttgtaccc aattaactct aacctacctt    3060
cttacttggg taactcaatt ggaagatatc ctgaggatac atacaacggt aatggcaact    3120
ctcaggggaa tccatggttc cttgccgtca acgcatacgc agaactttac tacagagcta    3180
ttaaggaatg gattagtaat ggcaaggtga cagtatccaa tatctcacta cctttcttca    3240
aaaagtttga ttcttccgcc acttctggaa agacatacac tgctggtaca tcagatttca    3300
ataacttggc tcagaacatt gctttaggcg ccgatagatt cctgtctact gttaagttcc    3360
acgcatacac taacgggagt ctatcagaag agtacgatag atctaccggt atgagtactg    3420
gggctcgtga tttaacatgg tcccatgctt cattgatcac agtggcgtac gcaaaggccg    3480
gtagtcctgc agcttagtta attaaacagg ccccttttcc tttgtcgata tcatgtaatt    3540
agttatgtca cgcttacatt cacgccctcc tcccacatcc gctctaaccg aaaaggaagg    3600
agttagacaa cctgaagtct aggtccctat ttattttttt atagttatgt tagtattaag    3660
aacgttattt atatttcaaa tttttctttt ttttctgtac aaacgcgtgt acgcatgtaa    3720
cgggcagacg gccggccata acttcgtata atgtatgcta tacgaagtta tggcaacggt    3780
tcatcatctc atggatctgc acatgaacaa acaccagagt caaacgacgt tgaaattgag    3840
gctactgcgc caattgatga caatacagac gatgataaca aaccgaagtt atctgatgta    3900
gaaaaggatt agagatgcta agagatagtg atgatatttc ataaataatg taattctata    3960
tatgttaatt accttttttg cgaggcatat ttatggtgaa ggataagttt tgaccatcaa    4020
agaaggttaa tgtggctgtg gtttcagggt ccataaagct tttcaattca tctttttttt    4080
ttttgttctt ttttttgatt ccggtttctt tgaaatttt ttgattcggt aatctccgag    4140
cagaaggaag aacgaaggaa ggagcacaga cttagattgg tatatatacg catatgtggt    4200
gttgaagaaa catgaaattg cccagtattc ttaacccaac tgcacagaac aaaaacctgc    4260
aggaaacgaa gataaatcat gtcgaaagct acatataagg aacgtgctgc tactcatcct    4320
agtcctgttg ctgccaagct atttaatatc atgcacgaaa agcaaacaaa cttgtgtgct    4380
tcattggatg ttcgtaccac caaggaatta ctggagttag ttgaagcatt aggtcccaaa    4440
```

```
atttgtttac taaaaacaca tgtggatatc ttgactgatt tttccatgga gggcacagtt    4500
aagccgctaa aggcattatc cgccaagtac aattttttac tcttcgaaga cagaaaattt    4560
gctgacattg gtaatacagt caaattgcag tactctgcgg gtgtatacag aatagcagaa    4620
tgggcagaca ttacgaatgc acacggtgtg gtgggcccag gtattgttag cggtttgaag    4680
caggcggcgg aagaagtaac aaaggaacct agaggccttt tgatgttagc agaattgtca    4740
tgcaagggct ccctagctac tggagaatat actaagggta ctgttgacat tgcgaagagc    4800
gacaaagatt ttgttatcgg ctttattgct caaagagaca tgggtggaag agatgaaggt    4860
tacgattggt tgattatgac acgc                                           4884
```

<210> SEQ ID NO 21
<211> LENGTH: 1790
<212> TYPE: DNA
<213> ORGANISM: Artificial Sequence
<220> FEATURE:
<223> OTHER INFORMATION: Integration construct

<400> SEQUENCE: 21

```
ggaagagctc ctactgcgcc aattgatgac aatacagacg atgataacaa accgaagtta      60
tctgatgtag aaaaggatta gagatgctaa gagatagtga tgatatttca taataatgt     120 aattctatat atgttaatta cctttttgc gaggcatatt tatggtgaag ataagtttt      180 gaccatcaaa gaaggttaat gtggctgtgg tttcagggtc cataaagctt ttcaattcat    240
cttttttttt ttgttctttt ttttgattcc ggtttctttg aaatttttt gattcggtaa     300 tctccgagca gaaggaagaa cgaaggaagg agcacagact tagattggta tatatacgca    360
tatgtggtgt tgaagaaaca tgaaattgcc cagtattctt aacccaactg cacagaacaa    420
aaacctgcag gaaacgaaga taatcatgt cgaaagctac atataaggaa cgtgctgcta     480
ctcatcctag tcctgttgct gccaagctat ttaatatcat gcacgaaaag caaacaaact    540
tgtgtgcttc attggatgtt cgtaccacca ggaattact ggagttagtt gaagcattag     600
gtcccaaaat tgtttacta aaaacacatg tggatatctt gactgatttt tccatggagg     660
gcacagttaa gccgctaaag gcattatccg ccaagtacaa ttttttactc ttcgaagaca    720
gaaaatttgc tgacattggt aatacagtca aattgcagta ctctgcgggt gtatacagaa    780
tagcagaatg gcagacatt acgaatgcgc acggtgtggt gggcccaggt attgttagcg     840
gtttgaagca ggcggcggaa gaagtaacaa aggaacctag aggcctttg atgttagcag     900 aattgtcatg caagggctcc ctagctactg gagaatatac taagggtact gttgacattg    960
cgaagagcga caaagatttt gttatcggct ttattgctca aagagacatg ggtggaagag   1020
atgaaggtta cgattggttg attatgacac ccggtgtggg tttagatgac aagggagacg   1080
cattgggtca acagtataga gccgtggatg atgtggtctc tacaggatct gacattatta   1140
ttgttggaag aggactattt gcaagggaa gggatgctaa ggtagagggt gaacgttaca    1200
gaaaagcagg ctgggaagca tatttgagaa gatgcggcca gcaaaactaa aaaactgtat   1260
tataagtaaa tgcatgtata ctaaactcac aaattagagc ttcaatttaa ttatatcagt   1320
tattacccgg gaatctccgt cgtaatgatt tttataatga cgaaaaaaaa aaattggaaa   1380
gaaaaagctt catggccttt ataaaaagga accatccaat acctcgccag aaccaagtaa   1440
cagtatttta cggggcacaa atcaagaaca ataagacagg actgtaaaga tggacgcatt   1500
gaactccaaa gaacaacaag agttccaaaa agtagtggaa caaaagcaaa tgaaggattt   1560
catgcgtttg ataacttcgt ataatgtatg ctatacgaag ttatgcggcc gccagcacgc   1620
```

```
agcacgctgt atttacgtat ttaattttat atatttgtgc atacactact agggaagact      1680
tgaaaaaaac ctaggaaatg aaaaaacgac acaggaagtc ccgtatttac tattttttcc      1740
ttccttttga tggggcaggg cggaaataga ggataggata agcctactgc                 1790

<210> SEQ ID NO 22
<211> LENGTH: 4474
<212> TYPE: DNA
<213> ORGANISM: Artificial Sequence
<220> FEATURE:
<223> OTHER INFORMATION: Rhizopus microsporus GA integration construct

<400> SEQUENCE: 22
gtgtttgtta attatactgt cgctgtaata tcttctcttc cattatcacc ggtcattcct        60
tgcaggggcg gtagtacccg agaccctga acttttcttt ttttttttgc gaaattaaaa       120
agttcatttt caattcgaca atgagatcta caagccattg ttttatgttg atgagagcca       180
gcttaaagag ttctcgagat ctcccgagtt tatcattatc aatactgcca tttcaaagaa       240
tacgtaaata attaatagta gtgattttcc taactttatt tagtcaaaaa attggccttt       300
taattctgct gtaacccgta catgcccaaa atagggggcg ggttacacag aatatataac       360
atcataggtg tctgggtgaa cagtttattc ctggcatcca ctaaatataa tggagcccgc       420 ttttttttaag ctggcatcca gaaaaaaaaa gaatcccagc accaaaatat tgttttcttc       480
accaaccatc agttcatagg tccattctct tagcgcaact acacagaaca ggggcacaaa       540
caggcaaaaa acgggcacaa cctcaatgga gtgatgcaac ctgcttggag taaatgatga       600
cacaaggcaa ttgacctacg catgtatcta tctcattttc ttacaccttc tattaccttc       660
tgctctctct gatttggaaa aagctgaaaa aaaaggttga aaccagttcc ctgaaattat       720
tccctatttt gactaataag tatataaaga cggtaggtat tgattgtaat tctgtaaatc       780
tatttcttaa acttcttaaa ttctactttt atagttagtc ttttttttag tttaaaacac       840
caagaactta gtttcgaata acacacata aacaaacaaa tctagaatga aacttatgaa       900
tccatctatg aaggcatacg ttttctttat cttaagctac ttctctttac tcgttagctc       960
agctgcggtg ccaacctctg ccgccgtaca agttgagtca tacaattatg acggtaccac      1020
tttttcaggt agaatattcg tcaaaaacat tgcctactca aaggtcgtaa cagttatcta      1080
ctccgatgga tcagataact ggaacaataa caacaacaaa gttctgcag cttactcaga        1140 agcaatttct gggtctaact acgaatactg acattctcc gcaaagttat ccggaattaa        1200
acagttttat gtcaaatacg aagtttctgg ttcaacatat tacgacaaca acggtaccaa      1260
aaactaccaa gtccaagcaa cctcagcgac atctacaaca gctactgcaa ccacaactac      1320
agctactggc acaacaacta cttctacagg tccaactagt actgcatccg tatcattccc      1380
taccggtaac tcaacaattt cttcctggat aaaaaatcaa gaggaaatca gccgttttgc      1440
tatgttgaga aatatcaatc cacctgggtc tgccacaggg ttcatagccg catctctgtc      1500
cacagccggc ccagattact attactcttg gactagagat tcagcactaa cagctaatgt      1560
gatcgcttac gaatacaaca caacattcac tggaaacacc acccttctta agtacttgaa      1620
agattacgtt acatttttctg tcaaaagcca atctgtatct accgtttgta actgtctggg      1680
agaaccaaag ttcaacgctg atggtagttc ttttacaggt ccatggggca gaccacaaaa      1740
cgacggacca gcagagagag ctgttacttt tatgttgatt gctgacagct acttgactca      1800
aactaaggac gcatcctacg ttaccggtac attaaagcca gcaatcttca aagatcttga      1860
```

```
ttacgtagtt tctgtttggt ctaacggttg ctacgattta tgggaagagg ttaatggtgt   1920
tcatttctat actctcatgg tcatgagaaa gggtttgatc ttaggtgccg acttcgctgc   1980
tagaaatggt gactctagta gagcttcaac ctacaagcaa actgcatcaa caatggaatc   2040
aaagatcagt tcttttggt cagattctaa caactacgtc caagtttctc aatcagttac    2100
cgccggagtg tcaaaaaagg gactagatgt tagtacacta ttggcggcca acattggtag   2160
tctgcctgat ggcttttca ctccaggctc cgaaaagata ttggctacag cagtggcgtt    2220
agaaaatgca ttcgcatcct tgtacccaat taactctaac ctaccttctt acttgggtaa   2280
ctcaattgga agatatcctg aggatacata caacggtaat ggcaactctc aggggaatcc   2340
atggttcctt gccgtcaacg catacgcaga actttactac agagctatta aggaatggat   2400
tagtaatggc aaggtgacag tatccaatat ctcactacct ttcttcaaaa agtttgattc   2460
ttccgccact tctggaaaga catacactgc tggtacatca gatttcaata acttggctca   2520
gaacattgct ttaggcgccg atagattcct gtctactgtt aagttccacg catacactaa   2580
cgggagtcta tcagaagagt acgatagatc taccggtatg agtactgggg ctcgtgattt   2640
aacatggtcc catgcttcat tgatcacagt ggcgtacgca aaggccggta gtcctgcagc   2700
ttagttaatt aaacaggccc ctttcctttt gtcgatatca tgtaattagt tatgtcacgc    2760
ttacattcac gccctcctcc cacatccgct ctaaccgaaa aggaaggagt tagacaacct   2820
gaagtctagg tccctattta ttttttata gttatgttag tattaagaac gttatttata    2880
tttcaaattt ttctttttt tctgtacaaa cgcgtgtacg catgtaacgg cagacggcc     2940 ggccataact tcgtataatg tatgctatac gaagttatcc ttacatcaca cccaatcccc   3000
cacaagtgat cccccacaca ccatagcttc aaaatgtttc tactccttt ttactcttcc    3060 agattttctc ggactccgcg catcgccgta ccacttcaaa acacccaagc acagcatact   3120
aaatttcccc tctttcttcc tctagggtgg cgttaattac ccgtactaaa ggtttggaaa   3180
agaaaaaaga gaccgcctcg tttcttttc ttcgtcgaaa aaggcaataa aaattttat     3240 cacgtttctt tttcttgaaa aattttttt ttgatttttt tctctttcga tgacctccca    3300
ttgatattta agttaataaa tggtcttcaa tttctcaagt ttcagtttcg ttttcttgt    3360 tctattacaa ctttttac ttcttgctca ttagaaagaa agcatagcaa tctaatctaa     3420
gttttaatta caaaatgcca caatcctggg aagaattggc cgccgacaaa cgtgcccgtt   3480
tggctaaaac cattcctgac gaatggaagg ttcaaacttt gcctgccgaa gattccgtta   3540
ttgatttccc aaagaagtcc ggtattttgt ctgaggctga attgaagatt accgaagcct   3600
ctgctgctga tttggtctcc aagttggccg ctggtgagtt gacttctgtt gaagtcactt   3660 tggcttttg taagagagct gctattgctc aacaattaac caactgtgct cacgaattct   3720
tcccagatgc tgctttagct caagctagag aattagatga atactacgct aagcataaga   3780
gaccagttgg tccattacac ggtttaccaa tctctttaaa ggaccaattg cgtgttaagg   3840
gttacgaaac ctccatgggt tacatttcct ggttaaacaa atacgatgaa ggtgattccg   3900
tcttaaccac catgttgaga aaagctggtg ctgttttcta cgttaagacc tctgtcccac   3960 aaacccttgat ggtctgtgaa accgtcaaca acatcattgg tagaactgtc aatccaagaa   4020
acaaaaattg gtcctgtggt ggttcttctg gtggtgaagg tgctattgtt ggtattagag   4080
gtggtgttat tggtgtcggt actgacattg tggttccat tagagtccca gctgctttca   4140 acttttttata cggtttgaga ccatctcacg gtagattgcc atatgctaaa atggctaact   4200
ctatggaagg tcaagaaacc gttcactccg tcgttggtcc tatcactcac tccgtcgaag   4260
```

```
acttgagatt gttcaccaaa tctgtcttgg gtcaagaacc ttggaagtac gactctaagg    4320
tcatccccat gccatggaga caatctgaat ctgacatcat tgcctctaag attaagaatg    4380
gtggtttgaa cattggttat tacaatttcg acggtaacgt cttgccacac ccaccaattt    4440
tacgtggtgt cgaaactacc gttgccgctt tggc                                4474

<210> SEQ ID NO 23
<211> LENGTH: 1878
<212> TYPE: DNA
<213> ORGANISM: Artificial Sequence
<220> FEATURE:
<223> OTHER INFORMATION: Integration construct

<400> SEQUENCE: 23
gaagattacc gaagcctctg ctgctgattt ggtctccaag ttggccgctg gtgagttgac      60
ttctgttgaa gtcactttgg cttttttgtaa gagagctgct attgctcaac aattaaccaa    120
ctgtgctcac gaattcttcc cagatgctgc tttagctcaa gctagagaat tagatgaata    180
ctacgctaag cataagagac cagttggtcc attacacggt ttaccaatct ctttaaagga    240
ccaattgcgt gttaagggtt acgaaacctc catgggttac atttcctggt taaacaaata    300
cgatgaaggt gattccgtct taaccaccat gttgagaaaa gctggtgctg ttttctacgt    360 taagaccctct gtcccacaaa ccttgatggt ctgtgaaacc gtcaacaaca tcattggtag    420
aactgtcaat ccaagaaaca aaaattggtc ctgtggtggt tcttctggtg gtgaaggtgc    480
tattgttggt attagaggtg gtgttattgg tgtcggtact gacattggtg gttccattag    540
agtcccagct gctttcaact ttttatacgg tttgagacca tctcacggta gattgccata    600
tgctaaaatg gctaactcta tggaaggtca agaaaccgtt cactccgtcg ttggtcctat    660
cactcactcc gtcgaagact tgagattgtt caccaaatct gtcttgggtc aagaaccttg    720
gaagtacgac tctaaggtca tcccaatgcc atggagacaa tctgaatctg acatcattgc    780
ctctaagatt aagaatggtg gtttgaacat tggttattac aatttcgacg gtaacgtctt    840
gccacaccca ccaatttac gtggtgtcga aactaccgtt gccgctttgg ccaaggctgg    900
tcacaccgtt actccatgga ctccatacaa gcatgatttc ggtcatgact tgatttccca    960
catctatgct gctgatggtt ctgccgacgt catgagagac atttctgcct ctggtgagcc    1020
agccatccct aacattaagg acttgttgaa cccaaatatt aaggctgtta acatgaacga    1080
attgtgggac actcatttac aaaagtggaa ctatcaaatg gaatacttgg aaaagtggcg    1140
tgaagctgaa gaaaaagctg gtaaggaatt ggacgctatt atcgctccaa ttactcctac    1200
cgccgctgtc agacacgatc aattcagata ctacggttac gcctccgtta ttaacttatt    1260
ggatttcacc tctgttgtcg tcccagtcac tttcgctgat aagaatattg ataagaagaa    1320
cgaatctttt aaagctgttt ccgaattgga tgctttggtt caagaagaat acgacccaga    1380
ggcttatcac ggtgctcctg ttgctgttca agttattggt agaagattgt ccgaagagag    1440 aacttggct atcgccgaag aagtcggtaa attgttgggt aacgtcgtca ctccataagg    1500
agattgataa gacttttcta gttgcatatc ttttatattt aaatcttatc tattagttaa    1560 tttttttgtaa tttatcctta tatatagtct ggttattcta aatatcatt tcagtatcta    1620 aaaattcccc tctttttttca gttatatctt aacaggcgat aacttcgtat aatgtatgct    1680
atacgaagtt atgcggccgc cagcacgcag cacgctgtat ttacgtatttt aattttatat    1740 atttgtgcat acactactag ggaagacttg aaaaaaacct aggaaatgaa aaaacgacac    1800
```

```
aggaagtccc gtatttacta ttttttcctt ccttttgatg gggcagggcg gaaatagagg    1860
ataggataag cctactgc                                                  1878

<210> SEQ ID NO 24
<211> LENGTH: 4827
<212> TYPE: DNA
<213> ORGANISM: Artificial Sequence
<220> FEATURE:
<223> OTHER INFORMATION: Rhizopus microsporus GA integration construct

<400> SEQUENCE: 24
ggccgctcca tggagggcac agttaagccg ctaaaggcat tatccgccaa gtacaatttt      60
ttactcttcg aagacagaaa atttgctgac attggtaata cagtcaaatt gcagtactct    120
gcgggtgtat acagaatagc agaatgggca gacattacga atgcacacgg tgtggtgggc    180
ccaggtattg ttagcggttt gaagcaggcg gcggaagaag taacaaagga acctagaggc    240
cttttgatgt tagcagaatt gtcatgcaag ggctccctag ctactggaga atatactaag    300
ggtactgttg acattgcgaa gagcgacaaa gattttgtta tcggctttat tgctcaaaga    360
gacatgggtg aagagatga aggttacgat tggttgatta tgacacccgg tgtgggttta    420
gatgacaagg gagacgcatt gggtcaacag tatagaaccg tggatgatgt ggtctctaca    480
ggatctgaca ttattattgt tggaagagga ctatttgcaa agggaaggga tgctaaggta    540
gagggtgaac gttacagaaa agcaggctgg gaagcatatt tgagaagatg cggccagcaa    600
aactaaaaaa ctgtattata agtaaatgca tgtatactaa actcacaaat tagagcttca    660
atttaattat atcagttatt acccgggaat ctcggtcgta atgattttta taatgacgaa    720
aaaaaaaaaa ttggaaagaa aaagcttcat ggcctttata aaaggaacc atccaatacc    780 tcgccagaac caagtaacag tattttacgg ggcacaaatc aagaacaata agacaggact    840
gtaaagatgg acgcattgaa ctccaagaa caacaagagt tccaaaaagt agtggaacaa    900
aagcaaatga aggatttcat gcgtttgata acttcgtata atgtatgcta tacgaagtta    960
tctcgagggc cagaaaaagg aagtgtttcc ctccttcttg aattgatgtt accctcataa   1020
agcacgtggc ctcttatcga gaaagaaatt accgtcgctc gtgatttgtt tgcaaaaaga   1080
acaaaactga aaaaacccag acacgctcga cttcctgtct tcctgttgat gcagcttcc   1140 aatttcgtca cacaacaagg tcctagcgac ggctcacagg ttttgtaaca agcaatcgaa   1200
ggttctggaa tggcgggaaa gggtttagta ccacatgcta tgatgcccac tgtgatctcc   1260
agagcaaagt tcgttcgatc gtactgttac tctctctctt tcaaacagaa ttgtccgaat   1320
cgtgtgacaa caacagcctg ttctcacaca ctcttttctt ctaaccaagg gggtggttta   1380
gtttagtaga acctcgtgaa acttacattt acatatatat aaacttgcat aaattggtca   1440
atgcaagaaa tacatatttg gtcttttcta attcgtagtt tttcaagttc ttagatgctt   1500
tctttttctc tttttttacag atcatcaagg aagtaattat ctactttta caagtctaga   1560 atgaagctaa tgaacccatc tatgaaagct tatgtctttt tcatcttatc atacttctct   1620
ctcctagttt catctgccgc agtgcctaca tctgctgccg tccaagtgga aagttacaat   1680
tacgatggca ctaccttctc cggccgtatc ttcgtgaaaa acattgctta ctcaaaagtt   1740
gttacagtga tttactccga tggttctgat aattggaaca caataacaa caaagtttca   1800 gcagcgtact ccgaagccat tagtggatct aactacgaat actggacttt ctccgcaaag   1860
ttgtctggta ttaagcaatt ctcgtaaag tacgaagttt caggttcaac atactacgat   1920
aacaatggta ctaaaaacta ccaggtacaa gccacaagcg ctacaagtac aactgccaca   1980
```

```
gctacaacta caactgctac agggacaaca actacatcaa ccggtccaac atcaaccgca    2040
tctgtctcct ttccaaccgg taacagtaca atatcatcat ggatcaaaaa ccaagaggaa    2100
atctcaagat ttgcaatgtt gagaaacatc aatccaccag ggtcagcgac tggtttcatc    2160
gccgcttcat tgtccaccgc tgggccagac tactattact cttggactag agactctgca    2220
ttgacagcaa acgttatagc ttacgaatac aacacaacct tcactggtaa cactaccttg    2280
ttgaagtatc ttaaagacta cgtcactttt agtgttaagt ctcaatctgt ttctaccgtc    2340
tgtaactgtt taggtgaacc aaagtttaat gcagatggct catcatttac tggtccatgg    2400
ggcagacctc aaaacgatgg accagcgaaa agagcagtca cattcatgtt gatcgctgac    2460
tcatacttga cacaaactaa ggatgcttca tacgtgactg aacactcaa gccagccata    2520 ttcaaagacc tggattatgt tgtttctgtg tggtctaatg gttgctacga tttgtgggag    2580
gaagttaatg gcgtacattt ctacacacta atggttatga aaagggact aattcttggg    2640 gcagatttcg cagctagaaa tggtgattcc tcaagagcat ctacctacaa gcaaacagca    2700
tctacaatgg aatcaaagat cagctctttc tggtctgact ctaacaacta cgttcaagtt    2760
tcacaatctg tgactgctgg tgtaagtaaa aagggtttag atgtttctac tctgttagct    2820
gcaaacattg gttctttacc agatggcttc tttacaccag gatcagaaaa gattttggca    2880
actgccgttg ccttagagaa tgcattcgct ccctttacc ctattaactc taacttacct    2940
tcatatttgg gtaattcaat tggtagatat ccagaggaca catacaacgg aaacgggaat    3000
tcacagggca acccttggtt cttagccgta aacgcgtacg ccgagttata ctacagagcc    3060
attaaggaat ggatctcaaa tggtaaggta acagtctcta atatctctct tccttctttt    3120
aaaaagttcg attctagcgc cactagcggc aagacctata cagccggaac aagtgatttc    3180
aataacctcg ctcagaacat agctcttgga gcagacagat ttctgtcaac tgttaaattt    3240
cacgcgtaca caaatggcag cttgtctgaa gagtacgatc gttccaccgg gatgagtact    3300
ggtgctagag atctaacctg gtcccatgca tctcttatca cagttgcata cgcaaaagct    3360
ggatctcctg ctgcgtaatt aattaattta ccagcttact atccttcttg aaaatatgca    3420
ctctatatct tttagttctt aattgcaaca catagatttg ctgtataacg aattttatgc    3480
tattttttta atttggagtt cggtgatgaa agtgtcacag cgaatttcct cacatgtagg    3540
gaccgaattg tttacaagtt ctctgtacca ccatggagac atcaaagatt gaaaatctat    3600
ggaaagatat ggacggtagc aacaagaata tagcacgagc cgcggagttc atttcgttac    3660
ttttgatatc gctcacaact attgcgaagc gcttcagtga aaaaatcata aggaaaagtt    3720
gtaaatatta ttggtagtat tcgtttggta aagtagaggg ggtaattttt ccctttatt    3780 ttgttcatac attcttaaat tgctttgcct ctccttttgg aaagctatac ttcggagcac    3840
tgttgagcga aggctcaggc cggcagcacg cagcacgctg tatttacgta tttaatttta    3900
tatatttgtg catacactac tagggaagac ttgaaaaaaa cctaggaaat gaaaaaacga    3960
cacaggaagt cccgtatttta ctatttttc cttcctttg atggggcagg gcggaaatag    4020
aggataggat aagcctactg cttagctgtt tccgtctcta cttcggtagt tgtctcaatt    4080
gtcgtttcag tattaccttt agagccgcta gacgatggtt gagctatttg ttagggaaa    4140 actaagttca tgtaacacac gcataaccg attaaactca tgaatagctt gattgcagga    4200
ggctggtcca ttggagatgg tgccttattt tccttatagg caacgatgat gtcttcgtcg    4260
gtgttcaggt agtagtgtac actctgaatc agggagaacc aggcaatgaa cttgttcctc    4320
```

| | |
|---|---|
| aagaaaatag cggccatagg catggattgg ttaaccacac cagatatgct tggtgtggca | 4380 |
| gaatatagtc cttttggtgg cgcaattttc ttgtacctgt ggtagaaagg gagcggttga | 4440 |
| actgttagta tatattggca atatcagcaa atttgaaaga aaattgtcgg tgaaaaacat | 4500 |
| acgaaacaca aaggtcgggc cttgcaacgt tattcaaagt cattgtttag ttgaggaggt | 4560 |
| agcagcggag tatatgtatt cctttttttt gcctatggat gttgtaccat gcccattctg | 4620 |
| ctcaagcttt tgttaaaatt attttcagt attttttctt ccatgttgcg cgttacgaga | 4680 |
| acagaagcga cagataaccg caatcataca actagcgcta ctgcggggtg taaaaagcac | 4740 |
| aagaactaag ccaagatcac aacagttatc gataaaatag cagtgtttgc atggccattg | 4800 |
| agaaggacaa cattggcgtg cggcatg | 4827 |

<210> SEQ ID NO 25
<211> LENGTH: 4684
<212> TYPE: DNA
<213> ORGANISM: Artificial Sequence
<220> FEATURE:
<223> OTHER INFORMATION: Rhizopus microsporus GA integration construct

<400> SEQUENCE: 25

| | |
|---|---|
| ggccgcgaag gtgctattgt tggtattaga ggtggtgtta ttggtgtcgg tactgacatt | 60 |
| ggtggttcca ttagagtccc agctgctttc aacttttat acggtttgag accatctcac | 120 |
| ggtagattgc catatgctaa aatggctaac tctatggaag gtcaagaaac cgttcactcc | 180 |
| gtcgttggtc ctatcactca ctccgtcgaa gacttgagat tgttcaccaa atctgtcttg | 240 |
| ggtcaagaac cttggaagta cgactctaag gtcatcccaa tgccatggag acaatctgaa | 300 |
| tctgacatca ttgcctctaa gattaagaat ggtggtttga acattggtta ttacaatttc | 360 |
| gacggtaacg tcttgccaca cccaccaatt ttacgtggtg tcgaaactac cgttgccgct | 420 |
| ttggccaagg ctggtcacac cgttactcca tggactccat acaagcatga tttcggtcat | 480 |
| gacttgattt cccacatcta tgctgctgat ggttctgccg acgtcatgag agacatttct | 540 |
| gcctctggtg agccagccat ccctaacatt aaggacttgt tgaacccaaa tattaaggct | 600 |
| gttaacatga acgaattgtg ggacactcat ttacaaaagt ggaactatca aatggaatac | 660 |
| ttggaaaagt ggcgtgaagc tgaagaaaaa gctggtaagg aattggacgc tattatcgct | 720 |
| ccaattactc ctaccgccgc tgtcagacac gatcaattca gatactacgg ttacgcctcc | 780 |
| gttattaact tattggattt caccctctgt gtcgtcccag tcactttcgc tgataagaat | 840 |
| attgataaga agaacgaatc ttttaaagct gttccgaat tggatgcttt ggttcaagaa | 900 |
| gaatacgacc cagaggctta tcacggtgct cctgttgctg ttcaagttat tggtagaaga | 960 |
| ttgtccgaag agaactttt ggctatcgcc gaagaagtcg gtaaattgtt gggtaacgtc | 1020 |
| gtcactccat aagcgaattt cttatgattt atgattttta ttattaaata agttataaaa | 1080 |
| aaaataagtg tatacaaatt ttaaagtgac tcttaggttt taaaacgaaa attcttattc | 1140 |
| ttgagtaact cttcctgta ggtcaggttg ctttctcagg tatagcatga ggtcgctctt | 1200 |
| attgaccaca cctctaccgg catgccgagc aaatgcctgc aaatcgctcc ccatttcacc | 1260 |
| caattgtaga tatgctaact ccagcaatga gttgatgaat ctcggtgtgt attttatgtc | 1320 |
| ctcagaggac aacacataac ttcgtataat gtatgctata cgaagttatc tcgagggcca | 1380 |
| gaaaaggaa gtgtttccct ccttcttgaa ttgatgttac cctcataaag cacgtggcct | 1440 |
| cttatcgaga aagaaattac cgtcgctcgt gatttgtttg caaaagaac aaaactgaaa | 1500 |
| aaacccagac acgctcgact tcctgtcttc ctgttgattg cagcttccaa tttcgtcaca | 1560 |

```
caacaaggtc ctagcgacgg ctcacaggtt ttgtaacaag caatcgaagg ttctggaatg    1620
gcgggaaagg gtttagtacc acatgctatg atgcccactg tgatctccag agcaaagttc    1680
gttcgatcgt actgttactc tctctctttc aaacagaatt gtccgaatcg tgtgacaaca    1740
acagcctgtt ctcacacact cttttcttct aaccaagggg gtggtttagt ttagtagaac    1800
ctcgtgaaac ttacatttac atatatataa acttgcataa attggtcaat gcaagaaata    1860
catatttggt cttttctaat tcgtagtttt tcaagttctt agatgctttc tttttctctt    1920
ttttacagat catcaaggaa gtaattatct acttttttaca agtctagaat gaagctaatg   1980
aacccatcta tgaaagctta tgtcttttc atcttatcat acttctctct cctagtttca    2040
tctgccgcag tgcctacatc tgctgccgtc caagtggaaa gttacaatta cgatggcact    2100
accttctccg gccgtatctt cgtgaaaaac attgcttact caaaagttgt tacagtgatt    2160
tactccgatg gttctgataa ttggaacaac aataacaaca aagtttcagc agcgtactcc    2220
gaagccatta gtggatctaa ctacgaatac tggactttct ccgcaaagtt gtctggtatt    2280
aagcaattct acgtaaagta cgaagtttca ggttcaacat actacgataa caatggtact    2340
aaaaactacc aggtacaagc cacaagcgct acaagtacaa ctgccacagc tacaactaca    2400
actgctacag ggacaacaac tacatcaacc ggtccaacat caaccgcatc tgtctccttt    2460
ccaaccggta acagtacaat atcatcatgg atcaaaaacc aagaggaaat ctcaagattt    2520
gcaatgttga gaaacatcaa tccaccaggg tcagcgactg gtttcatcgc cgcttcattg    2580
tccaccgctg ggccagacta ctattactct tggactagag actctgcatt gacagcaaac    2640
gttatagctt acgaatacaa cacaaccttc actggtaaca ctaccttgtt gaagtatctt    2700
aaagactacg tcacttttag tgttaagtct caatctgttt ctaccgtctg taactgttta    2760
ggtgaaccaa agtttaatgc agatggctca tcatttactg gtccatgggg cagacctcaa    2820
aacgatggac cagcagaaag agcagtcaca ttcatgttga tcgctgactc atacttgaca    2880
caaactaagg atgcttcata cgtgactgga acactcaagc cagccatatt caaagacctg    2940
gattatgttg tttctgtgtg gtctaatggt tgctacgatt tgtgggagga agttaatggc    3000
gtacatttct acacactaat ggttatgaga aagggactaa ttcttggggc agatttcgca    3060
gctagaaatg gtgattcctc aagagcatct acctacaagc aaacagcatc tacaatggaa    3120
tcaaagatca gctctttctg gtctgactct aacaactacg ttcaagtttc acaatctgtg    3180
actgctggtg taagtaaaaa gggtttagat gtttctactc tgttagctgc aaacattggt    3240
tctttaccag atggcttctt tacaccagga tcagaaaaga ttttggcaac tgccgttgcc    3300
ttagagaatg cattcgcttc cctttacccct attaactcta acttaccttc atatttgggt    3360
aattcaattg gtagatatcc agaggacaca tacaacggaa acgggaattc acagggcaac    3420
ccttggttct tagccgtaaa cgcgtacgcc gagttatact acagagccat taaggaatgg    3480
atctcaaatg gtaaggtaac agtctctaat atctctcttc ctttctttaa aaagttcgat    3540
tctagcgcca ctagcggcaa gacctataca gccggaacaa gtgatttcaa taacctcgct    3600
cagaacatag ctcttggagc agacagattt ctgtcaactg ttaaatttca cgcgtacaca    3660
aatggcagct tgtctgaaga gtacgatcgt tccaccggga tgagtactgg tgctagagat    3720
ctaacctggt cccatgcatc tcttatcaca gttgcatacg caaaagctgg atctcctgct    3780
gcgtaattaa ttaatttacc agcttactat ccttcttgaa aatatgcact ctatatcttt    3840
tagttcttaa ttgcaacaca tagatttgct gtataacgaa ttttatgcta tttttttaat    3900
```

```
ttggagttcg gtgatgaaag tgtcacagcg aatttcctca catgtaggga ccgaattgtt    3960
tacaagttct ctgtaccacc atggagacat caaagattga aaatctatgg aaagatatgg    4020
acggtagcaa caagaatata gcacgagccg cggagttcat ttcgttactt tgatatcgc    4080 tcacaactat tgcgaagcgc ttcagtgaaa aaatcataag gaaaagttgt aaatattatt    4140
ggtagtattc gtttggtaaa gtagagggggg taattttttcc cctttatttt gttcatacat    4200
tcttaaattg ctttgcctct ccttttggaa agctatactt cggagcactg ttgagcgaag    4260
gctcaggccg gcagcacgca gcacgctgta tttacgtatt taattttata tatttgtgca    4320
tacactacta gggaagactt gaaaaaaacc taggaaatga aaaacgaca caggaagtcc    4380 cgtatttact attttttcct ccttttgat ggggcagggc ggaaatagag gataggataa    4440
gcctactgct tagctgtttc cgtctctact tcggtagttg tctcaattgt cgtttcagta    4500
ttacctttag agccgctaga cgatggttga gctatttgtt gagggaaaac taagttcatg    4560
taacacacgc ataacccgat taaactcatg aatagcttga ttgcaggagg ctggtccatt    4620
ggagatggtg ccttatttc cttataggca acgatgatgt cttcgtcggt gttcaggtag    4680
tagt                                                                 4684
```

<210> SEQ ID NO 26
<211> LENGTH: 4909
<212> TYPE: DNA
<213> ORGANISM: Artificial Sequence
<220> FEATURE:
<223> OTHER INFORMATION: Rhizopus delemar GA integration construct

<400> SEQUENCE: 26

```
ctaaattcgg ccttgctcag agactcctgg attttggcta caacgcagt cccttcgatg      60 catatagcta ggccacaaat tatgccaata acggtccatg ggttgatgtt ttcttgaatt    120
ctttcgtttt tcatgctatt tgcgtcttcc caagtcccag cgttccagta ttcatactgc    180
gcgttagagt ggtagccata agagccggca tattggtaat tttcagtatt aacgttagaa    240
cgtggtgaat acgatgtggt ccagccttgc ctcgttgtgt catatacgat ctttttcttt    300
gggtcacaaa gaatatcata tgcttgagag atgactttaa atctatgtag tttttcgctt    360
gatgttagca gcagcggtga tttactatca ctgttggtaa ccttttctga gctaaatatt    420
tgaatgttat cggaatggtc agggtggtac aattttacat aacgatgata ttttttttt     480 aacgacttct tgtccagttt aggatttcca gatccggcct ttggaatgcc aaaaatatca    540
tagggagttg gatctgccaa ctcaggccat tgttcatccc ttatcgtaag ttttctattg    600
ccatttttat cgttcgctgt agcatactta gctataaaag tgatttgtgg gggacacttt    660
tctacacatg ataagtgcca cttgaataaa aatgggtata cgaacttatg gtgtagcata    720
acaaatatat tgcaagtagt gacctatggt gtgtagatat acgtacagtt agttacgagc    780
ctaaagacac aacgtgtttg ttaattatac tgtcgctgta atatcttctc ttccattatc    840
accggtcatt ccttgcaggg gcggtagtac ccggagaccc tgaactttc tttttttttt    900 tgcgaaatta aaaagttcat tttcaattcg acaatgagat ctacaagcca ttgttttatg    960
ttgatgagag ccagcttaaa gagttctcga gatctcccga gttatcatt atcaatactg   1020 ccatttcaaa gaatacgtaa ataattaata gtagtgattt tcctaacttt atttagtcaa   1080
aaaattggcc ttttaattct gctgtaaccc gtacatgccc aaaatagggg gcgggttaca   1140
cagaatatat aacatcatag gtgtctgggt gaacagttta ttcctggcat ccactaaata   1200
taatggagcc cgctttttt aagctggcat ccagaaaaaa aaagaatccc agcaccaaaa   1260
```

```
tattgttttc ttcaccaacc atcagttcat aggtccattc tcttagcgca actacacaga    1320 acagggcac aaacaggcaa aaacgggca caacctcaat ggagtgatgc aacctgcttg      1380
gagtaaatga tgacacaagg caattgacct acgcatgtat ctatctcatt ttcttacacc   1440
ttctattacc ttctgctctc tctgatttgg aaaaagctga aaaaaaggt tgaaaccagt    1500 tccctgaaat tattccccta tttgactaat aagtatataa agacggtagg tattgattgt   1560
aattctgtaa atctatttct taaacttctt aaattctact tttatagtta gtcttttttt   1620
tagtttaaaa caccaagaac ttagtttcga ataaacacac ataaacaaac aaatctagaa   1680
tgcagttatt caacttacca cttaaggtat ctttctttct agtcttatct tacttttcat   1740
tgttagtatc agctgcctct ataccaagtt cagcatccgt acaactagat tcatacaatt   1800
acgacggttc aacattctca ggaaagatat acgtgaaaaa tattgcttac agcaaaaagg   1860
ttactgtgat ttacgcagat gggtcagaca actggaataa caatggaaac acaattgctg   1920
cttcctattc tgcccctatt tctggatcta actacgaata ctggactttt tcagcgagta   1980
taaacggaat taaggaattc tatatcaaat atgaagtctc tggtaagacc tactacgata   2040
acaacaactc cgcaaactac caagttagca catcaaagcc aaccacaaca actgctactg   2100
cgacaactac aaccgcacca agcacttcta ctacaacacc tcctagttca tctgagccag   2160
caactttccc aactggtaat tccactattt cttcttggat caaaaaacaa gagggtatct   2220
caagattcgc catgcttaga aatatcaatc ctccaggctc tgcaacagga ttcattgcag   2280
catctttatc aactgcgggg ccagactact actacgcctg gactagagat gcagctttga   2340
catcaaatgt gattgtttat gaatacaaca caactttgtc cggtaacaag acaatcttga   2400
acgtcttgaa ggattatgtg acattctctg tcaagactca atctacatca acagtttgta   2460
actgtctcgg cgaaccaaag ttcaaccctg atggtagtgg ttacactggt gcttggggta   2520
gaccacaaaa cgatggtcca gcagagagag ctacaacttt catcttgttt gctgactctt   2580
acctaacaca aaccaaggat gcaagctacg ttactggaac actaaagcct gcaatcttta   2640
aagacctgga ctatgttgta aacgtttggt caaatggctg cttcgatcta tgggaggaag   2700
tgaacggtgt tcacttctac acattaatgg tcatgagaaa gggactcttg cttggtgcag   2760
actttgctaa gagaaacggt gattctacac gtgcctccac ttactcctcc acagcttcaa   2820
ccattgccaa caaaatctct tctttctggg tcagctcaaa taactggatt caagtttctc   2880
aatcagttac tggtggtgtt tctaaaaagg gcctggatgt gtcaaccttg cttgctgcca   2940
atttgggcag tgttgatgac gggttcttca ccccaggttc tgaaaagatc ctcgccaccg   3000
cagttgccgt tgaagattca tttgctagtt tatacccaat caacaaaaat ctaccatcat   3060
accttggaaa ttcaatcggt agatatccag aggatacata caacggtaat ggaaactctc   3120
agggtaaccc ttggtttctt gcagttacag ggtacgctga actgtactac agagcgatta   3180
aggaatggat tggtaatggc ggcgtaactg ttagttctat ttctctacct ttcttcaaaa   3240
agttcgatag ttctgcaaca tctggtaaaa agtacacagt cggcacttcc gattttaaca   3300
atttagctca gaacatagca ctggcagctg atcgtttctt gagtacagtc caattgcatg   3360
cccataacaa cggtagtttg gctgaagagt ttgatagaac caccggttta tcaaccggcg   3420
ccagagattt aacatggtcc catgcgtctt tgataactgc ttcttacgcc aaggctgggg   3480
caccagctgc ctgattaatt aaacaggccc ctttcctttt gtcgatatca tgtaattagt   3540
tatgtcacgc ttacattcac gccctcctcc cacatccgct ctaaccgaaa aggaaggagt   3600
```

```
tagacaacct gaagtctagg tccctattta tttttttata gttatgttag tattaagaac   3660
gttatttata tttcaaattt ttctttttt tctgtacaaa cgcgtgtacg catgtaacgg   3720
gcagacggcc ggccataact tcgtataatg tatgctatac gaagttatgg caacggttca   3780
tcatctcatg gatctgcaca tgaacaaaca ccagagtcaa acgacgttga aattgaggct   3840
actgcgccaa ttgatgacaa tacagacgat gataacaaac cgaagttatc tgatgtagaa   3900
aaggattaga gatgctaaga gatagtgatg atatttcata aataatgtaa ttctatatat   3960
gttaattacc ttttttgcga ggcatattta tggtgaagga taagttttga ccatcaaaga   4020
aggttaatgt ggctgtggtt tcagggtcca taaagctttt caattcatct ttttttttt    4080
tgttctttt tttgattccg gtttctttga aattttttg attcggtaat ctccgagcag    4140
aaggaagaac gaaggaagga gcacagactt agattggtat atatacgcat atgtggtgtt   4200
gaagaaacat gaaattgccc agtattctta acccaactgc acagaacaaa aacctgcagg   4260
aaacgaagat aaatcatgtc gaaagctaca tataaggaac gtgctgctac tcatcctagt   4320
cctgttgctg ccaagctatt taatatcatg cacgaaaagc aaacaaactt gtgtgcttca   4380
ttggatgttc gtaccaccaa ggaattactg gagttagttg aagcattagg tcccaaaatt   4440
tgtttactaa aaacacatgt ggatatcttg actgattttt ccatggaggg cacagttaag   4500
ccgctaaagg cattatccgc caagtacaat ttttttactct tcgaagacag aaaatttgct   4560
gacattggta atacagtcaa attgcagtac tctgcgggtg tatacagaat agcagaatgg   4620
gcagacatta cgaatgcaca cggtgtggtg ggcccaggta ttgttagcgg tttgaagcag   4680
gcggcggaag aagtaacaaa ggaacctaga ggccttttga tgttagcaga attgtcatgc   4740
aagggctccc tagctactgg agaatatact aagggtactg ttgacattgc gaagagcgac   4800
aaagattttg ttatcggctt tattgctcaa agagacatgg gtggaagaga tgaaggttac   4860
gattggttga ttatgacacg caggttacga ttggttgatt atgacacgc                4909
```

<210> SEQ ID NO 27
<211> LENGTH: 4824
<212> TYPE: DNA
<213> ORGANISM: Artificial Sequence
<220> FEATURE:
<223> OTHER INFORMATION: Rhizopus delemar GA integration construct

<400> SEQUENCE: 27

```
ggccgctcca tggagggcac agttaagccg ctaaaggcat tatccgccaa gtacaatttt    60
ttactcttcg aagacagaaa atttgctgac attggtaata cagtcaaatt gcagtactct   120
gcgggtgtat acagaatagc agaatgggca gacattacga atgcacacgg tgtggtgggc   180
ccaggtattg ttagcggttt gaagcaggcg gcggaagaag taacaaagga acctagaggc   240
cttttgatgt tagcagaatt gtcatgcaag ggctccctag ctactggaga atatactaag   300
ggtactgttg acattgcgaa gagcgacaaa gattttgtta tcggctttat tgctcaaaga   360
gacatgggtg gaagagatga aggttacgat tggttgatta tgacacccgg tgtgggttta   420
gatgacaagg gagacgcatt gggtcaacag tatagaaccg tggatgatgt ggtctctaca   480
ggatctgaca ttattattgt tggaagagga ctatttgcaa agggaaggga tgctaaggta   540
gagggtgaac gttacagaaa agcaggctgg gaagcatatt tgagaagatg cggccagcaa   600
aactaaaaaa ctgtattata agtaaatgca tgtatactaa actcacaaat tagagcttca   660
atttaattat atcagttatt acccgggaat ctcggtcgta atgattttta taatgacgaa   720
aaaaaaaaaa ttggaaagaa aaagcttcat ggccttata aaaggaacc atccaatacc   780
```

```
tcgccagaac caagtaacag tattttacgg ggcacaaatc aagaacaata agacaggact    840
gtaaagatgg acgcattgaa ctccaaagaa caacaagagt tccaaaaagt agtggaacaa    900
aagcaaatga aggatttcat gcgtttgata acttcgtata atgtatgcta tacgaagtta    960
tctcgagggc cagaaaaagg aagtgtttcc ctccttcttg aattgatgtt accctcataa   1020
agcacgtggc ctcttatcga gaagaaatt accgtcgctc gtgatttgtt tgcaaaaaga   1080
acaaaactga aaaacccag acacgctcga cttcctgtct tcctgttgat tgcagcttcc   1140
aatttcgtca cacaacaagg tcctagcgac ggctcacagg ttttgtaaca agcaatcgaa   1200
ggttctggaa tggcgggaaa gggtttagta ccacatgcta tgatgcccac tgtgatctcc   1260
agagcaaagt tcgttcgatc gtactgttac tctctctctt tcaaacagaa ttgtccgaat   1320
cgtgtgacaa caacagcctg ttctcacaca ctctttttctt ctaaccaagg gggtggttta   1380
gtttagtaga acctcgtgaa acttacattt acatatatat aaacttgcat aaattggtca   1440
atgcaagaaa tacatatttg gtcttttcta attcgtagtt tttcaagttc ttagatgctt   1500
tcttttctc ttttttacag atcatcaagg aagtaattat ctacttttta caagtctaga   1560
atgcagctgt tcaacttgcc attaaaggtt tcattctttt tggtcctatc atactttagt   1620
ttgttggtgt cagccgcatc tattccatct tcagcatctg tacaattaga ctcctacaat   1680
tacgacggct ctacattcag cggaaagatt tacgtgaaaa atattgcgta cagcaaaaaa   1740
gtaactgtta tctatgccga cggatcagat aactggaaca caatggaaa cactatcgct   1800
gccagttact ctgcaccaat ttcaggttct aactacgaat attggacatt ctcagcctcc   1860
atcaatggca ttaaggaatt ctacataaag tacgaagttt ccggtaagac ttactacgat   1920
aacaacaatt ctgcaaacta tcaagtatca acatcaaaac ctactaccac caccgccaca   1980
gctacaacta caactgcacc ttcaacatct accacaaccc caccatcttc tagcgaacca   2040
gctacattcc caactggcaa ttctactatt tctagttgga tcaaaaaaca agagggtatt   2100
tccagattcg caatgttgag aaacataaat ccaccaggat cagcaactgg attcatcgca   2160
gcttctttgt ccacagcggg gccagattac tactacgcat ggaccagaga tgctgctttg   2220
acaagtaacg ttattgttta cgaatacaat accactttgt ccgtaacaa gactattctt   2280
aacgtcctaa aggattacgt tacattctct gttaagactc agtctacatc cacagtctgc   2340
aattgtttgg gtgaaccaaa gttcaaccca gatggctctg gatacacagg tgcctggggt   2400
cgtccacaaa acgatgggcc tgccgagaga gccactacat ttatcctatt tgctgactca   2460
taccttacac aaacaaaaga tgcatcctac gtgactggaa cattaaagcc tgcaatcttc   2520
aaagacctgg attacgttgt caacgtgtgg tctaacggct gtttcgatct atgggaagag   2580
gttaacggcg tgcacttcta cactctaatg gtcatgagaa agggtctgtt gttaggtgca   2640
gattttgcta agagaaacgg tgattctaca cgtgcttcta cctactcctc aacagcatca   2700
actattgcga acaagatttc ttcatttggt gtttcaagta ataactggat acaagtatct   2760
caaagcgtta caggggggtgt ctcaaaaaag ggtcttgatg tttctacatt actggctgct   2820
aatcttgggt ctgttgatga cggtttcttc accctggtt ctgaaaagat cctcgctacc   2880
gccgtcgcgg ttgaggatag ttttgcttca ctctatccta taaacaaaaa ccttccttca   2940
tacttaggaa acagtatcgg tagatacca gaggatacat acaatggtaa tggcaattca   3000
cagggaaatc catggttcct tgctgttaca gggtacgcag aactttacta tagagctatt   3060
aaggaatgga tcggcaacgg cggtgtgaca gtttcctcaa tctcattgcc atttttcaaa   3120
```

```
aagtttgact ccagcgcgac atctggtaaa aagtatactg tggggacttc tgatttcaac    3180
aatttggctc aaaacattgc cttagctgcc gacagattct tatctaccgt acaactccat    3240
gcacataaca atggtagttt ggcagaggaa tttgatagaa ctacaggact ctctacaggt    3300
gcgagagatt taacttggtc acatgcaagt ttaattacag cctcttacgc aaaggctggt    3360
gctcctgctg cataattaat taatttacca gcttactatc cttcttgaaa atatgcactc    3420
tatatctttt agttcttaat tgcaacacat agatttgctg tataacgaat tttatgctat    3480
ttttttaatt tggagttcgg tgatgaaagt gtcacagcga atttcctcac atgtagggac    3540
cgaattgttt acaagttctc tgtaccacca tggagacatc aaagattgaa atctatgga    3600 aagatatgga cggtagcaac aagaatatag cacgagccgc ggagttcatt tcgttacttt    3660
tgatatcgct cacaactatt gcgaagcgct tcagtgaaaa aatcataagg aaaagttgta    3720
aatattattg gtagtattcg tttggtaaag tagagggggt aattttttccc ctttatttg    3780 ttcatacatt cttaaattgc tttgcctctc cttttggaaa gctatacttc ggagcactgt    3840
tgagcgaagg ctcaggccgg cagcacgcag cacgctgtat ttacgtattt aattttatat    3900
atttgtgcat acactactag ggaagacttg aaaaaaacct aggaaatgaa aaaacgacac    3960
aggaagtccc gtatttacta ttttttcctt ccttttgatg gggcagggcg aaatagagg    4020 ataggataag cctactgctt agctgttttcc gtctctactt cggtagttgt ctcaattgtc    4080
gtttcagtat tacctttaga gccgctagac gatggttgag ctatttgttg agggaaaact    4140
aagttcatgt aacacacgca taacccgatt aaactcatga atagcttgat tgcaggaggc    4200
tggtccattg gagatggtgc cttatttttcc ttataggcaa cgatgatgtc ttcgtcggtg    4260
ttcaggtagt agtgtacact ctgaatcagg gagaaccagg caatgaactt gttcctcaag    4320
aaaatagcgg ccataggcat ggattggtta accacaccag atatgcttgg tgtggcagaa    4380
tatagtcctt ttggtggcgc aattttcttg tacctgtggt agaaagggag cggttgaact    4440
gttagtatat attggcaata tcagcaaatt tgaaagaaaa ttgtcggtga aaacatacg    4500 aaacacaaag gtcgggcctt gcaacgttat tcaaagtcat tgtttagttg aggaggtagc    4560
agcggagtat atgtattcct ttttttttgcc tatggatgtt gtaccatgcc cattctgctc    4620
aagcttttgt taaaattatt tttcagtatt ttttcttcca tgttgcgcgt tacgagaaca    4680
gaagcgacag ataaccgcaa tcatacaact agcgctactg cggggtgtaa aaagcacaag    4740
aactaagcca agatcacaac agttatcgat aaaatagcag tgtttgcatg gccattgaga    4800 aggacaaacat tggcgtgcgg catg                                          4824
```

<210> SEQ ID NO 28
<211> LENGTH: 5264
<212> TYPE: DNA
<213> ORGANISM: Artificial Sequence
<220> FEATURE:
<223> OTHER INFORMATION: Rhizopus delemar GA integration construct

<400> SEQUENCE: 28

```
ctaaattcgg ccttgctcag agactcctgg attttggcta caacgcagt cccttcgatg      60 catatagcta ggccacaaat tatgccaata acggtccatg ggttgatgtt ttcttgaatt    120
ctttcgtttt tcatgctatt tgcgtcttcc caagtcccag cgttccagta ttcatactgc    180
gcgttagagt ggtagccata agagccggca tattggtaat tttcagtatt aacgttagaa    240
cgtggtgaat acgatgtggt ccagccttgc ctcgttgtgt catatacgat ctttttcttt    300
gggtcacaaa gaatatcata tgcttgagag atgactttaa atctatgtag ttttttcgctt    360
```

```
gatgttagca gcagcggtga tttactatca ctgttggtaa cctttctga gctaaatatt    420 tgaatgttat cggaatggtc agggtggtac aattttacat aacgatgata tttttttttt    480
aacgacttct tgtccagttt aggatttcca gatccggcct ttggaatgcc aaaaatatca    540
tagggagttg gatctgccaa ctcaggccat tgttcatccc ttatcgtaag ttttctattg    600
ccatttttat cgttcgctgt agcatactta gctataaaag tgatttgtgg gggacacttt    660
tctacacatg ataagtgcca cttgaataaa aatgggtata cgaacttatg gtgtagcata    720
acaaatatat tgcaagtagt gacctatggt gtgtagatat acgtacagtt agttacgagc    780
ctaaagacac aacgtgtttg ttaattatac tgtcgctgta atatcttctc ttccattatc    840
accggtcatt ccttgcaggg gcggtagtac ccggagaccc tgaacttttc tttttttttt    900
tgcgaaatta aaaagttcat tttcaattcg acaatgagat ctacaagcca ttgttttatg    960
ttgatgagag ccagcttaaa gagttctcga gatctcccga gtttatcatt atcaatactg   1020
ccatttcaaa gaatacgtaa ataattaata gtagtgattt tcctaacttt atttagtcaa   1080
aaaattggcc ttttaattct gctgtaaccc gtacatgccc aaaatagggg gcgggttaca   1140
cagaatatat aacatcatag gtgtctgggt gaacagttta ttcctggcat ccactaaata   1200
taatggagcc cgcttttttt aagctggcat ccagaaaaaa aaagaatccc agcaccaaaa   1260
tattgttttc ttcaccaacc atcagttcat aggtccattc tcttagcgca actacacaga   1320 acagggcac aaacaggcaa aaacgggca aacctcaat ggagtgatgc aacctgcttg   1380
gagtaaatga tgcacaagg caattgacct acgcatgtat ctatctcatt ttcttacacc   1440
ttctattacc ttctgctctc tctgatttgg aaaaagctga aaaaaaggt tgaaaccagt   1500 tccctgaaat tattcccta tttgactaat aagtatataa agacggtagg tattgattgt   1560
aattctgtaa atctatttct taaacttctt aaattctact tttatagtta gtctttttt   1620 tagtttaaaa caccaagaac ttagtttcga ataaacacac ataaacaaac aaatctagaa   1680
tgcagttatt caacttacca cttaaggtat cttctttct agtcttatct tacttttcat   1740
tgttagtatc agctgcctct ataccaagtt cagcatccgt acaactagat tcatacaatt   1800
acgacggttc aacattctca ggaaagatat acgtgaaaaa tattgcttac agcaaaaagg   1860
ttactgtgat ttacgcagat gggtcagaca actggaataa caatggaaac acaattgctg   1920
cttcctattc tgccctatt tctggatcta actacgaata ctggacttt tcagcgagta   1980 taaacggaat taaggaattc tatatcaaat atgaagtctc tggtaagacc tactacgata   2040
acaacaactc cgcaaactac caagttagca catcaaagcc aaccacaaca actgctactg   2100
cgacaactac aaccgcacca agcacttcta ctacaacacc tcctagttca tctgagccag   2160
caactttccc aactggtaat tccactattt cttcttggat caaaaaacaa gagggtatct   2220
caagattcgc catgcttaga aatatcaatc ctccaggctc tgcaacagga ttcattgcag   2280
catctttatc aactgcgggg ccagactact actacgcctg gactagagat gcagctttga   2340
catcaaatgt gattgtttat gaatacaaca caactttgtc cggtaacaag acaatcttga   2400
acgtcttgaa ggattatgtg acattctctg tcaagactca atctacatca acagtttgta   2460
actgtctcgg cgaaccaaag ttcaaccctg atggtagtgg ttacactggt gcttggggta   2520
gaccacaaaa cgatggtcca gcagagagag ctacaacttt catcttgttt gctgactctt   2580
acctaacaca aaccaaggat gcaagctacg ttactggaac actaaagcct gcaatctta   2640 aagacctgga ctatgttgta aacgtttggt caaatggctg cttcgatcta tgggaggaag   2700
```

```
tgaacggtgt tcacttctac acattaatgg tcatgagaaa gggactcttg cttggtgcag    2760
actttgctaa gagaaacggt gattctacac gtgcctccac ttactcctcc acagcttcaa    2820
ccattgccaa caaaatctct tctttctggg tcagctcaaa taactggatt caagtttctc    2880
aatcagttac tggtggtgtt tctaaaaagg gcctggatgt gtcaaccttg cttgctgcca    2940
atttgggcag tgttgatgac gggttcttca ccccaggttc tgaaaagatc ctcgccaccg    3000
cagttgccgt tgaagattca tttgctagtt tatacccaat caacaaaaat ctaccatcat    3060
accttggaaa ttcaatcggt agatatccag aggatacata caacggtaat ggaaactctc    3120
agggtaaccc ttggtttctt gcagttacag ggtacgctga actgtactac agagcgatta    3180
aggaatggat tggtaatggc ggcgtaactg ttagttctat ttctctacct ttcttcaaaa    3240
agttcgatag ttctgcaaca tctggtaaaa agtacacagt cggcacttcc gattttaaca    3300
atttagctca gaacatagca ctggcagctg atcgtttctt gagtacagtc caattgcatg    3360
cccataacaa cggtagtttg gctgaagagt tgatagaaac caccggttta tcaaccggcg    3420
ccagagattt aacatggtcc catgcgtctt tgataactgc ttcttacgcc aaggctgggg    3480
caccagctgc ctgattaatt aaacaggccc cttttccttt gtcgatatca tgtaattagt    3540
tatgtcacgc ttacattcac gccctcctcc cacatccgct ctaaccgaaa aggaaggagt    3600
tagacaacct gaagtctagg tccctattta tttttttata gttatgttag tattaagaac    3660
gttatttata tttcaaattt ttcttttttt tctgtacaaa cgcgtgtacg catgtaacgg    3720
gcagacggcc ggccataact tcgtataatg tatgctatac gaagttatcc ttacatcaca    3780
cccaatcccc cacaagtgat cccccacaca ccatagcttc aaaatgtttc tactcctttt    3840
ttactcttcc agattttctc ggactccgcg catcgccgta ccacttcaaa cacccaagc    3900 acagcatact aaatttcccc tctttcttcc tctagggtgg cgttaattac ccgtactaaa    3960
ggtttggaaa agaaaaaaga gaccgcctcg tttctttttc ttcgtcgaaa aaggcaataa    4020 aaattttat cacgtttctt tttcttgaaa aatttttttt ttgattttt tctctttcga    4080 tgacctccca ttgatattta agttaataaa tggtcttcaa tttctcaagt ttcagtttcg    4140 ttttttcttgt tctattacaa ctttttttac ttcttgctca ttagaaagaa agcatagcaa    4200
tctaatctaa gttttaatta caaaatgcca caatcctggg aagaattggc cgccgacaaa    4260
cgtgcccgtt tggctaaaac cattcctgac gaatggaagg ttcaaacttt gcctgccgaa    4320
gattccgtta ttgatttccc aaagaagtcc ggtattttgt ctgaggctga attgaagatt    4380
accgaagcct ctgctgctga tttggtctcc aagttggccg ctggtgagtt gacttctgtt    4440
gaagtcactt tggcttttg taagagagct gctattgctc aacaattaac caactgtgct    4500
cacgaattct cccagatgc tgctttagct caagctagag aattagatga atactacgct    4560
aagcataaga gaccagttgg tccattacac ggtttaccaa tctctttaaa ggaccaattg    4620
cgtgttaagg gttacgaaac ctccatgggt tacatttcct ggttaaacaa atacgatgaa    4680
ggtgattccg tcttaaccac catgttgaga aaagctggtg ctgttttcta cgttaagacc    4740
tctgtcccac aaaccttgat ggtctgtgaa accgtcaaca acatcattgg tagaactgtc    4800
aatccaagaa acaaaaattg gtcctgtggt ggttcttctg gtggtgaagg tgctattgtt    4860
ggtattagag gtggtgttat tggtgtcggt actgacattg gtggttccat tagagtccca    4920
gctgctttca cttttttata cggtttgaga ccatctcacg gtagattgcc atatgctaaa    4980
atggctaact ctatgaagg tcaagaaacc gttcactccg tcgttggtcc tatcactcac    5040
tccgtcgaag acttgagatt gttcaccaaa tctgtcttgg gtcaagaacc ttggaagtac    5100
```

| | | |
|---|---|---|
| gactctaagg tcatccccat gccatggaga caatctgaat ctgacatcat tgcctctaag | 5160 | |
| attaagaatg gtggtttgaa cattggttat tacaatttcg acggtaacgt cttgccacac | 5220 | |
| ccaccaattt tacgtggtgt cgaaactacc gttgccgctt tggc | 5264 | |

<210> SEQ ID NO 29
<211> LENGTH: 5026
<212> TYPE: DNA
<213> ORGANISM: Artificial Sequence
<220> FEATURE:
<223> OTHER INFORMATION: Rhizopus delemar GA integration construct

<400> SEQUENCE: 29

| | | |
|---|---|---|
| ggccgcgaag gtgctattgt tggtattaga ggtggtgtta ttggtgtcgg tactgacatt | 60 | |
| ggtggttcca ttagagtccc agctgctttc aacttttat acggtttgag accatctcac | 120 | |
| ggtagattgc catatgctaa aatggctaac tctatggaag gtcaagaaac cgttcactcc | 180 | |
| gtcgttggtc ctatcactca ctccgtcgaa gacttgagat tgttcaccaa atctgtcttg | 240 | |
| ggtcaagaac cttggaagta cgactctaag gtcatcccaa tgccatggag acaatctgaa | 300 | |
| tctgacatca ttgcctctaa gattaagaat ggtggtttga acattggtta ttacaatttc | 360 | |
| gacggtaacg tcttgccaca cccaccaatt ttacgtggtg tcgaaactac cgttgccgct | 420 | |
| ttggccaagg ctggtcacac cgttactcca tggactccat acaagcatga tttcggtcat | 480 | |
| gacttgattt cccacatcta tgctgctgat ggttctgccg acgtcatgag agacatttct | 540 | |
| gcctctggtg agccagccat ccctaacatt aaggacttgt tgaacccaaa tattaaggct | 600 | |
| gttaacatga acgaattgtg ggacactcat ttacaaaagt ggaactatca aatggaatac | 660 | |
| ttggaaaagt ggcgtgaagc tgaagaaaaa gctggtaagg aattggacgc tattatcgct | 720 | |
| ccaattactc ctaccgccgc tgtcagacac gatcaattca gatactacgg ttacgcctcc | 780 | |
| gttattaact tattggattt cacctctgtt gtcgtcccag tcactttcgc tgataagaat | 840 | |
| attgataaga agaacgaatc ttttaaagct gttttccgaat tggatgcttt ggttcaagaa | 900 | |
| gaatacgacc cagaggctta tcacggtgct cctgttgctg ttcaagttat tggtagaaga | 960 | |
| ttgtccgaag agagaacttt ggctatcgcc gaagaagtcg gtaaattgtt gggtaacgtc | 1020 | |
| gtcactccat aagcgaattt cttatgattt atgattttta ttattaaata agttataaaa | 1080 | |
| aaaataagtg tatacaaatt ttaaagtgac tcttaggttt taaaacgaaa attcttattc | 1140 | |
| ttgagtaact ctttcctgta ggtcaggttg cttttctcagg tatagcatga ggtcgctctt | 1200 | |
| attgaccaca cctctaccgg catgccgagc aaatgcctgc aaatcgctcc ccatttcacc | 1260 | |
| caattgtaga tatgctaact ccagcaatga gttgatgaat ctcggtgtgt attttatgtc | 1320 | |
| ctcagaggac aacacataac ttcgtataat gtatgctata cgaagttatc tcgagggcca | 1380 | |
| gaaaaggaa gtgtttccct ccttcttgaa ttgatgttac cctcataaag cacgtggcct | 1440 | |
| cttatcgaga aagaaattac cgtcgctcgt gatttgtttg caaaaagaac aaaactgaaa | 1500 | |
| aaacccagac acgctcgact tcctgtcttc ctgttgattg cagcttccaa tttcgtcaca | 1560 | |
| caacaaggtc ctagcgacgg ctcacaggtt ttgtaacaag caatcgaagg ttctggaatg | 1620 | |
| gcgggaaagg gtttagtacc acatgctatg atgcccactg tgatctccag agcaaagttc | 1680 | |
| gttcgatcgt actgttactc tctctctttc aaacagaatt gtccgaatcg tgtgacaaca | 1740 | |
| acagcctgtt ctcacacact ctttcttcct aaccaagggg gtggtttagt ttagtagaac | 1800 | |
| ctcgtgaaac ttcatttac atatatataa acttgcataa attggtcaat gcaagaaata | 1860 | |

```
catatttggt cttttctaat tcgtagtttt tcaagttctt agatgctttc ttttctcttt      1920
ttttacagat catcaaggaa gtaattatct acttttttaca agtctagaat gcagctgttc     1980
aacttgccat taaaggtttc attcttttttg gtcctatcat actttagttt gttggtgtca     2040
gccgcatcta ttccatcttc agcatctgta caattagact cctacaatta cgacggctct     2100
acattcagcg gaaagattta cgtgaaaaat attgcgtaca gcaaaaagt aactgttatc      2160 tatgccgacg gatcagataa ctggaacaac aatggaaaca ctatcgctgc cagttactct     2220
gcaccaattt caggttctaa ctacgaatat tggacattct cagcctccat caatggcatt     2280
aaggaattct acataaagta cgaagtttcc ggtaagactt actacgataa caacaattct     2340
gcaaactatc aagtatcaac atcaaaacct actaccacca ccgccacagc tacaactaca     2400
actgcacctt caacatctac cacaaccccca ccatcttcta cgaaccagc tacattccca     2460 actggcaatt ctactatttc tagttggatc aaaaaacaag agggtatttc cagattcgca     2520
atgttgagaa acataaatcc accaggatca gcaactggat tcatcgcagc ttctttgtcc     2580
acagcggggc cagattacta ctacgcatgg accagagatg ctgctttgac aagtaacgtt     2640
attgtttacg aatacaatac cactttgtcc ggtaacaaga ctattcttaa cgtcctaaag     2700
gattacgtta cattctctgt taagactcag tctacatcca cagtctgcaa ttgtttgggt     2760
gaaccaaagt tcaacccaga tggctctgga tacacaggtg cctggggtcg tccacaaaac     2820
gatgggcctg ccgagagagc cactacattt atcctatttg ctgactcata ccttacacaa     2880
acaaaagatg catcctacgt gactggaaca ttaaagcctg caatcttcaa agacctggat     2940
tacgttgtca acgtgtggtc taacggctgt ttcgatctat gggaagaggt taacggcgtg     3000
cacttctaca ctctaatggt catgagaaag ggtctgttgt taggtgcaga ttttgctaag     3060
agaaacggtg attctacacg tgcttctacc tactcctcaa cagcatcaac tattgcgaac     3120
aagatttctt cattttgggt ttcaagtaat aactggatac aagtatctca aagcgttaca     3180 ggggggtgtct caaaaaaggg tcttgatgtt tctacattac tggctgctaa tcttgggtct     3240
gttgatgacg gtttcttcac ccctggttct gaaaagatcc tcgctaccgc cgtcgcggtt     3300
gaggatagtt ttgcttcact ctatcctata aacaaaaacc ttccttcata cttaggaaac     3360
agtatcggta gatacccaga ggatacatac aatggtaatg gcaattcaca gggaaatcca     3420
tggttccttg ctgttacagg gtacgcagaa ctttactata gagctattaa ggaatggatc     3480
ggcaacggcg gtgtgacagt ttcctcaatc tcattgccat ttttcaaaaa gtttgactcc     3540
agcgcgacat ctggtaaaaa gtatactgtg gggacttctg atttcaacaa tttggctcaa     3600
aacattgcct tagctgccga cagattctta tctaccgtac aactccatgc acataacaat     3660
ggtagtttgg cagaggaatt tgatagaact acaggactct ctacaggtgc gagagattta     3720
acttggtcac atgcaagttt aattacagcc tcttacgcaa aggctggtgc tcctgctgca     3780
taattaatta atttaccagc ttactatcct tcttgaaaat atgcactcta tatcttttag     3840
ttcttaattg caacacatag atttgctgta taacgaattt tatgctattt ttttaatttg     3900
gagttcggtg atgaaagtgt cacagcgaat ttcctcacat gtagggaccg aattgtttac     3960
aagttctctg taccaccatg gagacatcaa agattgaaaa tctatggaaa gatatggacg     4020
gtagcaacaa gaatatagca cgagccgcgg agttcatttc gttacttttg atatcgctca     4080
caactattgc gaagcgcttc agtgaaaaaa tcataaggaa aagttgtaaa tattattggt     4140
agtattcgtt tggtaaagta gaggggggtaa ttttttcccct ttattttgtt catacattct     4200
taaattgctt tgcctctcct tttggaaagc tatacttcgg agcactgttg agcgaaggct     4260
```

```
caggccggca gcacgcagca cgctgtattt acgtatttaa ttttatatat ttgtgcatac    4320
actactaggg aagacttgaa aaaaacctag gaaatgaaaa aacgacacag gaagtcccgt    4380
atttactatt ttttccttcc ttttgatggg gcagggcgga aatagaggat aggataagcc    4440
tactgcttag ctgtttccgt ctctacttcg gtagttgtct caattgtcgt ttcagtatta    4500
cctttagagc cgctagacga tggttgagct atttgttgag ggaaaactaa gttcatgtaa    4560
cacacgcata acccgattaa actcatgaat agcttgattg caggaggctg gtccattgga    4620
gatggtgcct tattttcctt ataggcaacg atgatgtctt cgtcggtgtt caggtagtag    4680
tgtacactct gaatcaggga gaaccaggca atgaacttgt tcctcaagaa aatagcggcc    4740
ataggcatgg attggttaac cacaccagat atgcttggtg tggcagaata tagtcctttt    4800 ggtgcgcaa ttttcttgta cctgtggtag aaagggagcg gttgaactgt tagtatatat    4860
tggcaatatc agcaaatttg aaagaaaatt gtcggtgaaa aacatacgaa acacaaaggt    4920
cgggccttgc aacgttattc aaagtcattg tttagttgag gaggtagcag cggagtatat    4980
gtattccttt tttttgccta tggatgttgt accatgccca ttctga    5026
```

GLUCOAMYLASE ENGINEERED YEAST AND FERMENTATION METHODS

CROSS-REFERENCE TO RELATED APPLICATIONS

This application is a national phase application of PCT/US2019/019805, filed Feb. 27, 2019, entitled GLUCOAMYLASE ENGINEERED YEAST AND FERMENTATION METHODS, which claims the benefit of U.S. Provisional Patent Application No. 62/636,716, filed Feb. 28, 2018, entitled GLUCOAMYLASE ENGINEERED YEAST AND FERMENTATION METHODS, each of which is hereby incorporated by reference herein in its entirety.

SEQUENCE LISTING

The entire contents of the ASCII text file entitled "N00570_Sequence_Listing_ST25.txt," created on Feb. 27, 2019, and having a size of 123 kilobytes is incorporated herein by reference.

FIELD OF THE INVENTION

The current invention relates to yeast engineered with exogenous glucoamylase nucleic acids and fermentations methods for producing a bioproduct such as ethanol.

BACKGROUND

Many fermentation feedstocks are derived from plant sources (e.g., corn mash) where the carbohydrates are predominantly in the form of starch polymers. The starch polymers in such feedstocks must be treated to low molecular weight sugars that can be consumed by the yeast and used for growth and bioproduct production. Typical treatments include acid and/or enzymatic hydrolysis where the polymer chain is hydrolyzed to generate the sugars that can be used by the yeast. Starch degrading enzymes such as alpha amylases and glucoamylases can be added to convert the polymer to simple sugars. However, such enzyme additions can add significant cost and complexity to the fermentation process.

Heterologous expression and functionality of enzymes in yeast to aid in starch hydrolysis can be challenging, as it is difficult to know if the nucleic acid will be expressed properly and a functional enzyme will form, and if an active form of the enzyme will be secreted from the cell. It is also challenging to engineer yeast for growth and bioproduct production at non-optimal conditions, such as high temperatures, and in high bioproduct titers. For example, while ethanol production by fermentation is a well know industrial process, maintaining ethanol rates, titers, and yields while at the same time engineering the yeast to reduce reliance on supplemental enzymes, growth under non-optimal conditions (e.g., temperature), and minimizing by-product formation can be technically difficult. Increased ethanol concentration and accumulation of undesirable byproducts can also be detrimental to cell health.

SUMMARY OF THE INVENTION

The invention relates to engineered yeast and fermentation methods, wherein the engineered yeast are able to secrete a heterologous glucoamylase (GA) into a fermentation medium and provide glucoamylase activity (E.C. 3.2.1.3) on a fermentation substrate. The invention also relates to methods of for producing bio-derived products, such as ethanol, via fermentation using the engineered yeast.

In one aspect, experimental studies associated with the current application identified fungal glucoamylase genes that, when introduced exogenously into yeast, allowed it to grow well on feedstocks containing low glucose and high starch amounts, and produce high levels of bioproduct. The results indicated that the engineered yeast were able to secrete glucoamylase into the fermentation medium and that the glucoamylase was enzymatically active towards the starch to generate sufficient glucose for growth and bioproduct production. Other benefits associated with the disclosure include improved fermentation and bioproduct production at elevated fermentation temperatures. Yet other benefits associated with the disclosure include reduced amounts of glucose at the end of the fermentation period.

In one aspect, the invention provides an engineered yeast comprising an exogenous nucleic acid encoding a glucoamylase comprising a sequence having 81% or greater sequence identity to SEQ ID NO:1 (*Rhizopus microsporus* glucoamylase). In an embodiment, the engineered yeast is capable of producing ethanol at a rate of 1.0, 1.5, 2.0, 2.5, 3.0, 3.5, 4.0, 4.5, or 5.0 g/L*h or greater during a fermentation process. In another embodiment, the engineered yeast is capable of producing (a) at least 70 g/kg of ethanol in a fermentation medium made from a glucose polymer-containing feedstock having (i) a DE of about 50 or less. In another embodiment, the engineered yeast is capable of producing (a) 90 g/kg or greater, 120 g/kg or greater, 130 g/kg or greater, or 140 g/kg or greater of ethanol in a fermentation medium made from a glucose polymer-containing feedstock having (i) a DE of about 30. In embodiments, the amount of 70 g/kg of ethanol may be produced within 48 hours of inoculation in a fermentation medium with the feedstock. In embodiments, the glucose concentration may not be greater than 5% (wt) in the fermentation medium at the beginning (inoculation) of the fermentation process. In embodiments, the feedstock may provide an amount of glucose polymer-containing feedstock sufficient to produce 70 g/kg ethanol, for example about 20 wt % glucose-polymer feedstock in the medium. In embodiments, the feedstock may have one or more of the following properties: the feedstock is a starch hydrolysate; the glucose-polymer has predominantly α-1,4 linkages; the feedstock substantially excludes cellulosic materials (e.g., less than 20%, 15%, or 10% of cellulosic material).

In an embodiment, the yeast is capable of producing (a) at least 70 g/kg of ethanol in a fermentation medium made from corn mash having a DE of 30±2, wherein fermentation medium comprises about 32% dry weight of corn, and a pH 5.8, 35 ppm CaCl, 1900 ppm urea, 5 ppm ampicillin, wherein the staring yeast concentration is 0.1 (OD600), and fermentation is carried out at 48 hrs at 30° C. with agitation. In more specific embodiments that engineered yeast comprise a glucoamylase having 81%, 82%, 83%, 84%, 85%, 90%, 95%, 96%, 97%, 98%, or 99% or greater sequence identity to SEQ ID NO:1.

In a related embodiment, the invention provides a fermentation method for producing a bioproduct. The method comprises forming a fermentation medium from a glucose polymer-containing feedstock, and then fermenting the fermentation medium using an engineered yeast comprising an exogenous nucleic acid encoding a glucoamylase comprising a sequence having 81% or greater sequence identity to SEQ ID NO:1. Fermentation is carried out over a period to produces the bioproduct, such as ethanol.

In more specific embodiments, ethanol is produced during the fermentation period to an amount of 70 g/kg or greater, 90 g/kg or greater, 120 g/kg or greater, 130 g/kg or greater, or 140 g/kg or greater, in the fermentation medium. In some embodiments, in the fermentation method, the glucose polymer-containing feedstock has a dextrose equivalent (DE) that is not greater than 50. In some embodiments, glucose is not greater than 5 wt % of solids materials in the feedstock. Optionally, supplemental glucoamylase can be introduced into the fermentation methods to increase bioproduct titers.

In some embodiments using the engineered yeast with glucoamylase having 81% or greater sequence identity to SEQ ID NO:1 fermenting is carried out at a temperature in the range of 31° C. to 35° C. for most or all of a fermentation period.

In some embodiments using the engineered yeast with glucoamylase having 81% or greater sequence identity to SEQ ID NO:1, at the end of the fermentation period the glucose concentration in the fermentation medium of not greater than 1.0 g/L.

In another aspect, the invention provides an engineered yeast comprising an exogenous nucleic acid encoding a glucoamylase comprising a sequence having 97% or greater, or 98% or greater sequence identity to SEQ ID NO:4 (*Rhizopus delemar* glucoamylase). In an embodiment, the engineered yeast is capable of producing ethanol at a rate of 1.0, 1.5, 2.0, 2.5, 3.0, 3.5, 4.0, 4.5, or 5.0 g/L*h or greater during a fermentation process. In another embodiment, the engineered yeast is capable of producing (a) at least 70 g/kg of ethanol in a fermentation medium made from a glucose polymer-containing feedstock having (i) a DE of about 30. In embodiments, the amount of 70 g/kg of ethanol may be produced within 48 hours of inoculation in a fermentation medium with the feedstock having. In embodiments, the glucose concentration may not be greater than 5% (wt) in the fermentation medium at the beginning (inoculation) of the fermentation process. In embodiments, the feedstock may provide an amount of glucose polymer-containing feedstock sufficient to produce 70 g/kg ethanol, for example about 20 wt % glucose-polymer feedstock in the medium. In embodiments, the feedstock may have one or more of the following properties: the feedstock is a starch hydrolysate; the glucose-polymer has predominantly α-1,4 linkages; the feedstock substantially excludes cellulosic materials (e.g., less than 20%, 15%, or 10% of cellulosic material).

In a related embodiment, the invention provides a fermentation method for producing a bioproduct. The method comprises forming a fermentation medium from a glucose polymer-containing feedstock, and then fermenting the fermentation medium using an engineered yeast comprising an exogenous nucleic acid encoding a glucoamylase comprising a sequence having 97% or greater sequence identity to SEQ ID NO:4. Fermentation is carried out over a period to produces the bioproduct, such as ethanol.

In more specific embodiments of any of the preceding fermentation, ethanol is produced during the fermentation period to an amount of 70 g/kg or greater, 90 g/kg or greater, 120 g/kg or greater, 130 g/kg or greater, or 140 g/kg or greater, in the fermentation medium. In some embodiments, in the fermentation method, the glucose polymer-containing feedstock has a dextrose equivalent (DE) that is about 30. In some embodiments, glucose is not greater than 5 wt % of solids materials in the feedstock. Optionally, supplemental glucoamylase can be introduced into the fermentation methods to increase bioproduct titers.

In some embodiments using the engineered yeast with glucoamylase having 97% or greater or 98% or greater sequence identity to SEQ ID NO:4, fermenting is carried out at a temperature in the range of 31° C. to 35° C. for most or all of a fermentation period.

In some embodiments using the engineered yeast with glucoamylase having 97% or greater sequence identity to SEQ ID NO:4, at the end of the fermentation period the glucose concentration in the fermentation medium is not greater than 2.0 L, or not greater than 1.0 g/L.

In more specific embodiments of any of the preceding yeast embodiments, the engineered yeast is capable of producing 90 g/kg or greater, 120 g/kg or greater, 130 g/kg or greater, or 140 g/kg or greater of ethanol in a fermentation medium made from a glucose polymer-containing feedstock having (i) a DE of about 30.

BRIEF DESCRIPTION OF THE FIGURE

FIG. 1 shows an alignment of SEQ ID NO:1 to *Rhizopus oryzae* GA, showing the signal sequence (1-25) and starching binding domain (26-131).

DETAILED DESCRIPTION

The aspects of the present invention described below are not intended to be exhaustive or to limit the invention to the precise forms disclosed in the following detailed description. Rather a purpose of the aspects chosen and described is so that the appreciation and understanding by others skilled in the art of the principles and practices of the present invention can be facilitated.

An aspect of the invention relates to engineered yeast that expresses a glucoamylase comprising a sequence having 80%, 81%, 82%, 83%, 84%, 85%, 90%, 95%, 96%, 97%, 98%, or 99% or greater sequence identity to SEQ ID NO:1 (*Rhizopus microsporus* glucoamylase (GA)). Another aspect of the invention relates to engineered yeast that expresses a glucoamylase comprising a sequence having 97%, 98%, or 99% or greater sequence identity to SEQ ID NO:4 (*Rhizopus delemar* glucoamylase (GA)). Engineered yeast of the disclosure are able express and provide glucoamylase enzyme in the culture medium, and the glucoamylases are enzymatically active on glucose polymer substrates such as starch from various plant sources. The glucoamylase activity within the medium can generate mono and disaccharide sugars which can be consumed by the yeast and can be used as a carbon source for the production of a target compound, such as ethanol.

In embodiments of the disclosure, a fermentation medium can be prepared from a feedstock having glucose polymer and minimal glucose. For example, a fermentation medium can be prepared from a starch-containing feedstock having a DE (dextrose equivalent) of 70 or less, 60 or less, 50 or less, 40 or less, 30 or less, 20 or less, 15 or less, 10 or less, or 5 or less. Dextrose equivalent (DE) is a measure of the amount of reducing sugars present in a material (e.g., a sugar product or a starch-containing feedstock), relative to dextrose (a.k.a. glucose), expressed as a percentage on a dry basis. For example, a maltodextrin with a DE of 10 would have 10% of the reducing power of dextrose (which has a DE of 100). A fermentation medium can be prepared from a starch-containing feedstock that does not have a glucose amount that is greater than about 5% wt., or greater than about 4% wt., or greater than about 3% wt., or greater than about 2% wt., or greater than about 1% wt., per total solids in the feedstock. In some fermentation methods the low glucose-containing starch feed stock is added periodically or continuously throughout the fermentation period. The glucoamylases produced by the engineered yeast can be enzymatically active against the starch in the medium and generate glucose which can be used by the yeast for growth and generation of bioproduct. Optionally, the fermentation method can include supplementing the medium with purified glucoamylase, such as glucoamylase obtained from a commercial source, which can further drive enzymatic hydrolysis of the starch and increase growth and titers of bioproduct.

For example, without any commercial glucoamylase enzyme supplementation and using a low glucose feedstock, the engineered yeast of the disclosure can generate an amount of ethanol of about 70 g/kg or greater, such as an amount in the range of about 70 g/kg to about 115 g/kg, about 75 g/kg to about 115 g/kg, about 80 g/kg to about 115 g/kg, about 85 g/kg to about 115 g/kg, about 90 g/kg to about 115 g/kg, about 95 g/kg to about 115 g/kg, about 100 g/kg to about 115 g/kg, or about 105 g/kg to about 115 g/kg of ethanol in the fermentation medium. In embodiments wherein supplemental glucoamylase is added to the medium, greater amounts of ethanol can be produced, such as an amount of 110 g/kg or greater, or 125 g/kg or greater, or 140 g/kg or greater, in the fermentation medium.

In further embodiments, yeast engineered with glucoamylases of the disclosure can exhibit excellent fermentation performance at temperatures greater than standardly used in fermentations (i.e., fermentations at 30° C. using *Saccharomyces cerevisiae* as a host organism). For example, in some embodiments using the engineered yeast of the disclosure, fermenting is carried out at a temperature in the range of 31° C. to 35° C., or 32° C. to 34° C., for most or all of a fermentation period. Even at the higher temperatures, the engineered yeast are able to generate glucoamylase activity in the medium, and promote excellent cell growth and bioproduct production.

In further embodiments, following a period of fermentation, yeast engineered with of glucoamylases of the disclosure can provide a desirable final fermentation medium with high levels of bioproduct and low levels of byproduct. In particular, the final fermentation medium can have high levels of ethanol (e.g., 70 g/kg or greater), under stressful fermentation conditions, such as where low levels of glucose, such as 1.0 g/kg, may be present.

The term "exogenous" as used herein, means that a molecule, such as a nucleic acid, or an activity, such as an enzyme activity, is introduced into the host organism. An exogenous nucleic acid can be introduced in to the host organism by well-known techniques and can be maintained external to the hosts chromosomal material (e.g., maintained on a non-integrating vector), or can be integrated into the host's chromosome, such as by a recombination event. An exogenous nucleic acid can encode an enzyme, or portion thereof, that is either homologous or heterologous to the host organism.

The term "heterologous" refers to a molecule or activity that is from a source that is different than the referenced molecule or organism. Accordingly, a gene or protein that is heterologous to a referenced organism is a gene or protein not found in that organism. For example, a specific glucoamylase gene found in a first fungal species and exogenously introduced into a second fugal species that is the host organism is "heterologous" to the second fungal organism.

The following SEQ ID NOs are associated with the fungal GA amino acid or protein sequences: SEQ ID NO:1: *Rhizopus microsporus* GA amino acid sequence; SEQ ID NO:2: *Rhizopus microsporus* GA nucleic acid sequence #1; SEQ ID NO:3: *Rhizopus microsporus* GA nucleic acid sequence #2; SEQ ID NO:4: *Rhizopus delemar* GA amino acid sequence; SEQ ID NO:5: *Rhizopus delemar* GA nucleic acid sequence #1; and SEQ ID NO:6: *Rhizopus delemar* GA nucleic acid sequence #2.

Table 1 is a table of sequence identity (global protein alignment) between the *Rhizopus microsporus* GA amino acid sequence and GA sequence of other known GAs. The reference molecule is *Rhizopus microsporus* GA, and scoring matrix was BLOSUM 62.

TABLE 1

| GA sequence | Start | End | # Match | # Nonmatch | % Match |
|---|---|---|---|---|---|
| Rhizopus microsporus | 1 | 605 | — | — | 100 |
| Rhizopus delemar | 1 | 604 | 488 | 117 | 80 |
| Rhizopus oryzae | 1 | 604 | 485 | 120 | 80 |
| Mucor ambiguus | 1 | 609 | 416 | 194 | 68 |
| Mucor circenello | 1 | 609 | 415 | 198 | 67 |
| Choanephora cucurbitarum | 1 | 622 | 402 | 222 | 64 |
| Phycomyces blakesleeanus | 1 | 598 | 369 | 243 | 60 |
| Arthrobotrys oligospora | 1 | 621 | 204 | 441 | 31 |

*Rhizopus microsporus* GA and *Rhizopus delemar* GA are members of the glucoamylase enzyme family (E.C. 3.2.1.3) and are amylolytic enzymes that hydrolyze 1,4-linked a-D-glucosyl residues successively from the nonreducing end of oligo- and polysaccharide chains with the release of D-glucose. Alternative names for glucoamylases include amyloglucosidase; γ-amylase; lysosomal α-glucosidase; acid maltase; exo-1,4-α-glucosidase; glucose amylase; γ-1,4-glucan glucohydrolase; acid maltase; 1,4-α-D-glucan glucohydrolase.

Glucoamylases such as *Rhizopus microsporus* GA and *Rhizopus delemar* GA can also cleave α-1,6 bonds on amylopectin branching points. As used herein, the term "amylolytic activity" pertains to these enzymatic mechanisms.

Engineered yeast of the disclosure can include variant(s) of the natural sequences of the *Rhizopus microsporus* GA and *Rhizopus delemar* GA glucoamylase polypeptide and can include one or more amino acid variations, providing for a non-natural polypeptide. Polypeptides of the disclosure can be a portion of the naturally occurring *Rhizopus microsporus* GA and *Rhizopus delemar* GA sequence (such as polypeptides that are truncated at its N-terminus, its C-terminus, or both), while the glucoamylase polypeptide retains amylolytic activity.

N-terminal truncations can be produced by altering the position of the ATG start codon, while ensuring the sequence downstream remains in frame. C-terminal variants can be produced by inserting an in-frame premature stop codon. Random methods such as error-prone PCR could also be employed, and could be combined with growth on starch to ensure peptide function.

Variations in the *Rhizopus microsporus* GA (SEQ ID NO:1) and *Rhizopus delemar* GA (SEQ ID NO:4) sequences can be made with information about the primary sequence of these enzymes, through sequence alignments, and in view of information regarding other glucoamylase enzymes as known in the art. Most glucoamylases, including *Rhizopus microsporus* GA and *Rhizopus delemar* GA, are multidomain enzymes. Many glucoamylases, including *Rhizopus microsporus* GA and *Rhizopus delemar* GA, include a starch-binding domain connected to a catalytic domain via an O-glycosylated linker region, based on known crystal structures from similar enzymes.

Glucoamylases may also have a catalytic domain having a configuration of a configured twisted (alpha/alpha)(6)-barrel with a central funnel-shaped active site. Glucoamylases may have a structurally conserved catalytic domain of approximately 450 residues. In some glucoamylases the catalytic domain generally followed by a linker region consisting of between 30 and 80 residues that are connected to a starch binding domain of approximately 100 residues.

Glucoamylase properties may be correlated with their structural features. A structure-based multisequence alignment was constructed using information from catalytic and starch-binding domain models (see, e.g., Coutinho, P. M., and Reilly, P. J., 1994. Protein Eng. 7:393-400 and 749-760). It has been shown that the catalytic and starch binding domains are functionally independent based on structure-function relationship studies, and there are structural similarities in microbial glucoamylases. From other studies, specific glucoamylase residues have been shown to be involved in directing protein conformational changes, substrate binding, thermal stability, and catalytic activity (see, for example, Sierks, M. R., et al. 1993. Protein Eng. 6:75-79; and Sierks, M. R., and Svensson, B. 1993. Biochemistry 32:1113-1117).

Therefore, the correlation between glucoamylase sequence and protein function is understood in the art, and one of skill could design and express variants of amylolytically active glucoamylases having one or more amino acid deletion(s), substitution(s), and/or additions. For example, in some aspects, the glucoamylase portion of the *Rhizopus microsporus* GA and *Rhizopus delemar* GA can contain a truncated version of a naturally occurring glucoamylase, the truncated version having, in the least, a catalytic and optionally a starch-binding domain having amylolytic activity as described herein.

Truncated forms of glucoamylase have been generated and have been shown to have enzymatic activity. For example, Evans et al. (Gene, 91:131; 1990) generated a series of truncated forms of glucoamylase to investigate how much of the O-glycosylated region was necessary for the activity or stability of GAI1 a fully active form of the enzyme lacking the raw starch-binding domain. It was found that a significant portion of the C-terminus could be deleted from GAII with insignificant effect on activity, thermal stability, or secretion of the enzyme.

Lin et. al (BMC Biochemistry 8:9, 2007) teaches there was no loss of glucoamylase activity the starch binding domain located between positions 26-131 in the *Rhizopus oryzae* glucoamylase was deleted. Also, Mertens & Skory (Enz. Microbiol. Technology 40: 874-880, 2007) isolated a natural glucoamylase which lacked a starch binding domain.

Various amino acids substitutions associated with causing a change in glucoamylase activity are also known in the art. Substitution(s) of amino acid(s) at various locations in the glucoamylase sequence have been shown to affect properties such as thermo stability, starch hydrolysis activity, substrate usage, and protease resistance. As such, the current disclosure contemplates use of a *Rhizopus microsporus* GA and *Rhizopus delemar* GA sequence that includes one or more amino acids substitution(s) in the glucoamylase portion of the polypeptide, wherein the substitutions differ from the wild type sequence of the glucoamylase.

For example, U.S. Pat. No. 8,809,023 describes a method for reducing the ratio between isomaltose synthesis and starch hydrolysis activity (IS/SH ratio) during the hydrolysis of starch. In particular, a *Trichoderma reesei* glucoamylase (Tr GA) is described (total length of 632 amino acids having an N-terminal having a signal peptide) that is modified at with amino acid positions as follows: D44R and A539R; or D44R, N61I, and A539R. This glucoamylase variant is reported to exhibit a reduced IS/SH ratio compared to said parent glucoamylase during the hydrolysis of starch.

As another example, U.S. Pat. No. 8,592,194 describes glucoamylase variants with increased thermo stability compared to wild type glucoamylase variants. Also described in this disclosure is the *Trichoderma reesei* glucoamylase but instead one or more amino acid substitutions to the native Tr GA sequence at positions 10, 14, 15, 23, 42, 45, 46, 59, 60, 61, 67, 68, 72, 73, 97, 98, 99, 102, 108, 110, 113, 114, 122, 124, 125, 133, 140, 144, 145, 147, 152, 153, 164, 175, 182, 204, 205, 214, 216, 219, 228, 229, 230, 231, 236, 239, 240, 241, 242, 244, 263, 264, 265, 268, 269, 276, 284, 291, 300, 301, 303, 310, 311, 313, 316, 338, 342, 344, 346, 349, 359, 361, 364, 379, 382, 390, 391, 393, 394, 408, 410, 415, 417, and 418. As an example, the current disclosure contemplates creating variants at amino acid locations in SEQ ID NO:1 and SEQ ID NO:4 corresponding to the respective described positions in the TrGA sequence in order to provide variants with increased thermostability.

The determination of "corresponding" amino acids from two or more glucoamylases can be determined by alignments of all or portions of their amino acid sequences. Sequence alignment and generation of sequence identity include global alignments and local alignments, which typically use computational approaches. In order to provide global alignment, global optimization forcing sequence alignment spanning the entire length of all query sequences is used. By comparison, in local alignment, shorter regions of similarity within long sequences are identified.

As used herein, an "equivalent position" means a position that is common to the two sequences (e.g., a template GA sequence and a GA sequence having the desired substitution(s)) that is based on an alignment of the amino acid sequences of one glucoamylase or as alignment of the three-dimensional structures. Thus, either sequence alignment or structural alignment, or both, may be used to determine equivalence.

In some modes of practice, the BLAST algorithm is used to compare and determine sequence similarity or identity. In addition, the presence or significance of gaps in the sequence which can be assigned a weight or score can be determined. These algorithms can also be used for determining nucleotide sequence similarity or identity. Parameters to determine relatedness are computed based on art known methods for calculating statistical similarity and the significance of the match determined. Gene products that are related are expected to have a high similarity, such as greater than 50% sequence identity. Exemplary parameters for determining relatedness of two or more sequences using the BLAST algorithm can be as follows.

Inspection of nucleic acid or amino acid sequences for two nucleic acids or two polypeptides will reveal sequence identity and similarities between the compared sequences. Sequence alignment and generation of sequence identity include global alignments and local alignments which are carried out using computational approaches. An alignment can be performed using BLAST (National Center for Biological Information (NCBI) Basic Local Alignment Search Tool) version 2.2.31 software with default parameters. Amino acid % sequence identity between amino acid sequences can be determined using standard protein BLAST with the following default parameters: Max target sequences: 100; Short queries: Automatically adjust parameters for short input sequences; Expect threshold: 10; Word size: 6; Max matches in a query range: 0; Matrix: BLO- SUM62; Gap Costs: (Existence: 11, Extension: 1); Compositional adjustments: Conditional compositional score matrix adjustment; Filter: none selected; Mask: none selected. Nucleic acid % sequence identity between nucleic acid sequences can be determined using standard nucleotide BLAST with the following default parameters: Max target sequences: 100; Short queries: Automatically adjust parameters for short input sequences; Expect threshold: 10; Word size: 28; Max matches in a query range: 0; Match/Mismatch Scores: 1, −2; Gap costs: Linear; Filter: Low complexity regions; Mask: Mask for lookup table only. A sequence having an identity score of XX % (for example, 80%) with regard to a reference sequence using the NCBI BLAST version 2.2.31 algorithm with default parameters is considered to be at least XX % identical or, equivalently, have XX % sequence identity to the reference sequence.

A global alignment can align sequences with significant identity to, for example, the SEQ ID NO:1 (*Rhizopus microsporus* GA) or SEQ ID NO:4 *Rhizopus delemar* GA glucoamylase in order to determine which corresponding amino acid position(s) in the target sequence (e.g., a glucoamylase ortholog) can be substituted with the one or more of the amino acid if a glucoamylase variant is used.

In some cases, the substitution can be a conservative substitution, such as where one amino acid of a particular type (e.g., polar, non-polar/aliphatic, positively charged/basic, negatively charged/acidic) is replaced with an amino acid of the same type. Exemplary conservative amino acid substitutions of the present disclosure can involve exchange of one aliphatic or hydrophobic amino acid Ala, Val, Leu, or Ile for another; exchange of one hydroxyl amino acid Ser or Thr for the other; exchange of one acidic amino acid Asp or Glu for the other; exchange of one amide amino acid Asn or Gln for the other, exchange of one basic amino acid Lys, Arg, for His for another; exchange of one aromatic amino acid Phe, Tyr, or Trp, for another, and exchange of one small amino acids Ala, Ser, Thr, Met, or Gly for another.

In embodiments of the disclosure, SEQ ID NO:1 has one or more amino acid mutations which causes it to be less than 100% identical to SEQ ID NO:1. For example, the glucoamylase may have multiple amino acid deletion(s), substitution(s), and/or additions causing it to have about 81% or greater identity to SEQ ID NO:1, 82% or greater, 83% or greater, 84% or greater, 85% or greater, 86% or greater, 87% or greater, 88% or greater, 89% or greater, 90% or greater, 91% or greater, 92% or greater, 93% or greater, 94% or greater, 95% or greater, 96% or greater, 97% or greater, 98% or greater, or 99% or greater identity to SEQ ID NO:1. A variant with a single amino acid substitution has 99.8% identity to SEQ ID NO:1.

In exemplary embodiments, more than one location in SEQ ID NO:1 can be changed to provide a variant that has to SEQ ID NO:1 that is less than 80%. For example, changes to the signal sequence and deletion of the starch binding domain can provide a variant with less than 80% identity to SEQ ID NO:1, such as about 75%-80% identity to SEQ ID NO:1.

FIG. 1 shows an alignment of SEQ ID NO:1 to *Rhizopus oryzae* GA, showing the signal sequence (1-25) and starching binding domain (26-131).

Table 2 is a table of sequence identity (BLAST alignment) of a "core" sequence of SEQ ID NO:1 (lacking signal sequence and starch binding domain) GA sequences of other known GAs. Accession CEG69155.1 is the same sequence as SEQ ID NO:1.

TABLE 2

| Source | Accession # | Start | End | Match | NonMatch | % Match |
|---|---|---|---|---|---|---|
| *Rhizopus microsporus* | CEG69155.1 | 132 | 605 | | | |
| *Rhizopus microsporus* | ORE14155.1 | 132 | 605 | 458 | 16 | 96 |
| *Rhizopus delemar* | EIE75378.1 | 132 | 604 | 397 | 77 | 83 |
| *Rhizopus oryzae* | P07683.2 | 132 | 604 | 394 | 80 | 83 |
| *Rhizopus oryzae* | BAH09876.1 | 132 | 604 | 395 | 79 | 83 |
| *Rhizopus oryzae* | ABB77799.1 | 132 | 604 | 396 | 78 | 83 |

In embodiments of the disclosure, SEQ ID NO:4 has one or more amino acid mutations which causes it to be less than 100% identical to SEQ ID NO:4. For example, the glucoamylase may have multiple amino acid deletion(s), substitution(s), and/or additions causing it to have about 98% or greater, or 99% or greater identity to SEQ ID NO:4. A variant with a single amino acid substitution has 99.8% identity to SEQ ID NO:4.

In exemplary embodiments, one or more of locations in SEQ ID NO:1 or SEQ ID NO:4 are changed to provide a variant SEQ ID NO:1 and SEQ ID NO:4 also generally include a native "signal sequence." Various other terms may be used to indicate a "signal sequence" as known in the art, such as where the word "signal" is replaced with "secretion" or "targeting" or "localization" or "transit" or leader," and the word "sequence" is replaced with "peptide" or "signal." Generally, a signal sequence is a short amino acid stretch (typically in the range of 5-30 amino acids in length) that is located at the amino terminus of a newly synthesized protein. Most signal peptides include a basic N-terminal region (n-region), a central hydrophobic region (h-region) and a polar C-terminal region (c-region) (e.g., see von Heijne, G. (1986) Nucleic Acids Res. 14, 4683-4690).

In SEQ ID NO:1 and SEQ ID NO:4 the predicted signal sequence is from amino acid 1 to 25 of SEQ ID NO:1 and from amino acid 1 to 25 of SEQ ID NO:4, respectively. A signal sequence can target the protein to a certain part of the cell, or can target the protein for secretion from the cell. For example, it has been shown that the native N-terminal signal sequence of the *S. diastaticus* Glucoamylase STAI gene can target it to the endoplasmic reticulum of the secretory apparatus (for example, see Yamashita, I. et al., (1985) J. Bacteriol. 161, 567-573).

Glucoamylase enzymes of the disclosure can use the native signal sequences of SEQ ID NO:1 and SEQ ID NO:4, or variants thereof, or can be modified to include a heterologous signal sequences. In one aspect, the current invention provides the partial or full replacement of the native signal sequence of SEQ ID NO:1 and SEQ ID NO:4 with a secretion signal based on a sequence at the N-terminal portion of An aa, Sc FAKS, Sc AKS, Sc MFα1, Sc IV, Gg LZ, and Hs SA as described in U.S. Provisional Patent Application 62/371,681 (published as WO2018027131) and PCT Application No. PCT/US2016/016822 (published as WO2016127083), both of which are hereby incorporated by reference in their entirety.

These secretion signals can be used as a replacement to the native secretion signal of the SEQ ID NO:1 and SEQ ID NO:4, or can be used in addition to the native secretion signal. In view of the addition of the heterologous secretion signal, the proteins may be referred to as "fusion proteins," and annotated as follows: [An aa-SS]-[Rm GA], [Sc IV-SS]-[Rd GA], etc.

Possible heterologous N-terminal replacement sequences for the N-terminal of SEQ ID NO:1 and SEQ ID NO:4 include the following. Sc-FAKS is a sequence of 90 amino acids derived from the N-terminal portion of the *Saccharomyces cerevisiae* peptide mating pheromone α-factor (e.g., see Brake, A., et al., Proc. Natl. Acad. Sci., 81:4642-4646, 1984; Kurjan, J. & Herskowitz, I., Cell 30:933-943, 1982). Sc-MFα1 is amino acids 20-89 Sc-FAKS. Sc IV a 19 amino acid N-terminal signal peptide of a sucrose hydrolase enzyme (e.g, see, Carlson M., et al. (1983) Mol. Cell. Biol. 3:439-447). Gg LZ (also known as egg white lysozyme) is an 18 amino acid N-terminal signal peptide of a glycoside hydrolase enzyme (e.g, see, Jigami et al. (1986) Gene 43:273-279). Hs SA is an 18 amino acid N-terminal signal peptide of a serum (e.g, see, Kober et al. (2013) Biotechnology and Bioengineering; 110:1164-1173.). Sc MFα2 is derived from the N-terminus the *Saccharomyces cerevisiae* mating factor alpha 2 gene (Sc MFα2). Sc PHO5 is derived from the N-terminus of the *Saccharomyces cerevisiae* repressible acid phosphatase (Meyhack et al., EMBO J. 6:675-680, 1982).

Molecular techniques can be performed to create a nucleic acid sequence that is a template for the expression of genes encoding SEQ ID NO:1 or SEQ ID NO:4, or variants thereof. As a general matter, a nucleic acid is prepared to encode a protein comprising SEQ ID NO:1 or SEQ ID NO:4, or variants thereof.

In other aspects, the SEQ ID NO:1 or SEQ ID NO:4, or variants thereof optionally comprises additional sequence that is not present in the native glucoamylase polypeptide. The additional sequence, in some aspects, can provide functionality to the glucoamylase that is not present in the native polypeptide. Additional functionalities include, for example, protease sites or binding sites for other proteins or materials, or linker regions.

Nucleic acids sequences encoding SEQ ID NO:1 or SEQ ID NO:4, or variants thereof, as well as any regulatory sequence (e.g., terminator, promoter, etc.) and vector sequence (e.g., including a selection marker, integration marker, replication sequence, etc.) can, in some modes of practice, be prepared using known molecular techniques. General guidance for methods for preparing DNA constructs (e.g., for the DNA constructs including nucleic acids encoding SEQ ID NO:1 or SEQ ID NO:4 or a variant thereof) can be found in Sambrook et al Molecular Cloning, A Laboratory Manual, Cold Spring Harbor Laboratory Press, Cold Spring Harbor, N.Y., 1989; and Ausubel et al. Current Protocols in Molecular Biology, Greene Publishing and Wiley-Interscience, New York, N.Y., 1993. PCR techniques can be used for modifying nucleic acids encoding SEQ ID NO:1 or SEQ ID NO:4, to optionally introduce one or more mutations in the sequence to provide a variant.

PCR techniques are described in, for example, Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733. The techniques may optionally include site-directed (or oligonucleotide-mediated) mutagenesis, PCR mutagenesis, and cassette mutagenesis of an earlier prepared DNA encoding a glucoamylase polypeptide.

Alternatively, nucleic acid molecules can be generated by custom gene synthesis providers such as ATUM (Menlo Park, Calif.) or GeneArt (Life Technologies, Thermo Fisher Scientific).

An expression vector can be constructed to include the glucoamylase nucleic acid sequence operably linked to expression control sequences functional in the host organism. Expression vectors applicable for use in the host organisms include, for example, plasmids, episomes and artificial chromosomes. The vectors can include selection sequences or markers operable for stable integration into a host chromosome. Additionally, the vectors can include one or more selectable marker genes and appropriate expression control sequences. Selectable marker genes also can be included that, for example, provide resistance to antibiotics or toxins, complement auxotrophic deficiencies, or supply critical nutrients not in the culture medium. Expression control sequences can include constitutive and inducible promoters, transcription enhancers, transcription terminators, and the like which are well known in the art.

In some aspects, the nucleic acid can be codon optimized. The nucleic acid template can be the native DNA sequence that codes for the glucoamylase, or the template can be a codon-optimized version that is optimized for expression in a desired host cell. Databases that provide information on desired codon uses in particular host organisms are known in the art.

The DNA construct comprising the glucoamylase nucleic acid can be operably linked to a promoter sequence, wherein the promoter sequence is functional in a host cell of choice. In some aspects, the promoter shows transcriptional activity in a fungal host cell and may be derived from genes encoding proteins either homologous or heterologous to the host cell. In some aspects, the promoter is useful for expression in *S. cerevisiae*. Examples of well-known constitutive promoters include, but are not limited to the cytochrome c promoter (pCYC), translational elongation factor promoter (pTEF), the glyceraldehyde-3-phosphate dehydrogenase promoter (pGPD/TDH3), the phosphoglycerate kinase promoter (PGK), and the alcohol dehydrogenase promoter (pADH). Optionally, an additional factor that controls expression such as an enhancer or the like may also be included on the vector.

The expression vector including the glucoamylase gene can also include any termination sequence functional in the host cell. For example, the termination sequence and the promoter sequence can be from the same cell, or the termination sequence is homologous to the host cell. The termination sequence can correspond to any promoter that is used.

The DNA construct may be introduced into a host cell using a vector. The vector may be any vector which when introduced into a host cell is stably introduced. In some aspects, the vector is integrated into the host cell genome and is replicated. Vectors include cloning vectors, expression vectors, shuttle vectors, plasmids, phage particles, cassettes and the like. In some aspects, the vector is an expression vector that comprises regulatory sequences operably linked to the glucoamylase coding sequence. SEQ ID NOs as described herein can be assembled in the cell by the transformation of multiple smaller DNA fragments (e.g., "SEQ ID NO sub-fragments") with overlapping homology that in total constitute a particular SEQ ID NO. For example, the integration of a desired SEQ ID NO, or portion thereof, at a gene locus in the cell can be accomplished by the co-transformation of two to five DNA sub-fragments, which are subjected to recombination with each other and integration into a genetic locus in the cell having homology to portions of the sub-fragments.

The DNA construct comprising the glucoamylase gene can further include a selectable marker, thereby facilitating the selection in a host cell. For example, the selectable marker can be for transformed yeast. Examples of yeast selectable marker include markers commonly used for selecting for transformed yeast cells. Auxotrophic markers can be used using a gene that controls an auxotrophy, meaning that the gene enables yeast to produce a nutrient required for the growth of the yeast. Examples genes that control auxotrophies include leucine auxotrophy (LEU2), histidine auxotrophy (HIS3), uracil auxotrophy (URA3, URA5), and tryptophan auxotrophy (TRP1).

The DNA construct may be one which is integrated into the genome and replicated together with the chromosome(s) into which it has been integrated. For example, a yeast cell may be transformed with the DNA construct encoding the glucoamylase, and integrating the DNA construct, in one or more copies, in the host chromosome(s). This integration is generally considered to be an advantage, as the DNA sequence is more likely to be stably maintained. Integration of the DNA constructs into the host chromosome may be performed according to conventional methods, such as by homologous or heterologous recombination.

Engineered yeast of the disclosure can include having multiple copies (two or more) of the gene encoding SEQ ID NO:1 or SEQ ID NO:4, or variants thereof. For example, the engineered yeast can be an engineered *Saccharomyces* that has at least first, second, third, and fourth exogenous nucleic acids each including a sequence encoding at least one SEQ ID NO:1 or SEQ ID NO:4, or variants thereof. If the engineered yeast includes multiple copies of a gene encoding the glucoamylase gene, the nucleic acid sequences of the copies can be the same or different from one another. Exemplary methods and yeast strains that have been engineered to include multiple copies of glucoamylase genes are described in International Application serial no. PCT/US16/24249, filed Mar. 25, 2016 (Miller, et al.), which is hereby incorporated by reference in its entirety.

The engineered yeast can also optionally include introduction of exogenous nucleic acid sequences, changes to regulatory elements that either upregulate or down regulate expression of genes; increase in gene copy numbers, and deletions or mutations that eliminate expression, reduce expression, or increase expression or activity of a gene or gene product. The heterologous modification can include one or more of the following: the use of a promoter that is different than the native promoter of the desired gene; the use of a terminator that is different than the native terminator of the desired gene; the introduction of the gene at a location in the genome that is different than its native location; the introduction of multiple copies of the desired gene.

An additional genetic modification that can be included in the engineered yeast is the alteration or introduction of an enzyme activity that converts a low molecular weight non-glucose sugar to glucose. For example, one optional additional genetic modification affects or introduces isomaltase activity in the engineered yeast during growth on glucose. Isomaltase can convert isomaltose to glucose by hydrolyzing the 1,6 ether linkage in isomaltose. An isomaltase may also exhibit cross activity for hydrolyzing the 1,4 ether linkages in maltose. The genetic modification can cause isomaltase activity to be introduced into the cell, cause an increased amount of isomaltase in the cell, and/or cause an increase in isomaltase activity.

In some embodiments further to the glucoamylase gene, the engineered cell includes a heterologous isomaltase gene, or an isomaltase gene under the control of a heterologous promoter that provides increased expression in the cell, or present in multiple copies in the cell. For example, an isomaltase (IMA) gene under the control of a heterologous promoter, such as a PDC promoter can be engineered into the yeast.

Examples of isomaltase genes that can be introduced into an engineered yeast include, but are not limited to *Saccharomyces cerevisiae* IMA1 (P53051), *Saccharomyces cerevisiae* IMA2 (Q08295), *Saccharomyces cerevisiae* IMA3 (P0CW40), *Saccharomyces cerevisiae* IMA4 (P0CW41), *Saccharomyces cerevisiae* IMA5 (P40884), *Bacillus subtilis* malL (O06994), *Bacillus cereus* malL (P21332), *Bacillus coagulans* malL (Q45101), *Bacillus* sp. malL (P29093), etc. Preferably the isomaltase gene encodes for a polypeptide having greater than 80%, 85%, 90%, 95%, 98% or 99% sequence identity with the amino acid sequence of accession number NP 011803.3 (*Saccharomyces cerevisiae* IMA1).

In some embodiments, the engineered yeast can further include a genetic modification that provides a starch-degrading polypeptide that is different than the glucoamylase. For example, the genetic modification can be one that introduces a nucleic acid encoding a different polysaccharide-degrading enzyme, such as an exogenous or modified alpha-amylase, a betaamylase, a pullulanase, or an isoamylase. The genetic modification may also be one that increases the amount of an endogenous or an exogenous starch-degrading polypeptide in the cell, such as by placing the gene under control of a strong promoter, or providing the gene in multiple copies in the cell, such as multiple copies of the gene integrated into the genome, or multiple copies present on a non-chromosomal construct (e.g., a plasmid).

In some embodiments, the engineered yeast can further include a genetic modification that provides an exogenous or modified sugar transporter gene (such as an isomaltose transporter); See, for example, commonly assigned U.S. application Ser. No. 62/268,932 filed Dec. 17, 2015, entitled "Sugar Transporter-Modified Yeast Strains and Methods for Bioproduct Production," published as WO2017106739, which is hereby incorporated by reference in its entirety.

Various host cells can be transformed with a nucleic acid encoding SEQ ID NO:1 or SEQ ID NO:43, or a variant thereof. In some aspects, the nucleic acid including the glucoamylase gene is present in a bacterial cell. The bacterial cell can be used, for example, for propagation of the nucleic acid sequence or for production of quantities of the polypeptide.

In other aspects, the host cell is a eukaryotic cell, such as a fungal cell.

In other aspects, the heterologous glucoamylase can be purified for use in an enzyme composition, either alone or in combination with other enzymes.

In some aspects, the host cell has tolerance to a higher amount of a bioderived product, such as ethanol, in the fermentation medium. In some aspects, the host cell is an "industrial yeast" which refers to any yeasts used conventionally in ethanol fermentation. Examples include sake yeasts, shochu yeasts, wine yeasts, beer yeasts, baker's yeasts, and the like. Sake yeasts demonstrate high ethanol fermentability and high ethanol resistance and genetic stability. Typically, an industrial yeast has high ethanol resistance and preferably is viable at ethanol concentrations of 10% or greater.

In exemplary aspects, the yeast including the glucoamylase gene is a *S. cerevisiae* yeast. Some *S. cerevisiae* strains have high tolerance to ethanol. Various strains of ethanol tolerant yeast are commercially available, such as RED STAR™ and ETHANOL RED™ yeast (Fermentis/Lesaffre, USA), FALI™ (Fleischmann's Yeast, USA), SUPERSTART and THERMOSACC™ yeast (Ethanol Technology, Wis., USA), BIOFERM™ AFT and XR (NABC-North American Bioproducts Corporation, GA, USA), GERT STRAND (Gert Strand AB, Sweden), SUPERSTART™ (Alltech), ANGEL™ (Angel Yeast Ltd, China) and FERMIOL™ (DSM Specialties).

Industrial yeasts are typically prototrophic and therefore do not have an auxotrophic marker suitable for selecting for a transformant. If the yeast does not have the genetic background that would otherwise facilitate retention of the glucoamylase gene of SEQ ID NO:1 or SEQ ID NO:4, or variant thereof, within the cell upon transformation, the host cell can be engineered to introduce one or more genetic mutation(s) to establish use of a marker gene in association with and to maintain the glucoamylase gene in the cell. For example, a commercially available ethanol tolerant yeast cell can be genetically modified prior to introducing the glucoamylase gene in the cell.

A marker for a different auxotrophy can be provided by disrupting the gene that controls the auxotrophy. In one mode of practice, an ethanol tolerant strain of yeast is engineered to disrupt copies of one or more genes that control auxotrophies, such as LEU2, HIS3, URA3, URA5, and TRP1. In the case of providing uracil auxotrophy, for example, a normal ura3 gene of an ethanol tolerant yeast can be replaced with an ura3⁻ fragment obtained from a uracil auxotrophic mutant (for example, a *Saccharomyces cervisiae* MT-8 strain) to disrupt the normal ura3 gene. In the case of a ura3 gene-disrupted strain, the presence/absence of a marker can be easily identified or selected by taking advantage of the fact that a ura3 gene-disrupted strain is able to grow in a medium containing 5-fluoroorotic acid (5-FOA) while a normal ura3 strain (wild-type yeast or usual industrial yeast) is not able to grow. In the case of a lys2 gene-disrupted strain, the presence/absence of a marker can be easily identified or selected by taking advantage of the fact that a lys2 gene-disrupted strain is able to grow in a medium containing α-aminoadipic acid while a normal lys2 strain (wild-type yeast or usual industrial yeast) is not able to grow. Methods for disrupting an auxotrophy-controlling gene and for selectively separating auxotrophy-controlling gene mutants may be used depending on the auxotrophy employed. Alternatively, one can employ dominant selection markers, such as the amdS from *Aspergillus nidulans* (U.S. Pat. No. 5,876,988), which allows for growth on acetamide as the sole nitrogen source; or ARO4-OFP, which allows for growth in the presence of fluoro-phenylalanine (Fukuda et. al.). These markers can be used repeatedly using the recyclable cre-loxP system, or alternatively can be used to create auxotrophic strains that allow additional markers to be utilized.

After the host cell has been engineered to provide a desired genetic background for introduction of the glucoamylase gene, the gene construct is introduced into a cell to allow for expression. Methods for introducing a gene construct into a host cell include transformation, transduction, transfection, co-transfection, electroporation. In particular, yeast transformation can be carried out using the lithium acetate method, the protoplast method, and the like. The gene construct to be introduced may be incorporated into a chromosome in the form of a plasmid, or by insertion into the gene of a host, or through homologous recombination with the gene of a host. The transformed yeast into which the gene construct has been introduced can be selected with a selectable marker (for example, an auxotrophic marker as mentioned above). Further confirmation can be made by measuring the activity of the expressed protein.

The transformation of exogenous nucleic acid sequences including the glucoamylase gene can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The engineered yeast of the disclosure can be provided in any suitable form. In some aspects, the non-natural yeast is dehydrated to form a dry yeast composition. The dry yeast composition can have increased shelf life over wet compositions.

Fermentation using a host cell expressing the glucoamylase gene can be performed in a fermentation medium made from a feedstock derived from a starch and/or sugar containing plant material, referring to a starch and/or sugar containing plant material derivable from any plant and plant part, such as tubers, roots, stems, leaves and seeds. Starch and/or sugar comprising plant material can be obtained from cereal, such as barley, wheat, maize, rye, sorghum, millet, barley, potatoes, cassava, or rice, and any combination thereof. The starch- and/or sugar comprising plant material can be processed, such as by methods such as milling, malting, or partially malting. In some aspects, the starch material is from corn flour, milled corn endosperm, sorghum flour, soybean flour, wheat flour, biomass derived starch, barley flour, and combinations thereof. Starch-containing feedstocks used to form a fermentation medium can be made from any of these plant materials.

In some aspects, a feedstock used to form a fermentation medium includes a treated starch. For example, the fermentation medium can include a partially hydrolyzed starch. The partially hydrolyzed starch can include high molecular weight dextrins and high molecular weight maltodextrins. Collectively, starch, dextrins, maltodextrins, and any other polymerized form a glucose are glucose polymers. Partially hydrolyzed starches and preparation thereof are well known in the art. Partially hydrolyzed starches can be prepared by heating the starch with an acid such as hydrochloric or sulfuric acid at a high temperature and then neutralizing the hydrolysis mixture with a suitable base such as sodium carbonate. Alternatively, partially hydrolyzed starches can be prepared by an enzymatic process, such as by adding alpha-amylase to a starch preparation. An alpha amylase can cause the endohydrolysis of (1→4)-alpha-D-glucosidic linkages in polysaccharides containing three or more (1→4)-alpha-linked D-glucose units. A partially hydrolyzed starch product can be used that have amounts of starch and starch degradation products within desired ranges. Partially hydrolyzed starch includes preparations having minimal hydrolysis (e.g., a DE of 5, having little dextrose) to preparations having substantial hydrolysis (e.g., a DE of 95, predominantly dextrose).

The feedstock can be a "liquefact", which is corn starch that has undergone liquefaction, with a dextrose equivalents in the range of about 10 to about 15. A corn wet milling process can be used to provide steep-water, which can be used for fermentation. Corn kernels can be steeped and then milled, and separated into their major constituent fractions. Light steep water is a byproduct of the steeping process, and contains a mixture of soluble proteins, amino acids, organic acids, carbohydrates, vitamins, and minerals.

In some aspects, the feedstock can be dry grind corn, i.e., most or all of the corn kernel components are included in the fermentation feedstock. The dry-grind corn process is the most common technology for converting corn to ethanol in the U.S. Some aspects of dry-grind processing differ from the wet milling process (which uses liquefact), including, but not limited to adding urea to provide sufficient nitrogen for fermentation. The primary aspects of dry-grind processes for producing ethanol are well known in the art.

Feedstocks derived from any of the plant materials described herein generally include a "glucose polymer" which refers to those polymers including two or more glucose residues. Shorter glucose polymers including glucose dimers (e.g., maltose), trimers (e.g., triose), and those up to about 10 glucose units, which may also be referred to as "glucose oligomers." Feedstocks of hydrolyzed starch preparations with a DE in the range of about 2 to about 20 include predominantly maltodextrins, which include glucose polymers having a DP of 3 (540 Da) to over about 5000 ($10^6$ Da). For example, a starch preparation with a DE 2 includes most maltodextrins in the range of 200,000 to about 1×105 Da, and DEs in the range of about 10 to about 20 have most maltodextrins in the range of about 540 to about 100,000 Da. Degree of polymerization (DP) refers to the number of sugar monomer residues in a glucose polymer.

Based on the DE of the partially hydrolyzed starch, the concentrations (% wt) of glucose (DP 1), maltose (DP 2), triose (DP 3), and longer glucose polymers of DP 4+ can be known in the composition. Table 3 provides concentrations (% wt) of various meric forms of glucose at various DE points, as understood in the art.

TABLE 3

| DE | Glucose (DP 1) | Maltose (DP 2) | Triose (DP 3) | DP 4-6 | DP 7+ |
|---|---|---|---|---|---|
| 5 | <1 | 1 | 2 | 7 | 90 |
| 10 | <1 | 3 | 4 | 15 | 78 |
| 15 | <1 | 6 | 7 | 21 | 66 |
| 20 | <1 | 8 | 9 | 29 | 53 |
| | | | | | DP 4+ |
| 28 | 8 | 8 | 11 | | 73 |
| 36 | 14 | 11 | 10 | | 65 |
| 43 | 19 | 14 | 12 | | 55 |
| 53 | 28 | 18 | 13 | | 41 |
| 63 | 36 | 31 | 13 | | 20 |
| 66 | 40 | 35 | 8 | | 17 |
| 95 | 95 | 3 | 0.5 | | 1.5 |
| 100 | 100 | 0 | 0 | | 0 |

Benefits of the engineered yeast of the current disclosure allow use of fermentation mediums made from feedstocks with low DEs, such as feedstocks having a DE of less than about 40, less than about 30, less than about 20, less than about 15, or less than about 10. Such feedstocks may require the need for using exogenous starch-degrading enzymes to generate glucose for cell growth and bioproduct formation.

However, starch-containing feedstocks with higher DEs can be used in methods with engineered yeast of the disclosure, and the engineered yeast can still provide fermentation benefits. For example, methods of the invention may use s feedstock including partially hydrolyzed starch having a DE of not greater than about 75, or not greater than about 70, and greater than about 35, or greater than about 40, and more preferably in the range of about 45 to about 65. A DE in the range of about 45 to about 65 means that glucose is present in the feed composition in the range of about 19% to about 40% (wt), maltose in the range of about 14 to about 35% (wt), triose in the range of about 8 to about 12% (wt), and glucose polymers having a DP of 4 or greater in the range of about 17% to about 55%. The percentages are based on the total amount of all "meric" forms of glucose in the composition. Fermentation and addition of starch-containing feedstocks can be carried out to provide glucose and glucose polymer within desired ranges as expressed as a percentage of the total amount of all "meric" forms of glucose in the composition.

In aspects of the disclosure, given production and secretion of the glucoamylase from the engineered yeast into the fermentation medium, the fermentation method may omit addition of purified or enriched commercial glucoamylase into the medium, or at least allow significantly less commercial glucoamylase to be used in a fermentation method. For example, the engineered yeast of the disclosure can allow addition of commercial glucoamylase to be eliminated or at least reduced by about 50%, 60%, 70%, 80%, 90%, or 95%. 100% reduction can be attained using the yeast described herein, especially if a longer fermentation period, for example 60 hours is used. Typically, amounts of glucoamylase in the range of about 0.014-.071 AGU/g DS would be used in fermentation methods that do not use a glucoamylase-secreting engineered yeast.

The benefits of using yeast engineered to express a glucoamylase enzyme according to SEQ ID NO:1 or SEQ ID NO:4, can be understood by fermenting the yeast in a fermentation medium made from a liquified corn mash having a low DE, such as not greater than about 50, not greater than about 35, not greater than about 30, or not greater than about 25, or not greater than about 20, or not greater than about 15, such as in the range of about 2 to about 20, about 2 to about 15, or about 5 to about 5, and fermenting the medium to generate ethanol. The feedstock used to prepare the fermentation medium may optionally be described in terms of glucose concentration as an overall percentage of fermentable carbohydrates (glucose and glucose polymers) in the feedstock. For example, the fermentation medium can be made from a starch feedstock having a glucose concentration of about 2% or less, or about 1% or less, such as in the range of about 0.1% to about 2%, 0.1% to about 1.5%, or to about 0.1% to about 1%. At the end of the fermentation period, the ethanol concentration is 70 g/kg or greater in the fermentation media.

To determine if a yeast expressing a glucoamylase is capable of producing an ethanol concentration of 70 g/kg or great in the fermentation media at the end of a fermentation period, the following test can be conducted: First a fermentation medium using a starch feedstock having a DE of 30+/−2 is produced by preparing a corn mash (or liquefied corn mash) using a predetermined amount of yellow dent #2 corn that is milled and passed through a US #20 sieve. Overs (twice-ground corn that was retained on a US #20 sieve) are added back at a X:Y ratio of overs to sieved corn (0.020 overs/total corn mass ratio). The moisture content is measured by the halogen moisture balance method to determine the dry weight of the milled corn. Water is added to create a 32% slurry (w/w, dry weight basis). Concentrated sulfuric acid is added to reach a pH between 5.7-5.9. Calcium chloride dihydrate powder is added to achieve a Calcium concentration of 35 ppm. Amylase (Liquozyme™ Novozymes Liquozyme Supra 2.2×) is added based on the corn dry starch weight at a dosage ratio of 2.84 kg/ton dry basis starch dosage and the slurry is transferred to a Buchi Rotovapor R-220 flask equipped with an oil bath preset at 85° C. The reaction is allowed to proceed for 2 hours, stopping once the dextrose equivalents (DE) reaches 30+/−2 by reducing the temperature to between 34-36° C. The pH is adjusted to 5.0 with additional concentrated sulfuric acid. The DE is determined by using an osmometer (Advanced™ Model 3D3 and Precion system Model Osmette XL™) Sugar and oligocarbohydrates contents are determined using HPLC with Aminex HPX-87H column (300 mm×7.8 mm) at 60 C, 0.01N sulfuric acid mobile phase, 0.6 mL/min flow rate. To the starch feedstock a 50% urea solution and 10% ampicillin solution are added, targeting a final concentration of 1900 ppm and 5 ppm, respectively. A single fermentation typically contains 50 g of corn mash, 190 ul of 50% urea, and 2.5 ul of 10% ampicillin. A typical fermentation vessel is a baffled 250 ml shake flask fitted with an air-lock. The air lock should contain four to five milliliters of canola oil. The flask is inoculated to a starting $OD_{600}$ of 0.1, using a cell slurry made by scraping a fresh YPD plate into 1 ml of sterile water, Inoculate the fermentation medium with an engineered yeast that is ethanol tolerant (e.g., ETHANOL RED®) having an exogenous nucleic acid that expresses SEQ ID NO:1 or SEQ ID NO:4 to an $OD_{600}$ of 0.1. Fermentation is carried out in flasks at 30° C. with shaking in an orbital shaker at 100 rpm for approximately 48 hours. At 48 hours, as sample is analyzed for the concentration of ethanol, and optionally other compounds such as glucose, by high performance liquid chromatography with refractive index detector.

Without any commercial glucoamylase supplementation and using the feedstock described above, typical ethanol titers in the range of about 115 g/kg to about 135 g/kg can be observed using an engineered yeast expressing a glucoamylase of SEQ ID NO:1 or SEQ ID NO:4, or a variant thereof. Greater ethanol titers can be achieved with modifications to the yeast and/or the fermentation conditions. For example, in some embodiments wherein supplemental commercial glucoamylase is added to the medium, greater amounts of ethanol can be produced, such as an amount of 110 g/kg or greater, or 125 g/kg or greater, or 140 g/kg or greater, in the fermentation medium. In addition to the higher final ethanol titers, the fermentation rate can also be increased as free glucose may no longer be limiting the fermentation. Addition of the commercial glucoamylase further acts on starch polymers to create more glucose in the fermentation medium, resulting in increased cell growth and higher ethanol titers.

To achieve an ethanol concentration of 110 g/kg or greater in the fermentation media at the end of a fermentation period, the following test can be conducted. Prepare a starch feedstock and fermentation media as previously described. Supplement the fermentation medium with commercial glucoamylase enzyme (Spirizyme Fuel HS, Novozymes) to provide an additional glucoamylase activity in the medium. 0.097 AGU/g DS, or 30% of the dose required for the wild type can provide a benefit. Glucoamylase activity (AGU) is defined as the amount of enzyme which hydrolyzes 1 micromole maltose per minute under the standard conditions 37° C., using 23.2 mM maltose in 100 mM acetate buffer pH 4.3, using a reaction time of 5 minutes. Innoculate the fermentation medium with an engineered yeast that is ethanol tolerant (e.g., ETHANOL RED®) having an exogenous nucleic acid that expresses SEQ ID NO:1 or SEQ ID NO:4. Carry out fermentation for a period of 48 hours at 30° C. With the commercial glucoamylase supplementation and using a low glucose feedstock, typical ethanol titers in the range of about 110 g/kg to about 160 g/kg can be observed.

Test 1 is a method as described in the preceding paragraphs when done at 30° C. without commercial GA supplementation, Test 2 is a method as described in the preceding paragraphs when done at 30° C. with 0.097 AGU/g DS GA supplementation. Test 3 is a method as described in the preceding paragraphs when done at 33.3° C. without commercial GA supplementation. Test 4 is a method as described in the preceding paragraphs when done at 33.3° C. with 0.0.097DS GA supplementation. A preferred yeast is one that can produce a minimum of 70 g/kg in Test 1 AGU/g (all of the GA strains) and a minimum of 130 g/kg in test 4 (the 2×Rmic and 4×Rdel strains).

In further embodiments, following a period of fermentation, yeast engineered with of glucoamylases of the disclosure can provide a desirable final fermentation medium with high levels of bioproduct (e.g., ethanol) and low levels of byproduct. For example, the final fermentation medium can have high levels of glucose (e.g., 70 g/kg or greater, 90 g/kg or greater, 110 g/kg or greater, 125 g/kg or greater, or 140 g/kg or greater), and low levels of glucose, such as 1.0 g/kg or less (e.g., 0.9 g/kg or less, 0.8 g/kg or less, 0.7 g/kg or less, 0.6 g/kg or less, or 0.5 g/kg or less). In the final fermentation medium with high ethanol titers, low glucose is beneficial as it improves downstream processes, such as separation of components (e.g., ethanol) in the final fermentation medium.

The fermentation medium includes water and preferably includes nutrients, such as a nitrogen source (such as proteins), vitamins and salts. A buffering agent can also be present in the fermentation medium. Other components may also be present in the fermentation broth after a period of fermentation, such as fermentation products which can accumulate as the fermentation progresses, and other metabolites. Optionally, the fermentation broth can be buffered with a base such as calcium hydroxide or calcium carbonate, ammonia or ammonium hydroxide, sodium hydroxide, or potassium hydroxide in order to maintain a pH at which the organism functions well.

The fermentation medium can optionally include one or more of the following enzymes that are different than the glucoamylase of SEQ ID NO:1 or SEQ ID NO:4, or variant thereof. Exemplary other enzymes include alpha amylases, beta-amylases, peptidases (proteases, proteinases, endopeptidases, exopeptidases), pullulanases, isoamylases, cellulases, hemicellulases, endo-glucanases and related beta-glucan hydrolytic accessory enzymes, xylanases and xylanase accessory enzymes, acetolactate decarboxylases, cyclodextrin glycotransferases, lipases, phytases, laccases, oxidases, esterases, cutinases, granular starch hydrolyzing enzymes and other glucoamylases. These other enzymes can optionally be added to the fermentation medium or the starch-containing feedstock, such as by using a purified commercial preparation of the enzymes. Alternatively, one or more of the other enzymes can be secreted from the engineered yeast expressing SEQ ID NO:1 or SEQ ID NO:4, or from a different engineered cell.

The engineered yeast of the current disclosure can optionally be described in terms of the engineered yeast's specific growth rate. The growth rate of yeast can be defined by L=log(numbers) where numbers is the number of yeast cells formed per unit volume (mL), versus T (time).

The fermentation is carried out under conditions so that fermentation can occur. Although conditions can vary depending on the particular organism and desired fermentation product, typical conditions include a temperature of about 20° C. or greater, and more typically in the range of about 30° C. or greater. During fermentation the reaction mixture can be mixed or agitated. In some modes of practice, the mixing or agitation can occur by the mechanical action of sparging gas to the fermentation broth. Alternatively, direct mechanical agitation such as by an impellor or by other means can be used during fermentation.

The disclosure also provides non-natural yeast that have the ability to grow, and/or can produce a fermentation product at temperatures that are greater than those in which yeast, such as *Saccharomyces cerevisiae*, typically are used in fermentation processes. For example, *S. cerevisiae* typically have optimal growth at a temperature of about 30° C. However, engineered yeast of the disclosure can grow and provide excellent bioproduct (e.g., ethanol) titers at higher temperatures, and can also provide low residual glucose. For example, in some embodiments using the engineered yeast of the disclosure, fermenting is carried out at a temperature in the range of 31° C. to 35° C., or 32° C. to 34° C., for most or all of a fermentation period. Even at the higher temperatures, the engineered yeast are able to generate glucoamylase activity in the medium, and promote excellent cell growth and bioproduct production.

During a fermentation process the fermentation medium can reach an elevated temperature such as about 32° C. or about 32° C. or greater during one or more time(s) during the fermentation process. The temperature can be elevated during part of the fermentation period, or during the entire fermentation period. The temperature can be elevated for 5 minutes of greater, 10 minutes of greater, 30 minutes or greater, 1 hour or greater, 2 hours or greater, 5 hours or greater, or 10 hours or greater. The time of elevated temperature can also be expressed as a total of the overall fermentation period, such as about 0.1% to 100%, about 0.1% to about 75%, about 0.1% to about 50%, about 0.1% to about 25%, about 0.1% to about 10%, about 0.1% to about 5%, about 0.1% to about 2.5%, about 0.1% to about 1%, or about 0.1% to about 0.5% of the fermentation period.

The engineered yeast can also provide a commercially relevant titer of ethanol during or after the period of elevated temperature. For example, during or after the period of elevated temperature, for example, the ethanol titer can be in the range of about 110 g/L to about 170 g/L, in the range of about 125 g/L to about 170 g/L, or in the range of about 140 g/L to about 170 g/L. Accordingly, the engineered yeast described herein can produce ethanol at a commercially useful titer during or after a period of high temperature that would typically cause issues in other currently available yeast strains used in ethanol-producing fermentation processes. Such issues include but are not limited to: death to a significant percentage of yeast cells; deleterious effects on the ability of the yeast to reproduce; and/or reduction or elimination of the ability of the yeast to produce a fermentation product.

Miller et al. (both WO2016127083, filed Feb. 6, 2015, and PCT/US17/045493, filed Aug. 4, 2017, which are hereby incorporated by reference in their entirety) describes the utility of swapping the leader sequence on several glucoamylases, but also highlights the need for additional modifications to the host to achieve acceptable ethanol/glucose titers at the elevated temperatures. Specifically, Miller describes the effect of expressing the Mfalpha2-*R. oryzae* GA on ethanol and residual glucose titers at two different temperatures, 30° C. and 33.3° C. Temperature is a well-known antagonist to healthy ethanol fermentations, and producers spend a significant amount of capital and operating cost in terms of cooling capacity to keep their fermenters in the safe zone, typically less than 34° C. Heterologous protein production is also a well described stressor in engineered organisms, as energy directed towards cell growth and maintenance is diverted to non-natural production processes as described in Mattanovich et. al (Journal of Biotechnology 113, 2004). Alleviating the burden of heterologous protein production has been an area of intense focus over the past several decades, in all aspects of biotechnology (e.g. pharma, industrial enzymes, etc), and is not limited to the yeast *Saccharomyces cerevisiae*. Classical techniques and targeted pathway engineering, two primary methods to overcome the obstacles of producing protein and maintaining healthy host performance have resulted in some success (Payne et. al 2008, Gasser et. al 2007, Valkonen et. al 2003). These results also indicate that there is no one solution to the problem, and a solution for one protein may not work for another.

In some cases, fermentation is carried out in industrial capacity fermenters in order to achieve commercial scale economic benefits and control. In an aspect, the fermentation is carried out in a fermenter that has a capacity of about 10,000 liters or more.

The pH of the fermentation medium can be adjusted to provide optimal conditions for glucoamylase activity, cell growth, and fermentation activity to provide a desired product, such as ethanol. For example, pH of the solution can be adjusted to in the range of 3 to 5.5. In one mode of practice, the pH of the fermentation medium is in the range of 4 to 4.5.

As noted above, the present fermentation process using genetically modified yeast expressing SEQ ID NO:1 or SEQ ID NO:4, or a variant thereof, and capable of secreting the enzyme produced into the fermentation medium. These enzymes are therefore directly exposed to the broth conditions and affect the carbohydrate composition in the fermentation medium. In the fermentation medium the glucoamylase can cause hydrolysis and release of D-glucose from the non-reducing ends of the starch or related oligo- and polysaccharide molecules by cleaving alpha(1,4) and alpha-(1,6) glucosidic bonds.

Starch may also be acted on by one or more other amylases (e.g., alpha-amylase) present in the fermentation medium. For example, if alpha-amylase is present in the fermentation medium it can cause partial hydrolysis of precursor starch and cause a partial breakdown of the starch molecules by hydrolyzing internal alpha-(1,4)-linkages.

In some modes of practice, the fermentation is carried out as a single batch until completion. In other modes of practice, the fermentation is carried out as a fed batch fermentation process. In this mode of practice, a first portion of a total amount of starch material to be fermented is added to the fermentation medium wherein the glucoamylase enzyme acts on the starch to cause formation of glucose to be used as a substrate for fermentation. Additional starch material can be added in one or more portions to provide more substrate for the glucoamylase enzyme in the medium. The addition of starch can be regulated and the formation of glucose can be monitored to provide efficient fermentation.

In some modes of practice, the fermentation is carried out in a continuous mode of operation. In this mode, multiple fermenters operate in series in which a starch hydrolysate is supplied in the first fermenter, which is fed to second fermenter and so on until the starch hydrolysate is converted to ethanol. Continuous operation can be operated using between 2-7 fermenters.

In some modes of practice, a portion of the total amount of starch material is added to the fermentation broth using a variable rate addition system. Examples of such systems include a variable speed pump or a metering valve (such as a throttle valve) operably connected to a pump, which pump or valve can be utilized to vary the amount of starch material introduced into the fermentation broth over time. In some modes of practice, during the addition of a portion of the starch material, glucose concentration is monitored by a real-time monitoring system.

Real-time monitoring systems include systems that directly monitor glucose concentration and systems that indirectly monitor glucose concentration. Examples of real-time monitoring systems that typically directly monitor glucose concentration include systems based on infrared (IR) spectroscopy, near-infrared (NIR) spectroscopy systems, Fourier transform infrared (FTIR) systems, systems based on refractive index, automated enzyme based measurement systems such as a YSI 2950 Biochemistry Analyzer sold by YSI Life Sciences systems, high performance liquid chromatography (HPLC) based systems, gas chromatography (GC) based systems, and other real-time monitoring systems known to one of skill in the art. Additionally real-time monitoring systems that indirectly monitor/measure the glucose concentration of a fermentation process can be developed by determining the typical carbon distribution in a particular fermentation process and correlating the glucose concentration present in the fermentation broth to another parameter exhibited by the fermentation, such as, for example, a correlation of the glucose level present in the fermentation broth with a measurement of the carbon dioxide evolution rate and the amount of carbon dioxide present in an off-gas stream from the fermentation vessel. The carbon dioxide can be readily measured through use of a mass spectrometer or other suitable instrumental technique for measuring the components of the off-gas stream. In a preferred aspect, the glucose concentration is monitored by a real-time monitoring system using infrared spectroscopy. In another one aspect, the glucose concentration is monitored by a real-time monitoring system using near-infrared spectroscopy. The real time monitoring systems interface with equipment that controls the introduction of starch material into the fermentation broth to modulate the formation of glucose to a desired concentration in the fermentation broth.

During the fermentation process a sample of the fermentation medium can be taken to determine the amount of glucoamylase activity in the medium. The amount of glucoamylase activity in the medium can be referred to as extracellular glucoamylase activity as it corresponds to glucoamylase secreted from the engineered yeast. In some modes of measuring, the amount of glucoamylase activity in the medium can be determined by the amount of glucoamylase activity per amount of biomass per volume of medium.

Measuring the glucoamylase activity in the fermentation medium can be another way of reflecting the benefits of using yeast engineered to express a glucoamylase enzyme according to SEQ ID NO:1 or SEQ ID NO:4. Such a test can be carried out by using a fermentation medium made from a low DE feedstock, high DE feedstock, or anything in between. During the fermentation process a sample of medium is taken and the biomass amount and the enzyme activity are determined. As used herein "biomass" refers to the weight of the engineered yeast, which can be measured in grams of dried cell weight per liter of medium (DCW/L).

In some modes of practice, the fermentation period is about 30 hours or greater, about 40 hours or greater, about 50 hours or greater, or about 60 hours or greater, such as a period of time in the range of about 40 to about 120 hours, or 50 to about 110 hours.

The fermentation product (also referred to herein as a "bio-derived product" or "bioproduct") can be any product that can be prepared by enzymatic degradation of a starch material by the glucoamylase, formation of glucose, and fermentation of glucose. In some aspects, the fermentation product is selected from the group consisting of: amino acids, organic acids, alcohols, diols, polyols, fatty acids, fatty acid alkyl esters (such as fatty acid methyl or ethyl esters (for example C6 to C12 fatty acid methyl esters (preferably C8 to C10 fatty acid methyl esters))), monoacyl glycerides, diacyl glycerides, triacyl glycerides, and mixtures thereof. Preferred fermentation products are organic acids, amino acids, fatty acid alkyl esters (such as fatty acid methyl esters (for example C8 to C12 fatty acid methyl esters (preferably C8 to C10 fatty acid methyl esters))), and their salts thereof, and especially where the organic acid is selected from the group consisting of hydroxyl carboxylic acids (including mono-hydroxy and dihydroxy mono-, di-, and tri-carboxylic acids), monocarboxylic acids, dicarboxylic acids, and tricarboxylic acids and mixtures thereof. Examples of fermentation products that are prepared by the present process are organic acids or amino acids such as lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, acetic acid, methyl hexanoate, methyl octanoate, methyl nonanoate, methyl decanoate, methyl dodecanoate, ethyl hexanoate, ethyl octanoate, ethyl nonanoate, ethyl decanoate, ethyl dodecanoate, and mixtures thereof and derivatives thereof and salts thereof. In a preferred aspect, a fermentation method of the disclosure produces ethanol as the bioproduct.

The fermentation product can have an excellent ratio of bioproduct (e.g., ethanol) to residual glucose, which is beneficial as it improves downstream processes, such as separation of components (e.g., ethanol) in the final fermentation medium. For example, the amount of glucose in the fermentation medium is 1.0 g/kg or less, 0.9 g/kg or less, 0.8 g/kg or less, 0.7 g/kg or less, 0.6 g/kg or less, 0.5 g/kg or less, 0.4 g/kg or less, 0.3 g/kg or less, or 0.2 g/kg or less, such as a glucose amount in the range of about 0.05 g/kg to about 1.0 g/kg, or about 0.05 g/kg to about 0.5 g/kg. The final fermentation medium can have an ethanol:glucose (wt/wt) ratio of about 70:1 (wt/wt) or greater, about 100:1 (wt/wt) or greater, about 150:1 (wt/wt) or greater, about 200:1 (wt/wt) or greater, about 250:1 (wt/wt) or greater, or about 300:1 (wt/wt) or greater, such as in the range of about 75:1 (wt/wt) to about 750:1 (wt/wt), or about 100:1 (wt/wt) to about 500:1 (wt/wt).

The fermentation product is recovered from the fermentation broth. The manner of accomplishing this will depend on the particular product. However, in some modes of practice, the organism is separated from the liquid phase, typically via a filtration step or centrifugation step, and the product recovered via, for example, distillation, extraction, crystallization, membrane separation, osmosis, reverse osmosis, or other suitable technique.

The present process provides the ability to make fermentation products on a production scale level with excellent yields and purity. In an aspect, the process is carried out in fermentation broth quantities of at least 25,000 gallons. In an aspect, the batch process is carried out in to produce batches of at least 25,000 gallons of final fermentation broth. In some aspects the process is a continuous process, performed in vessels of at least 200,000 gallons.

In some aspects, a genetically modified yeast expressing SEQ ID NO:1 or SEQ ID NO:4, or a variant thereof, can be used for conversion processes, such as for the production of dextrose for fructose syrups, specialty sugars and in alcohol and other end-product (e.g., organic acid, ascorbic acid, and amino acids). Production of alcohol from the fermentation of starch substrates using glucoamylases of the disclosure can include the production of fuel alcohol or potable alcohol.

Ethanol mass yield can be calculated by dividing the ethanol concentration by the total glucose consumed. Since glucose can be present as free glucose or tied up in oligomers, one needs to account for both. To determine the total glucose present at the beginning and end of fermentation, a total glucose equivalents measurement is determined. Total glucose equivalence measurement is as follows. Glucose is measured with HPLC using RI detection. Separation is completed with a Bio Rad 87H column using a 10 mM H2SO4 mobile phase. Glucose is measured in triplicate for each sample. An acid hydrolysis is performed in triplicate in 6% (v/v) trifluoroacetic acid at 121° C. for 15 minutes. The resulting glucose after hydrolysis is measured by the same HPLC method. The total glucose equivalents present in each sample is the amount of glucose measured after acid hydrolysis. The total glucose consumed is calculated by subtracting the total glucose equivalents present at the end of fermentation from the total glucose equivalents present at the beginning of the fermentation.

Use of the engineered yeast of the current disclosure may also provide benefits with regards to increased titers, reduced volatile organic acids (VOCs), and reduced fusel oil compounds (volatile organic acids, higher alcohols, aldehydes, ketones, fatty acids and esters).

The fermentation product may be first treated with one or more agents via a treatment system. The treated fermentation product can then be sent to a distillation system. In the distillation system, the fermentation product can be distilled and dehydrated into ethanol. In some aspects, the components removed from the fermentation medium include water, soluble components, oil and unfermented solids. Some of these components can be used for other purposes, such as for an animal feed product. Other co-products, for example, syrup can be recovered from the stillage.

The present disclosure also provides a method for the production of a food, feed, or beverage product, such as an alcoholic or non-alcoholic beverage, such as a cereal- or malt-based beverage like beer or whiskey, such as wine, cider, vinegar, rice wine, soya sauce, or juice, said method comprising the step of treating a starch and/or sugar containing plant material with a composition as described herein. In another aspect, the invention also relates to a kit comprising a glucoamylase of the current disclosure, or a composition as contemplated herein; and instructions for use of said glucoamylase or composition. The invention also relates to a fermented beverage produced by a method using the glucoamylase.

After the fermentation process is complete, materials present in the fermentation medium can be of use. In some aspects, after a fermentation process has been completed, or while a fermentation process is ongoing, some or all of a bioproduct can be removed from the fermentation medium to provide a refined composition comprising non-bioproduct solids. The non-bioproduct solids can include the non-natural yeast, feedstock material in the medium that is not utilized by the yeast, as well as fermentation co-products. These materials can provide sources of carbohydrates and proteins that are useful as supplements to improve the nutritional content of a feed composition. The feed material can be a co-product from a fermentation process such as stillage (whole stillage, thin stillage, etc.) or composition prepared therefrom including dried distillers grains (DDG), distillers dry grains with solubles (DDGS), distillers wet grains (DWG), and distillers solubles (DS).

A fermentation medium, optionally with some or all of the target bioproduct removed, can be further treated, such as to remove water, or to cause precipitation or isolation of the non-bioproduct solids from the medium. In some cases the medium is treated by freeze drying or oven drying. After treatment the refined composition may be in the form of, for example, a liquid concentrate, a semi-wet cake, or a dry solid. The refined composition can be used as a feed composition itself, or an ingredient in the preparation of a feed composition. In preferred preparations, the feed composition is a livestock feed composition such as for sheep, cattle, pigs, etc.

The solids in the fermentation medium can provide a source of one or more amino acids. Introduced into an animal feed, the fermentation co-product can provide an enhanced amino acid content with regard to one or more essential amino acids. Essential amino acids can include histidine, isoleucine, lysine, methionine, phenylalanine, threonine, and tryptophan. These amino acids can be present in the feed composition as free amino acids or can be derived from proteins or peptides rich in the amino acids. The solids in the fermentation medium can provide a source of one or more prebiotics, which are nondigestible food substances, such as nondigestible oligosaccharides, that selectively stimulate the growth of favorable species of bacteria in the gut, thereby benefitting the host. The solids in the fermentation medium can provide a source of phytases, β-glucanases, proteases, and xylanases.

Table 4 includes strains used in the experimental studies associated with the disclosure.

TABLE 4

| Strain ID | Strain Description |
| --- | --- |
| Strain 1 | Wild Type |
| Strain 1-1 | Ura3Δ |
| Strain 1-2 | 2X Mfa2-*R. oryzae* GA |
| Strain 1-3 | 4X Mfa-*R. oryzae* GA |
| Strain 1-4 | 1X *R. microsporus* GA |
| Strain 1-5 | 2X *R. microsporus* GA |
| Strain 1-6 | 2X *R. microsporus* GA |
| Strain 1-7 | 4X *R. microsporus* GA |
| Strain 1-8 | 2X *R. delemar* GA |
| Strain 1-9 | 4X *R. delemar* GA |

Example 1

Screening a Diverse Library of Glucoamylase Enzymes for Growth on Starch

Heterologous expression of a functional glucoamylase in *Saccharomyces cerevisiae* was first demonstrated circa 1993, using the *Aspergillus niger* glucoamylase. Other uses of glucoamylase in *Saccharomyces cerevisiae* have been reported, but still represent only a very small fraction of the number of public sequence information for these proteins. To that aim, over 1,000 enzymes were expressed and tested from a diverse set of organisms to identify enzymes that confer the desired trait of high glucoamylase expression while maintaining ethanol rate, titer, and yield.

A DNA library was constructed containing 1037 genes encoding glucoamylases, alpha-amylases, amylopullulanases, or other starch hydrolyzing enzymes by cloning synthetically created open reading frames into a *Saccharomyces cerevisiae* episomal plasmid. The enzymes encoded by these genes were sourced from four distinct classes including: 1) enzymes that were annotated with a glucoamylase EC number (which included both glucoamylases and a-amylases), 2) enzymes that were annotated as having both α-1,6 and α-1,4 glycosidase activity 3) structural homologs of previously identified functional fungal glucoamylases expressed in *Saccharomyces cerevisiae*, and finally 4) starch hydrolyzing enzymes from ruminant gut microbiomes. Each enzyme in the library was screened with its native leader as well as one substituted with the *Saccharomyces cerevisiae* Mfα2 leader. In total, 1,773 plasmids were successfully transformed into Strain 1-1 (described in previous application). Resulting transformants were tested for growth on starch containing media, using iodine staining to reveal zones of clearing. A total of 245 strains were able to produce zones of clearing, indicating that they contained plasmids with genes encoding heterologous enzymes capable of generating starch hydrolyzing activity when expressed in a yeast. These 245 were further screened for ethanol production as described below. The remaining genes encoded by the remaining 1528 plasmids were deemed not to be sufficiently active to warrant further testing.

Secondary Screening for Ethanol Production in Deep Well Microtiters

Ethanol production was measured using deep well microtiter plates containing 0.5 mL of media. The fermentation medium consists of 725 g partially hydrolyzed corn starch in the form of liquifact, 150 g filtered light steep water, 125 g sterile water, 25 g glucose, and 1 g urea. Partially hydrolyzed corn starch is provided by Cargill's Eddyville, Iowa corn wet mill (DS 30-37%, DE 5-15). Light steep water is also provided from Cargill's Eddyville, Iowa corn wet mill (free available nitrogen 2000-2500 ppm). Light steep water is centrifuged at 8,000 RPM, and the resulting supernatant is filter sterilized using 0.2 micron filters to produce filtered light steep water. Strains are inoculated to an $OD_{600}$ of 0.1 and the plate is incubated at 30° C. with shaking in an orbital shake at 1000 rpm. Samples are taken and analyzed for relevant metabolite concentrations at the end of fermentation by HPLC.

Selected results from the screening of the 245 strains is shown in Table 5. Most of the strains did not demonstrate commercially relevant ethanol titers (e.g., *Aspergillus kawachii, Aspergillus terreus, Thermomyces lanuginosus,* and Mfα2-*Neurospora crassa* are representative of such strains). However, two strains (*Rhizopus delemar* and *Rhizopus microspores*) demonstrated ethanol titers greater than commercially relevant strains known in the art (Mfα2-*Rhizopus oryzae* and *Saccharomycopsis fibuligera*).

TABLE 5

| Enzyme Source, Accession # | SEQ ID NO | Ethanol titer (g/L) at 61.25 hours |
|---|---|---|
| *Rhizopus delemar*, I1BGP8 | SEQ ID NO 7 | 100.08 |
| *Rhizopus microsporus*, A0A0C7BD37 | SEQ ID NO 8 | 107.82 |
| Mfα2-*Rhizopus oryzae*, Q2VC81 | SEQ ID NO 9 | 99.50 |
| *Saccharomycopsis fibuligera*, Q8TFE5 | SEQ ID NO 10 | 89.64 |

TABLE 5-continued

| Enzyme Source, Accession # | SEQ ID NO | Ethanol titer (g/L) at 61.25 hours |
|---|---|---|
| *Aspergillus kawachii*, G7XVA6 | SEQ ID NO 11 | 33.70 |
| *Aspergillus terreus*, Q0CPK9 | SEQ ID NO 12 | 34.20 |
| *Thermomyces lanuginosus*, Q58HN1 | SEQ ID NO 13 | 35.00 |
| Mfα2-*Neurospora crassa*, A0A0B0E9D9 | SEQ ID NO 14 | 37.90 |

Example 2

Construction of Strains Expressing the MFalpha2-*R. oryzae* GA.

Creation of a ura3Δ auxotrophic base strain is previously described in (CAR0233P1 Strain 1-3), referred to as Strain 1-1 herein. Strain 1-1 is transformed with SEQ ID NO: 15 and SEQ ID NO: 16. SEQ ID NO: 15 contains the following elements: homology to integration locus A (3986 bp), a ScTDH3 promoter (992-1673 bp), a *Rhizopus oryzae* glucoamylase with modified signal sequence (1680-3476 bp), a ScCYC1 terminator (3485-3708 bp), a loxP recombination site (3717-3750 bp), a ScURA3 promoter (3751-4257 bp), the upstream portion of the ScURA3 (4258-4861 bp). SEQ ID NO: 16 contains the following elements: downstream portion of the ScURA3 (7-606 bp), a ScURA3 terminator (607-927 bp), a loxP recombination site (928-961 bp), a ScPGK1 promoter (968-1554 bp), a *Rhizopus oryzae* glucoamylase with modified signal sequence (1561-3357 bp), a ScGAL10 terminator (3366-3836 bp), and homology to integration locus A (3838-4748 bp). Transformants are selected on synthetic complete media lacking uracil. (ScD-Ura). Resulting transformants are streaked for single colony isolation on ScD-Ura. A single colony is selected. Correct integration of SEQ ID NO: 15 and SEQ ID NO: 16 into one allele of integration locus A is verified by PCR in the single colony. A PCR verified isolate is designated Strain 1-2 (yNS220).

Strain 1-2 is transformed with SEQ ID NO: 17, 18 and 19. SEQ ID NO: 17 contains the following elements: homology to integration locus A (3-986 bp), a ScTDH3 promoter (9921673 bp). SEQ ID NO: 18 contains the following elements: a ScTDH3 promoter (6-687 bp), a *Rhizopus oryzae* glucoamylase with modified signal sequence (694-2490), a ScCYC1 terminator (2499-2722 bp), a loxP recombination site (2731-2674 bp), a ScTEF1 promoter (2765-3220 bp), and the upstream portion of the *Aspergillus nidulans* acetamidase (3221-4260). SEQ ID NO: 19 contains the following elements: the downstream portion of the *Aspergillus nidulans* acetamidase (7-1032 bp), a ScADH1 terminator (1033-1335 bp), a loxP recombination site (1336-1369 bp), a ScPGK1 promoter (1376-1962 bp), a *Rhizopus oryzae* glucoamylase with modified signal sequence (1969-3765 bp), a ScGAL10 terminator (3774-4244 bp), and homology to integration locus A (4246-5008 bp). Transformants are selected on Yeast Nitrogen Base (without ammonium sulfate or amino acids) containing 20 g/L glucose and 1 g/L acetamide as the sole nitrogen source. Resulting transformants are streaked for single colony isolation on Yeast Nitrogen Base (without ammonium sulfate or amino acids) containing 20 g/l glucose and 1 g/L acetamide as the sole nitrogen source. A single colony is selected. Correct integration of SEQ ID NO 17, 18 and 19 into the second allele of locus A is verified by PCR in the single colony. A PCR verified isolate is designated Strain 1-3.

Example 3

Construction of Strains Expressing the *Rhizopus microsporus* GA.

Strain 1-1 is transformed with SEQ ID NO: 20 and SEQ ID NO: 21. SEQ ID NO: 20 contains the following elements: homology to integration locus A (3-986 bp), a ScTDH3 promoter (992-1673 bp), a *Rhizopus microsporus* glucoamylase (1680-3497 bp), a ScCYC1 terminator (3506-3729 bp), a loxP recombination site (3738-3771 bp), a ScURA3 promoter (3772-4278 bp), the upstream portion of the ScURA3 (4279-4882 bp). SEQ ID NO: 21 contains the following elements: A portion of the ScURA3 promoter (11-446), a ScURA3 (447-1250 bp), a ScURA3 terminator (1251-1570 bp), a loxP recombination site (1571-1604 bp), and homology to integration locus A (1613-1790 bp). Transformants are selected on synthetic complete media lacking uracil. (ScD-Ura). Resulting transformants are streaked for single colony isolation on ScD-Ura. A single colony is selected. Correct integration of SEQ ID NO: 20 and SEQ ID NO: 21 into one allele of integration locus A is verified by PCR in the single colony. A PCR verified isolate is designated Strain 1-4.

Strain 1-4 is transformed with SEQ ID NO: 22 and SEQ ID NO: 23. SEQ ID NO: 22 contains the following elements: homology to integration locus A (1-193 bp), a ScTDH3 promoter (199-880 bp), a *Rhizopus microsporus* glucoamylase (887-2704 bp), a ScCYC1 terminator (2713-2936 bp), a loxP recombination site (2945-2978 bp), a ScTEF1 promoter (2979-3434 bp), and the upstream portion of the *Aspergillus nidulans* acetamidase (3435-4474 bp). SEQ ID NO 23 contains the following elements: the downstream portion of the *Aspergillus nidulans* acetamidase (1-1498 bp), a ScTEF1 terminator (1499-1658 bp), a loxP recombination site (1692-1659 bp), and homology to integration locus A (1701-1878). Transformants are selected on Yeast Nitrogen Base (without ammonium sulfate or amino acids) containing 20 g/L glucose and 1 g/L acetamide as the sole nitrogen source. Resulting transformants are streaked for single colony isolation on Yeast Nitrogen Base (without ammonium sulfate or amino acids) containing 20 g/l glucose and 1 g/L acetamide as the sole nitrogen source. A single colony is selected. Correct integration of SEQ ID NO: 22 and SEQ ID NO: 23 into the second allele of locus A is verified by PCR in the single colony. A PCR verified isolate is designated Strain 1-5.

Strain 1-1 is transformed with SEQ ID NO: 20 and SEQ ID NO: 24. SEQ ID NO: 24 contains the following elements: downstream portion of the ScURA3 (7-606 bp), a ScURA3 terminator (607-927 bp), a loxP recombination site (928-961 bp), a ScPGK1 promoter (9681554 bp), a *Rhizopus microsporus* glucoamylase (1561-3378 bp), a ScGAL10 terminator (3387-3857 bp), and homology to integration locus A (3859-4823 bp). Transformants are selected on synthetic complete media lacking uracil. (ScD-Ura). Resulting transformants are streaked for single colony isolation on ScD-Ura. A single colony is selected. Correct integration of SEQ ID NO: 20 and SEQ ID NO: 24 into one allele of integration locus A is verified by PCR in the single colony. A PCR verified isolate is designated Strain 1-6.

Strain 1-6 is transformed with SEQ ID NO: 22 and SEQ ID NO: 25. SEQ ID NO: 25 contains the following elements: the downstream portion of the *Aspergillus nidulans* acetamidase (7-1032 bp), a ScADH1 terminator (1033-1335 bp), a loxP recombination site (1336-1369 bp), a ScPGK1 promoter (1376-1962 bp), a *Rhizopus microsporus* glucoamylase (1969-3786 bp), a ScGAL10 terminator (3795-4265 bp), and homology to integration locus A (4267-4684 bp). Transformants are selected on Yeast Nitrogen Base (without ammonium sulfate or amino acids) containing 20 g/L glucose and 1 g/L acetamide as the sole nitrogen source. Resulting transformants are streaked for single colony isolation on Yeast Nitrogen Base (without ammonium sulfate or amino acids) containing 20 g/l glucose and 1 g/L acetamide as the sole nitrogen source. A single colony is selected. Correct integration of SEQ ID NO: 22 and SEQ ID NO: 25 into the second allele of locus A is verified by PCR in the single colony. A PCR verified isolate is designated Strain 1-7.

Example 4

Construction of Strains Expressing the *Rhizopus delemar* GA.

Strain 1-1 is transformed with SEQ ID NO: 26 and SEQ ID NO: 27. SEQ ID NO: 26 contains the following elements: homology to integration locus A (3-986 bp), a ScTDH3 promoter (992-1673 bp), a *Rhizopus delemar* glucoamylase (1698-3494 bp), a ScCYC1 terminator (3503-3726 bp), a loxP recombination site (3735-3768 bp), a ScURA3 promoter (3769-4275 bp), the upstream portion of the ScURA3 (4276-4879 bp). SEQ ID NO: 27 contains the following elements: downstream portion of the ScURA3 (7-606 bp), a ScURA3 terminator (607-927 bp), a loxP recombination site (928-961 bp), a ScPGK1 promoter (968-1554 bp), a *Rhizopus delemar* glucoamylase (1561-3375 bp), a ScGAL10 terminator (3384-3854 bp), and homology to integration locus A (3856-4820). Transformants are selected on synthetic complete media lacking uracil. (ScD-Ura). Resulting transformants are streaked for single colony isolation on ScDUra. A single colony is selected. Correct integration of SEQ ID NO: 26 and SEQ ID NO: 27 into one allele of integration locus A is verified by PCR in the single colony. A PCR verified isolate is designated Strain 1-8.

Strain 1-8 is transformed with SEQ ID NO: 28 and SEQ ID NO: 29. SEQ ID NO: 28 contains the following elements: homology to integration locus A (1-986 bp), a ScTDH3 promoter (992-1673 bp), a *Rhizopus delemar* glucoamylase (1680-3494 bp), a ScCYC1 terminator (3503-3726 bp), a loxP recombination site (3735-3768 bp), a ScTEF1 promoter (3769-4224 bp), and the upstream portion of the *Aspergillus nidulans* acetamidase (4225-5264 bp). SEQ ID NO: 29 contains the following elements: the downstream portion of the *Aspergillus nidulans* acetamidase (7-1032 bp), a ScADH1 terminator (1033-1335 bp), a loxP recombination site (1336-1369 bp), a ScPGK1 promoter (1376-1962 bp), a *Rhizopus delemar* glucoamylase (1969-3783 bp), a ScGAL10 terminator (3792-4262 bp), and homology to integration locus A (4264-5026 bp). Transformants are selected on Yeast Nitrogen Base (without ammonium sulfate or amino acids) containing 20 g/L glucose and 1 g/L acetamide as the sole nitrogen source. Resulting transformants are streaked for single colony isolation on Yeast Nitrogen Base (without ammonium sulfate or amino acids) containing 20 g/l glucose and 1 g/L acetamide as the sole nitrogen source. A single colony is selected. Correct integration of SEQ ID NO: 28 and SEQ ID NO: 29 into the second allele of locus A is verified by PCR in the single colony. A PCR verified isolate is designated Strain 1-9.

Example 5

Characterization of Strains in 32% DS Corn Mash at 30° C. (TEST #1 and #2).

Strain 1, 1-3, 1-5, 1-7, 1-9 are struck to a YPD plate and incubated at 30° C. until single colonies are visible (1-2 days). Cells from the YPD plate are scraped into pH 7.0 phosphate buffer and the optical density (OD600) is measured. Optical density is measured at wavelength of 600 nm with a 1 cm path length using a model Genesys20 spectrophotometer (Thermo Scientific). A shake flask is inoculated with the cell slurry to reach an initial OD600 of 0.1. Immediately prior to inoculating the following materials are added to each flask: 50 grams of liquified corn mash (32% DS, DE 30+/−2) is added to a 250 mL baffled shake flask sealed with air-lock containing 4 mls of sterilized canola oil, 190 ul of 500 g/L filter-sterilized urea, and 2.5 ul of 100 mg/ml of filter sterilized ampicillin.

0.324 AGU/g DS (70 µl of a 1:10 dilution) of glucoamylase (Spirizyme Fuel HS, Novozymes) is added to flasks containing the control Strain 1, and either zero or 0.097 AGU/g DS (21 µL of a 1:10 dilution of glucoamylase (Spirizyme Fuel HS™, Novozymes is added to the remaining flasks depending on the "Test". Spirizyme Fuel HS™ is estimated to have approximately 769 AGU/g enzyme, however over time the activity can change 10-20% (i.e., the activity of the enzyme typically decreases over time). Duplicate flasks for each strain are incubated at 30° C. with shaking in an orbital shaker at 100 rpm for approximately 48 hours. At 48 hours, 1 ml samples are taken and analyzed for ethanol and glucose concentrations in the broth by high performance liquid chromatography with refractive index detector. Selected results are shown in Table 6.

TABLE 6

| | Test #1<br>Final EtOH titer<br>(g/kg) | Test #1<br>Residual Glucose<br>(g/kg) |
|---|---|---|
| Strain 1, with 0.324 AGU/g DS | 133.6 +/− 1.6 | 0.4 +/− 0.1 |
| Strain 1-3, no supplementation | 132.5 +/− 0.3 | 0.2 +/− 0.0 |
| Strain 1-5, no supplementation | 120.9 +/− 1.3 | 0.5 +/− 0.1 |
| Strain 1-7, no supplementation | 134.1 +/− 4.8 | 0.2 +/− 0.0 |
| Strain 1-9, no supplementation | 119.8 +/− 1.9 | 0.9 +/− 0.0 |

| | Test #2<br>Final EtOH titer<br>(g/kg) | Test #2<br>Residual Glucose<br>(g/kg) |
|---|---|---|
| Strain 1, with 0.324 AGU/g DS | 133.6 +/− 1.6 | 0.4 +/− 0.1 |
| Strain 1-3, no supplementation | 130.7 +/− 2.7 | 0.2 +/− 0.1 |
| Strain 1-5, no supplementation | 132.9 +/− 0.2 | 0.3 +/− 0.0 |
| Strain 1-7, no supplementation | 135.0 +/− 1.2 | 0.3 +/− 0.0 |
| Strain 1-9, no supplementation | 131.9 +/− 0.5 | 0.2 +/− 0.1 |

Example 6

Characterization of Strains in 32% DS Corn Mash at 33.3° C. (TEST #3 and #4).

Strain 1, 1-3, 1-5, 1-7, 1-9 are struck to a YPD plate and incubated at 30° C. until single colonies are visible (1-2 days). Cells from the YPD plate are scraped into pH 7.0 phosphate buffer and the optical density ($OD_{600}$) is measured. Optical density is measured at wavelength of 600 nm with a 1 cm path length using a model Genesys20 spectrophotometer (Thermo Scientific). A shake flask is inoculated with the cell slurry to reach an initial $OD_{600}$ of 0.1. Immediately prior to inoculating the following materials are added to each flask: 50 grams of liquified corn mash is added to a 250 mL baffled shake flask sealed with air-lock containing 4 mls of sterilized canola oil, 190 ul of 500 g/L filter-sterilized urea, and 2.5 ul of 100 mg/ml of filter sterilized ampicillin 0.324 AGU/g DS (70 µl of a 1:10 dilution) of glucoamylase (Spirizyme Fuel HS™, Novozymes) is added to flasks containing the control Strain 1, and either zero or 0.097 AGU/g DS (21 µl of a 1:10 dilution) of glucoamylase (Spirizyme Fuel HS™, Novozymes) is added to the remaining flasks, depending on the "Test". Spirizyme Fuel HS™ is estimated to have approximately 326 AGU/g enzyme. Duplicate flasks for each strain are incubated at 33.3° C. with shaking in an orbital shake at 100 rpm for approximately 48 hours. At 48 hours, 1 ml samples are taken and analyzed for ethanol and glucose concentrations in the broth by high performance liquid chromatography with refractive index detector. Selected results are shown in Table 7.

TABLE 7

| | Test #3<br>Final EtOH titer<br>(g/kg) | Test #3<br>Residual Glucose<br>(g/kg) |
|---|---|---|
| Strain 1, with 0.324 AGU/g DS | 135.8 +/− 0.4 | 0.8 +/− 0.1 |
| Strain 1-3, no supplementation | 124.1 +/− 4.4 | 6.0 +/− 0.0 |
| Strain 1-5, no supplementation | 132.8 +/− 1.2 | 0.2 +/− 0.0 |
| Strain 1-7, no supplementation | 131.2 +/− 2.4 | 2.6 +/− 0.2 |
| Strain 1-9, no supplementation | 132.9 +/− 1.2 | 0.2 +/− 0.0 |

| | Test #4<br>Final EtOH titer<br>(g/kg) | Test #4<br>Residual Glucose<br>(g/kg) |
|---|---|---|
| Strain 1, with 0.324 AGU/g DS | 135.8 +/− 0.4 | 0.8 +/− 0.1 |
| Strain 1-3 with 0.097 AGU/g DS | 129.5 +/− 3.6 | 3.3 +/− 0.0 |
| Strain 1-5, with 0.097 AGU/g DS | 132.8 +/− 0.3 | 0.4 +/− 0.2 |
| Strain 1-7, with 0.097 AGU/g DS | 129.5 +/− 0.9 | 7.9 +/− 0.2 |
| Strain 1-9, with 0.097 AGU/g DS | 134.5 +/− 1.5 | 0.9 +/− 0.1 |

Example 7

Characterization of Strains in 34% DS Corn Mash at 33.3° C.

Strains 1, 1-3, 1-6, and 1-9 are struck to a YPD plate and incubated at 30° C. until single colonies are visible (1-2 days). Cells from the YPD plate are scraped into pH 7.0 phosphate buffer and the optical density ($OD_{600}$) is measured. Optical density is measured at wavelength of 600 nm with a 1 cm path length using a model Genesys20 spectrophotometer (Thermo Scientific). A shake flask is inoculated with the cell slurry to reach an initial $OD_{600}$ of 0.1. Immediately prior to inoculating the following materials are added to each flask: 50 grams of liquified corn mash is added to a 250 mL baffled shake flask sealed with air-lock containing 4 mls of sterilized canola oil, 190 ul of 500 g/L filter-sterilized urea, and 2.5 ul of 100 mg/ml of filter sterilized ampicillin 0.324 AGU/g DS (70 µl of a 1:10 dilution) of glucoamylase (Spirizyme Fuel HS™, Novozymes) is added to flasks containing the control Strain 1, and either zero or 0.032 AGU/g DS, 0.065 AGU/g DS, 0.097 AGU/g DS, or 0.162 AGU/gDS. (7 µl, 14 µl, 21 µl, or 35 µl of a 1:10 dilution) is added to the remaining flasks. Spirizyme Fuel HS™ is estimated to have approximately 326 AGU/g enzyme. Duplicate flasks for each strain are incubated at 33.3° C. with shaking in an orbital shake at 100 rpm for approximately 48 hours. At various intervals, the flasks are opened and samples are analyzed for ethanol and glucose concentrations in the broth by high performance liquid chromatography with refractive index detector. Selected results are shown in Table 8.

TABLE 8

|  | Final EtOH titer (g/kg) | Residual Glucose (g/kg) |
| --- | --- | --- |
| Strain 1, 0.324 AGU/g DS dose | 137.0 +/− 2.8 | 1.2 +/− 0.3 |
| Strain 1-3, no supplementation | 123.2 +/− 1.1 | 12.1 +/− 0.5 |
| Strain 1-3, 0.032 AGU/g DS dose | 122.3 +/− 3.2 | 14.8 +/− 0.8 |
| Strain 1-3, 0.065 AGU/g DS dose | 123.4 +/− 4.2 | 16.8 +/− 0.0 |
| Strain 1-3, 0.097 AGU/g dose DS | 130.1 +/− 1.4 | 14.6 +/− 0.3 |
| Strain 1-6, no GA dose | 133.9 +/− 5.1 | 0.2 +/− 0.1 |
| Strain 1-6, 0.032 AGU/g dose DS | 137.5 +/− 3.7 | 0.6 +/− 0.0 |
| Strain 1-6, 0.097 AGU/g dose DS | 138.8 +/− 0.2 | 1.0 +/− 0.0 |
| Strain 1-6, 0.162 AGU/gDS dose | 138.4 +/− 2.8 | 2.0 +/− 0.7 |
| Strain 1-9, no supplementation | 135.1 +/− 0.3 | 1.2 +/− 0.1 |
| Strain 1-9, 0.032 AGU/g DS dose | 136.2 +/− 5.4 | 1.4 +/− 0.2 |
| Strain 1-9, 0.097 AGU/g DS dose | 135.7 +/− 1.0 | 4.8 +/− 0.9 |
| Strain 1-9, 0.162 AGU/g DS dose | 136.0 +/− 2.0 | 6.1 +/− 0.3 |

Example 8

Characterization of a Strain in 32% DS Corn Mash Having a DE of 30+/−2 at a Temperature of 30° C.

A strain is struck to a YPD plate (20 g/L yeast peptone, 10 g/L yeast extract, 20 g/L glucose, and 20 g/L agar) and incubated at 30° C. until single colonies are visible (1-2 days). Cells from the YPD plate are scraped into pH 7.0 phosphate buffer to create a cell slurry and the optical density ($OD_{600}$) is measured. Optical density is measured at wavelength of 600 nm with a 1 cm path length using a model Genesys20 spectrophotometer (Thermo Scientific). A shake flask is inoculated with the cell slurry to reach an initial $OD_{600}$ of 0.1. Immediately prior to inoculating the following materials are added to each flask: 50 grams of liquified corn mash (32% DS, DE 30) is added to a 250 mL baffled shake flask sealed with air-lock containing 4 mls of sterilized canola oil, 190 ul of 500 g/L filter-sterilized urea, and 2.5 ul of 100 mg/ml of filter sterilized ampicillin. The shake flask, airlock, canola oil is weighed prior to the addition of the fermentation media and cells, which is subtracted from the total weight of the flask to give the starting media volume. At various time points in the fermentation, the flasks are removed and the weight recorded. The mass loss (grams) at any timepoint is calculated by subtracting the mass at T1 from the original mass at T0. The mass loss (grams) is converted to a mass loss (percentage) by dividing the mass loss at any given time point by the original starting mass. The percentage mass loss can be converted to g/kg ethanol by the following equation (the starting mass of the fermentation media. Ethanol (g/kg)=(Percent mass loss+0.0016)/0.0009/1.042.

Exemplary Embodiments

A. An engineered yeast comprising an exogenous nucleic acid encoding a glucoamylase comprising a sequence having 81% or greater sequence identity to SEQ ID NO:1, wherein the yeast is capable of producing ethanol at a rate of 1 g/L*h or greater during a fermentation process.

B. An engineered yeast comprising an exogenous nucleic acid encoding a glucoamylase comprising a sequence having 81% or greater sequence identity to SEQ ID NO:1, wherein the yeast is capable of producing (a) at least 70 g/kg of ethanol in a fermentation medium made from a glucose polymer-containing feedstock having (i) a DE of not greater than 50.

C. An engineered yeast comprising an exogenous nucleic acid encoding a glucoamylase comprising a sequence having 81% or greater sequence identity to SEQ ID NO:1, wherein the yeast is capable of producing (a) at least 70 g/kg of ethanol in a fermentation medium made from corn mash having a DE of 30+/−2, wherein the fermentation medium comprises 32% dry wt corn, and a pH 5.8, 35 ppm CaCl, 1900 ppm urea, 5 ppm ampicillin, wherein the staring yeast concentration is 0.1 (OD600), and fermentation is carried out at 48 hrs at 30° C. with agitation.

D. The engineered yeast of any of embodiments A-C wherein the glucoamylase comprises a sequence having 85% or greater sequence identity to SEQ ID NO:1.

E. The engineered yeast of embodiment D wherein the glucoamylase comprises a sequence having 90% or greater sequence identity to SEQ ID NO:1.

F. The engineered yeast of embodiment E wherein the glucoamylase comprises a sequence having 95%, 96%, 97%, 98%, or 99%, or greater sequence identity to SEQ ID NO:1.

G. An engineered yeast comprising an exogenous nucleic acid encoding a glucoamylase comprising a sequence having 97% or greater sequence identity to SEQ ID NO:4, wherein the yeast is capable of producing ethanol at a rate of 1 g/L*h or greater during a fermentation process.

H. An engineered yeast comprising an exogenous nucleic acid encoding a glucoamylase comprising a sequence having 97% or greater sequence identity to SEQ ID NO:4, wherein the yeast is capable of producing (a) at least 70 g/kg of ethanol in a fermentation medium made from a glucose polymer-containing feedstock having (i) a DE of not greater than 50.

I. An engineered yeast comprising an exogenous nucleic acid encoding a glucoamylase comprising a sequence having 81% or greater sequence identity to SEQ ID NO:4, wherein the yeast is capable of producing (a) at least 70 g/kg of ethanol in a fermentation medium made from corn mash having a DE of 30, wherein the corn mash is present in a fermentation medium having 32% wt corn mash, and a pH 5.8, 35 ppm CaCl, 1900 ppm urea, 5 ppm ampicillin, wherein the staring yeast concentration is 0.1 (OD600), and fermentation is carried out at 48 hrs at 30° C. with agitation.

J. The engineered yeast of any of embodiments G-I wherein the glucoamylase comprises a sequence having 98% or greater sequence identity to SEQ ID NO:4.

K. The engineered yeast of embodiment J wherein the glucoamylase comprises a sequence having 99% or greater sequence identity to SEQ ID NO:4.

L. The engineered yeast of any of the above embodiments wherein there are 2-8 copies of the exogenous nucleic acid in the cell.

M. The engineered yeast of embodiment L wherein there are 2-6 copies of the exogenous nucleic acid in the cell.

N. The engineered yeast of embodiment M wherein there are 4 copies of the exogenous nucleic acid in the cell.

O. The engineered yeast of any of the above embodiments wherein the exogenous nucleic acid is under the control of a promoter selected from the group consisting of a phosphoglycerate kinase (PGK) promoter nucleic acid sequence, cytochrome c promoter (pCYC) nucleic acid sequence, translational elongation factor promoter (pTEF) nucleic acid sequence, glyceraldehyde-3phosphate dehydrogenase promoter (pGPD/TDH3) nucleic acid sequence, the phosphoglycerate kinase promoter (PGK) nucleic acid sequence, and the alcohol dehydrogenase promoter (pADH) nucleic acid sequence.

P. The engineered yeast of any of the above embodiments which is a species of *Saccharomyces*.

Q. The engineered yeast of embodiment P which is *Saccharomyces cerevisiae*.

R. The engineered yeast of any of the above embodiments which is tolerant to growth in fermentation medium having a concentration of ethanol of greater than 90 g/L.

S. The engineered yeast of any of the above embodiments which is tolerant to growth at temperatures in the range of greater than 31° C.-35° C.

T. The engineered yeast of embodiment S which is tolerant to growth in at temperatures in the range of greater than 32° C.-34° C.

U. The engineered yeast of any one of the above embodiments that produces a greater amount of ethanol than a parent strain that does not include the exogenous nucleic acid under the same fermentation conditions.

V. A fermentation method for producing a fermentation product, comprising a step of: forming a fermentation medium from a glucose polymer-containing feedstock; and fermenting the fermentation medium using an engineered yeast comprising an exogenous nucleic acid encoding a glucoamylase comprising a sequence having 81% or greater sequence identity to SEQ ID NO:1, wherein fermenting produces the bioproduct.

W. A fermentation method for producing a fermentation product, comprising a step of: forming a fermentation medium from a glucose polymer-containing feedstock; and fermenting the fermentation medium using an engineered yeast comprising an exogenous nucleic acid encoding a glucoamylase comprising a sequence having 97% or greater sequence identity to SEQ ID NO:4, wherein fermenting produces the bioproduct.

X. The fermentation method of embodiments V or W wherein the glucose polymer-containing feedstock or the fermentation medium, at the beginning of fermentation, has a DE of about 50 or less.

Y. The fermentation method of embodiments V or W wherein the fermentation medium, at the beginning of fermentation, has a glucose concentration of about 30 g/kg or less.

Z. The fermentation method of embodiments V or W wherein glucose polymer-containing feedstock comprises glucose polymer having a degree of polymerization of 4 or greater and present in an amount of 75% weight or greater total fermentable carbohydrates in the feedstock.

AA. The fermentation method of any of embodiments V-Z wherein glucose polymer-containing feedstock is obtained from corn.

BB. The fermentation method of embodiment AA wherein glucose polymer-containing feedstock is obtained from corn mash.

CC. The fermentation method of any of embodiments V-BB wherein fermenting is carried out for a fermentation time of at least 30 hours.

DD. The fermentation method of embodiment CC wherein fermenting is carried out for a fermentation time in the range of 30-100 hours.

EE. The fermentation method of embodiment DD wherein fermenting is carried out for a fermentation time in the range of 40-60 hours.

FF. The fermentation method of any of embodiments V-EE wherein said fermenting is carried out at a temperature in the range of 31° C. to 35° C. for most or all of a fermentation period.

GG. The fermentation method of embodiment FF wherein the fermenting is carried out at a temperature in the range of 32° C. to 34° C. for most or all of the fermentation period.

HH. The fermentation of any of embodiments V-GG wherein ethanol is produced to a concentration of 70 g/L or greater in the medium.

II. The fermentation of embodiment HH wherein ethanol is produced to a concentration of 90 g/L or greater in the medium.

JJ. The method of embodiment II wherein said fermenting provides ethanol in the range of 90 g/L to 150 g/L.

KK. The method of embodiment JJ wherein said fermenting provides ethanol in the range of 110 g/L to 150 g/L.

LL. The fermentation method of any of embodiments V-KK wherein the fermentation medium has an amount of glucose of not greater than 1.0 g/L at the end of the fermentation period.

MM. The fermentation method of embodiment LL wherein the fermentation medium has an amount of glucose of not greater than 0.8 g/L at the end of the fermentation period.

NN. The fermentation method of any of embodiments V-MM comprising adding supplemental glucoamylase to the feedstock, or supplemental glucoamylase to the medium during the fermentation period.

OO. An engineered yeast comprising an exogenous nucleic acid encoding a glucoamylase comprising a sequence having 81% or greater sequence identity to SEQ ID NO:1, wherein the yeast is capable of producing at least 70 g/kg of ethanol in the fermentation process of Example 8.

PP. An engineered yeast comprising an exogenous nucleic acid encoding a glucoamylase comprising a sequence having 97% or greater sequence identity to SEQ ID NO:4, wherein the yeast is capable of producing at least 70 g/kg of ethanol in the fermentation process of Example 8.

What is claimed is:

1. An engineered yeast comprising an exogenous nucleic acid encoding a glucoamylase comprising a sequence having 90% or greater sequence identity to SEQ ID NO:1, wherein the yeast is capable of producing ethanol at a rate of 1 g/L*h or greater during a fermentation process.

2. The engineered yeast of claim 1, wherein the yeast is capable of producing at least 70 g/kg of ethanol in a fermentation medium made from a glucose polymer-containing feedstock having a dextrose equivalent (DE) of not greater than 50.

3. The engineered yeast of claim 1, wherein the yeast is capable of producing at least 70 g/kg of ethanol in a fermentation medium made from corn mash having a DE of 30+/-2, wherein the fermentation medium comprises 32% dry wt corn, and a pH 5.8, 35 ppm CaCl, 1900 ppm urea, 5 ppm ampicillin, wherein the staring yeast concentration is 0.1 (OD600), and fermentation is carried out at 48 hrs at 30° C. with agitation.

4. The engineered yeast of claim 1, wherein the glucoamylase comprises a sequence having 95% or greater sequence identity to SEQ ID NO:1.

5. The engineered yeast of claim 1 wherein there are 2-8 copies of the exogenous nucleic acid in the cell.

6. The engineered yeast of claim 1 which is a *Saccharomyces cerevisiae* yeast.

7. The engineered yeast of claim 1 which is tolerant to growth in a fermentation medium having a concentration of ethanol of greater than 90 g/L.

8. The engineered yeast of claim 1 which is tolerant to growth at temperatures in the range of greater than 31° C.-35° C.

9. A fermentation method for producing a bioproduct, comprising:
    forming a fermentation medium from a glucose polymer-containing feedstock; and
    fermenting the fermentation medium using an engineered yeast comprising an exogenous nucleic acid encoding a glucoamylase comprising a sequence having 90% or greater sequence identity to SEQ ID NO:1, wherein fermenting produces a bioproduct and ethanol at a rate of 1 g/L*h or greater.

10. The fermentation method of claim 9, wherein the glucose polymer-containing feedstock or the fermentation medium, at the beginning of fermentation, has a DE of about 50 or less.

11. The fermentation method of claim 9, wherein the glucose polymer-containing feedstock comprises glucose polymer having a degree of polymerization of 4 or greater and present in an amount of 75% weight or greater total fermentable carbohydrates in the feedstock.

12. The fermentation of any of claim 9, wherein ethanol is produced to a concentration of 70 g/L or greater in the medium.

13. The fermentation method of any of claim 9, comprising adding supplemental glucoamylase to the feedstock, or supplemental glucoamylase to the medium during the fermentation period.

* * * * *